US012578343B2

(12) United States Patent
Meyrath et al.

(10) Patent No.: US 12,578,343 B2
(45) Date of Patent: Mar. 17, 2026

(54) SELECTIVE ACKR3 MODULATORS AND USES THEREOF

(71) Applicant: Luxembourg Institute of Health (LIH), Luxembourg (LU)

(72) Inventors: Max Marc Roger Meyrath, Leudelange (LU); Martyna Szpakowska, Luxembourg (LU); Andy Chevigné, Saint Léger (BD)

(73) Assignee: Luxembourg Institute of Health (LIH), Luxembourg (LU)

( * ) Notice: Subject to any disclaimer, the term of this patent is extended or adjusted under 35 U.S.C. 154(b) by 1171 days.

(21) Appl. No.: 17/608,427

(22) PCT Filed: Apr. 30, 2020

(86) PCT No.: PCT/EP2020/061981
§ 371 (c)(1),
(2) Date: Nov. 2, 2021

(87) PCT Pub. No.: WO2020/225070
PCT Pub. Date: Nov. 12, 2020

(65) Prior Publication Data
US 2022/0236279 A1 Jul. 28, 2022

(30) Foreign Application Priority Data
May 3, 2019 (EP) .................................... 19172560

(51) Int. Cl.
*G01N 33/58* (2006.01)
*A61K 38/00* (2006.01)
*C07K 7/08* (2006.01)

(52) U.S. Cl.
CPC ............. *G01N 33/582* (2013.01); *C07K 7/08* (2013.01); *A61K 38/00* (2013.01); *C07K 2319/33* (2013.01); *G01N 2333/726* (2013.01); *G01N 2500/02* (2013.01); *G01N 2800/52* (2013.01)

(58) Field of Classification Search
None
See application file for complete search history.

(56) References Cited

U.S. PATENT DOCUMENTS 7,323,308 B2 * 1/2008 Barts ...................... C12Q 1/689
536/23.1

FOREIGN PATENT DOCUMENTS

WO WO 2011/095218 * 8/2011 ............... C07K 7/64

OTHER PUBLICATIONS

Meyrath et al., Nature Communications (2020) 11: 3033; https://doi.org/10.1038/s41467-020-16664-0; 16 pages total (Year: 2020).*

(Continued)

*Primary Examiner* — Christina M Borgeest
(74) *Attorney, Agent, or Firm* — Leydig, Voit & Mayer, Ltd.

(57) ABSTRACT

The application discloses selective ACKR3 modulating peptides comprising amino acid sequence $FGGX_1MRRX_2$ (SEQ ID NO: 1), wherein $X_1$ is F or W; $X_2$ is K, V or F; and wherein the peptides have a length of at most 15 amino acids; fusion proteins comprising the peptides as taught herein; nucleic acids encoding the peptides as taught herein; nucleic acid expression cassettes and vectors comprising the nucleic acid as taught herein; and pharmaceutical compositions comprising the peptide as taught herein or the nucleic acid as taught herein. Further provided are the peptide as taught herein for use as a medicament; methods for in vitro or ex vivo diagnosis, prediction, prognosis and/or monitoring of a disease or condition characterized by an aberrant level of ACKR3 polypeptide using the peptide as taught herein; and in vitro methods for identifying an agent useful as a therapeutic using the peptide as taught herein.

15 Claims, 21 Drawing Sheets
Specification includes a Sequence Listing.

(56)     References Cited

OTHER PUBLICATIONS

Li et al., Cardiovascular Research, (2010) vol. 87, Supp. Suppl. 1, pp. S130. Abstract No. 489, Jul. 16, 2010-Jul. 19, 2010 (Year: 2010).*

Duval et al., Front. Endocrinol. (2022) 13:906586, doi: 10.3389/fendo.2022.906586 (Year: 2022).*

Isci et al., Nature Portfolio (2024) 14: 21925 (Year: 2024).*

Rath et al., J. Thromb. Haemost. 2015, 13, 719-728 (Year: 2015).*

Bayrak et al., J. Med. Chem. 2022, 65, 13365-13384 (Year: 2022).*

Antoine Gardin and Giuseppe Ronzitti, Archives de Pédiatrie 30 (2023) 8S46-8S52 (Year: 2023).*

Jafarlou et al., Journal of Biological Regulators & Homeostatic Agents, 2016: 30: 315-321 (Year: 2016).*

Van Bulck et al., Int. J. Mol. Sci. 2019, 20, 719; doi: 10.3390/ijms20030719; 36 pages total (Year: 2019).*

Szpakowska et al., Signal Transduction and Targeted Therapy (2021) 6:209 (Year: 2021).*

Ikeda et al., "Modulation of circadian glucocorticoid oscillation via adrenal opioid-CXCR7 signaling alters emotional behavior," *Cell*, 155(6): 1323-1336 (Dec. 5, 2013).

Koenen et al. "Atypical chemokine receptor 3 (ACKR3): a comprehensive overview of its expression and potential roles in the immune system," *Molecular Pharmacology*, 96(6): 809-818 (Apr. 30, 2019).

Mansour et al., "The cloned μ, δ and κ receptors and their endogenous ligands: evidence for two opioid peptide recognition cores," *Brain Research*, 700(1-2): 89-98 (Nov. 27, 1995).

Wang et al., "CXCR7 targeting and its major disease relevance," *Frontiers in Pharmacology*, 9: 641 (Jun. 21, 2018) (12 pp.).

European Patent Office, International Search Report in International Patent Application No. PCT/EP2020/061981, 4 pp. (Aug. 7, 2020).

European Patent Office, Written Opinion in International Patent Application No. PCT/EP2020/061981, 6 pp. (Aug. 7, 2020).

* cited by examiner

Table 1a

| Name | Sequence | SEQ ID NO |
|---|---|---|
| Dynorphin A | YGGFLRRIRPKLKWDNQ | 18 |
| Dynorphin A (2-17) | -GGFLRRIRPKLKWDNQ | 19 |
| Dynorphin A (2-13) | -GGFLRRIRPKLK | 20* |
| Dynorphin (1-13) | YGGFLRRIRPKLK | 21 |
| Dynorphin B | YGGFLRRQFKVVT | 22 |
| Leumorphin | YGGFLRRQFKVVTRSQEDPNAYSGELFDA | 23 |
| Big Dynorphin | YGGFLRRIRPKLKWDNQKRYGGFLRRQFKVVT | 24 |
| Met enkephalin | YGGFM | 25 |
| Adrenorphin | YGGFMRRV | 32* |
| BAM22 | YGGFMRRVGRPEWWMDYQKRYG | 26 |
| Nociceptin | FGGFTGARKSARKLANQ | 27 |
| Nociceptin (1-13) | FGGFTGARKSARK | 28* |
| [Phe1ψ(CH2-NH)-Gly2]nociceptin-(1-13) | Fψ(CH2-NH)G]GFTGARKSARK | 13* |
| Endomorphin-1 | YPWF | 29* |
| Endomorphin-2 | YPFF | 30* |
| B-endorphin | YGGFMTSEKSQTPLVTLFKNAIIIKNAYKKGE | 31 |
| LIH383 | FGGFMRRK | 3* |

*$NH_2$-substituted at C-terminus

Table 1b

| Name | Binding competition | | B-arrestin-1 | |
|---|---|---|---|---|
| | ACKR3 | | ACKR3 | |
| | IC50 (nM) | pIC50 ± SEM | EC50 (nM) | pEC50 ± SEM |
| Dynorphin A | 82.7 | 7.08 ± 0.06 | 110.2 | 6.96 ± 0.03 |
| Dynorphin A (2-17) | 11060 | 4.96 ± 0.06 | 1848 | 5.73 ± 0.13 |
| Dynorphin A (2-13) | 20910 | 4.68 ± 0.11 | 5075 | 5.30 ± 0.49 |
| Dynorphin (1-13) | 131.6 | 6.88 ± 0.04 | 61.8 | 7.21 ± 0.04 |
| Dynorphin B | 465.4 | 6.33 ± 0.09 | 727.3 | 6.14 ± 0.19 |
| Leumorphin | 6909 | 5.16 ± 0.07 | 1320 | 5.88 ± 0.12 |
| Big Dynorphin | 34.0 | 7.47 ± 0.06 | 108.1 | 6.97 ± 0.04 |
| Met enkephalin | Not active | Not active | Not active | Not active |
| Adrenorphin | 49.0 | 7.31 ± 0.06 | 56.5 | 7.25 ± 0.10 |
| BAM22 | 32.7 | 7.49 ± 0.03 | 23.5 | 7.63 ± 0.15 |
| Nociceptin | >10000 | <5.00 | >10.000 | < 5.00 |
| Nociceptin (1-13) | >10000 | <5.00 | >10.000 | < 5.00 |
| [Phe1ψ(CH2-NH)-Gly2]nociceptin-(1-13) | >10000 | <5.00 | 2966 | 5.53 ± 0.18 |
| Endomorphin-1 | Not active | Not active | Not active | Not active |
| Endomorphin-2 | Not active | Not active | Not active | Not active |
| B-endorphin | Not active | Not active | Not active | Not active |
| LIH383 | 4.0 | x8.40 ± 0.05 | 0.61 | x9.21 ± 0.17 |

FIG. 3

A position

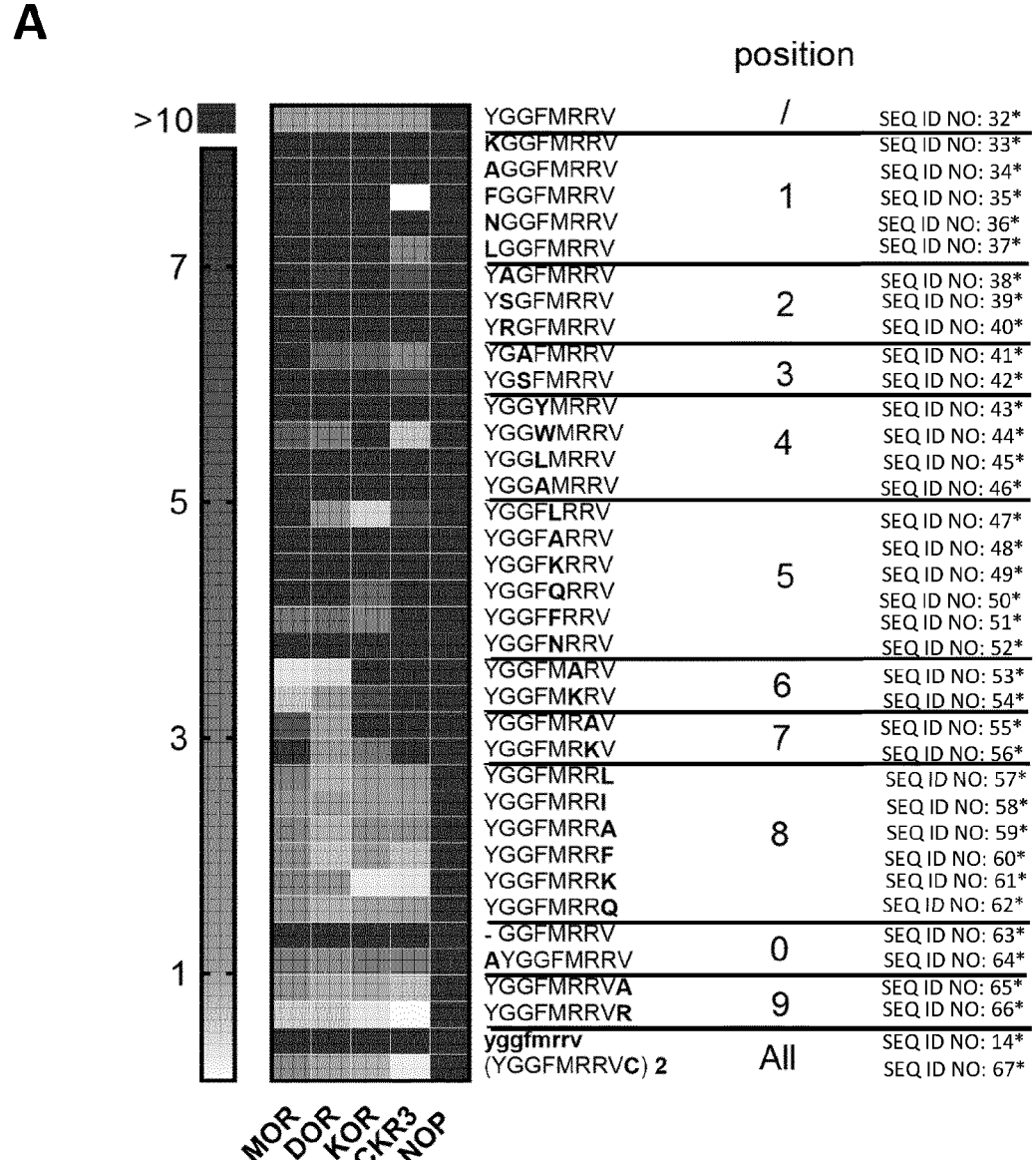

| Sequence | position | SEQ ID |
|---|---|---|
| YGGFMRRV | / | SEQ ID NO: 32* |
| KGGFMRRV | | SEQ ID NO: 33* |
| AGGFMRRV | | SEQ ID NO: 34* |
| FGGFMRRV | 1 | SEQ ID NO: 35* |
| NGGFMRRV | | SEQ ID NO: 36* |
| LGGFMRRV | | SEQ ID NO: 37* |
| YAGFMRRV | | SEQ ID NO: 38* |
| YSGFMRRV | 2 | SEQ ID NO: 39* |
| YRGFMRRV | | SEQ ID NO: 40* |
| YGAFMRRV | 3 | SEQ ID NO: 41* |
| YGSFMRRV | | SEQ ID NO: 42* |
| YGGYMRRV | | SEQ ID NO: 43* |
| YGGWMRRV | 4 | SEQ ID NO: 44* |
| YGGLMRRV | | SEQ ID NO: 45* |
| YGGAMRRV | | SEQ ID NO: 46* |
| YGGFLRRV | | SEQ ID NO: 47* |
| YGGFARRV | | SEQ ID NO: 48* |
| YGGFKRRV | 5 | SEQ ID NO: 49* |
| YGGFQRRV | | SEQ ID NO: 50* |
| YGGFFRRV | | SEQ ID NO: 51* |
| YGGFNRRV | | SEQ ID NO: 52* |
| YGGFMARV | 6 | SEQ ID NO: 53* |
| YGGFMKRV | | SEQ ID NO: 54* |
| YGGFMRAV | 7 | SEQ ID NO: 55* |
| YGGFMRKV | | SEQ ID NO: 56* |
| YGGFMRRL | | SEQ ID NO: 57* |
| YGGFMRRI | | SEQ ID NO: 58* |
| YGGFMRRA | 8 | SEQ ID NO: 59* |
| YGGFMRRF | | SEQ ID NO: 60* |
| YGGFMRRK | | SEQ ID NO: 61* |
| YGGFMRRQ | | SEQ ID NO: 62* |
| - GGFMRRV | 0 | SEQ ID NO: 63* |
| AYGGFMRRV | | SEQ ID NO: 64* |
| YGGFMRRVA | 9 | SEQ ID NO: 65* |
| YGGFMRRVR | | SEQ ID NO: 66* |
| yggfmrrv | All | SEQ ID NO: 14* |
| (YGGFMRRVC) 2 | | SEQ ID NO: 67* |

>10

7

5

3

1

MOR DOR KOR ACKR3 NOP

*NH₂-substituted at C-terminus (YGGFMRRVC)2 = dimeric form of YGGFMRRVC

F

| 2nd generation peptides | | ACKR3 | |
|---|---|---|---|
| Sequence | SEQ ID NO | EC50 (nM) | pEC50 ± SEM |
| FGGFMRRK\* (LIH383) | 3 | 0.61 | 9.21 ± 0.17 |
| FGGFMRRKR\* | 4 | 1.11 | 8.96 ± 0.20 |
| FGGFMRRVR\* | 5 | 3.97 | 8.40 ± 0.09 |
| FGGWMRRK\* | 6 | 4.03 | 8.39 ± 0.11 |
| FGGWMRRVR\* | 10 | 5.42 | 8.27 ± 0.11 |
| FGGWMRRKR\* | 11 | 7.34 | 8.14 ± 0.13 |
| FGGWMRRV\* | 68 | 10.52 | 7.98 ± 0.62 |
| FGGFMRRF\* | 69 | 10.96 | 7.96 ± 0.29 |
| FGGFMRRFR\* | 70 | 16.34 | 7.79 ± 0.24 |
| FGGWMRRFR\* | 71 | 19.07 | 7.72 ± 0.22 |
| FGGWMRRF\* | 72 | 19.1 | 7.72 ± 0.20 |
| FGGFMRRV\* (mother peptide) | 35 | 9.33 | 8.03 ± 0.11 |
| YGGFMRRV\* (adrenorphin) | 32 | 108.7 | 6.96 ± 0.09 |

\*$NH_2$-substituted at C-terminus

F

G

A

- U87
- U87.ACKR3
- U87.ACKR3 + LIH383

B

Dynorphin A 1-13  Big Dynorphin  BAM22  Nociceptin

C

D

E

F

A amygdaloid complex anterior (rostral) cingulate
(medial prefrontal) cortex hippocampus
(hippocampal formation)

mediodorsal nucleus
of thalamus

C

D

ACKR3 expression in smNPCs

E

F

G

H

I

SEQUENCE LISTING

```
<160> NUMBER OF SEQ ID NOS: 76

<210> SEQ ID NO 1
<211> LENGTH: 8
<212> TYPE: PRT
<213> ORGANISM: Artificial Sequence
<220> FEATURE:
<223> OTHER INFORMATION: consensus sequence 1
<220> FEATURE:
<221> NAME/KEY: SITE
<222> LOCATION: (4)..(4)
<223> OTHER INFORMATION: Xaa is Phe or Trp
<220> FEATURE:
<221> NAME/KEY: SITE
<222> LOCATION: (8)..(8)
<223> OTHER INFORMATION: Xaa is Lys, Val or Phe

<400> SEQUENCE: 1

Phe Gly Gly Xaa Met Arg Arg Xaa
1               5

<210> SEQ ID NO 2
<211> LENGTH: 9
<212> TYPE: PRT
```

```
<213> ORGANISM: Artificial Sequence
<220> FEATURE:
<223> OTHER INFORMATION: consensus sequence 2
<220> FEATURE:
<221> NAME/KEY: SITE
<222> LOCATION: (4)..(4)
<223> OTHER INFORMATION: Xaa is Phe or Trp
<220> FEATURE:
<221> NAME/KEY: SITE
<222> LOCATION: (8)..(8)
<223> OTHER INFORMATION: Xaa is Lys, Val or Phe
<220> FEATURE:
<221> NAME/KEY: SITE
<222> LOCATION: (9)..(9)
<223> OTHER INFORMATION: Xaa can be any amino acid

<400> SEQUENCE: 2

Phe Gly Gly Xaa Met Arg Arg Xaa Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: peptide 1 - LIH383

<400> SEQUENCE: 3

Phe Gly Gly Phe Met Arg Arg Lys
1               5

<210> SEQ ID NO 4
<211> LENGTH: 9
<212> TYPE: PRT
<213> ORGANISM: Artificial Sequence
<220> FEATURE:
<223> OTHER INFORMATION: peptide 2

<400> SEQUENCE: 4

Phe Gly Gly Phe Met Arg Arg Lys Arg
1               5

<210> SEQ ID NO 5
<211> LENGTH: 9
<212> TYPE: PRT
<213> ORGANISM: Artificial Sequence
<220> FEATURE:
<223> OTHER INFORMATION: peptide 3

<400> SEQUENCE: 5

Phe Gly Gly Phe Met Arg Arg Val Arg
1               5

<210> SEQ ID NO 6
<211> LENGTH: 8
<212> TYPE: PRT
<213> ORGANISM: Artificial Sequence
<220> FEATURE:
<223> OTHER INFORMATION: peptide 4

<400> SEQUENCE: 6

Phe Gly Gly Trp Met Arg Arg Lys
1               5

<210> SEQ ID NO 7
<211> LENGTH: 10
<212> TYPE: PRT
<213> ORGANISM: Artificial Sequence
<220> FEATURE:
```

```
<223> OTHER INFORMATION: consensus sequence 3
<220> FEATURE:
<221> NAME/KEY: SITE
<222> LOCATION: (4)..(4)
<223> OTHER INFORMATION: Xaa is Phe or Trp
<220> FEATURE:
<221> NAME/KEY: SITE
<222> LOCATION: (8)..(8)
<223> OTHER INFORMATION: Xaa is Lys, Val or Phe
<220> FEATURE:
<221> NAME/KEY: SITE
<222> LOCATION: (9)..(9)
<223> OTHER INFORMATION: Xaa can be any amino acid
<220> FEATURE:
<221> NAME/KEY: SITE
<222> LOCATION: (10)..(10)
<223> OTHER INFORMATION: Xaa can be any amino acid

<400> SEQUENCE: 7

Phe Gly Gly Xaa Met Arg Arg Xaa Xaa Xaa
1               5                   10

<210> SEQ ID NO 8
<211> LENGTH: 11
<212> TYPE: PRT
<213> ORGANISM: Artificial Sequence
<220> FEATURE:
<223> OTHER INFORMATION: consensus sequence 4
<220> FEATURE:
<221> NAME/KEY: SITE
<222> LOCATION: (4)..(4)
<223> OTHER INFORMATION: Xaa is Phe or Trp
<220> FEATURE:
<221> NAME/KEY: SITE
<222> LOCATION: (8)..(8)
<223> OTHER INFORMATION: Xaa is Lys, Val or Phe
<220> FEATURE:
<221> NAME/KEY: SITE
<222> LOCATION: (9)..(9)
<223> OTHER INFORMATION: Xaa can be any amino acid/
<220> FEATURE:
<221> NAME/KEY: SITE
<222> LOCATION: (10)..(10)
<223> OTHER INFORMATION: Xaa can be any amino acid
<220> FEATURE:
<221> NAME/KEY: SITE
<222> LOCATION: (11)..(11)
<223> OTHER INFORMATION: Xaa can be any amino acid

<400> SEQUENCE: 8

Phe Gly Gly Xaa Met Arg Arg Xaa Xaa Xaa Xaa
1               5                   10

<210> SEQ ID NO 9
<211> LENGTH: 12
<212> TYPE: PRT
<213> ORGANISM: Artificial Sequence
<220> FEATURE:
<223> OTHER INFORMATION: consensus sequence 5
<220> FEATURE:
<221> NAME/KEY: SITE
<222> LOCATION: (4)..(4)
<223> OTHER INFORMATION: Xaa is Phe or Trp
<220> FEATURE:
<221> NAME/KEY: SITE
<222> LOCATION: (8)..(8)
<223> OTHER INFORMATION: Xaa is Lys, Val or Phe
<220> FEATURE:
<221> NAME/KEY: SITE
<222> LOCATION: (9)..(9)
<223> OTHER INFORMATION: Xaa can be any amino acid
<220> FEATURE:
<221> NAME/KEY: SITE
<222> LOCATION: (10)..(10)
<223> OTHER INFORMATION: Xaa can be any amino acid
```

```
<220> FEATURE:
<221> NAME/KEY: SITE
<222> LOCATION: (11)..(11)
<223> OTHER INFORMATION: Xaa can be any amino acid
<220> FEATURE:
<221> NAME/KEY: SITE
<222> LOCATION: (12)..(12)
<223> OTHER INFORMATION: Xaa can be any amino acid
<220> FEATURE:
<221> NAME/KEY: SITE
<222> LOCATION: (12)..(12)
<223> OTHER INFORMATION: Xaa can be any amino acid

<400> SEQUENCE: 9

Phe Gly Gly Xaa Met Arg Arg Xaa Xaa Xaa Xaa Xaa
1               5                   10

<210> SEQ ID NO 10
<211> LENGTH: 9
<212> TYPE: PRT
<213> ORGANISM: Artificial Sequence
<220> FEATURE:
<223> OTHER INFORMATION: peptide 5

<400> SEQUENCE: 10

Phe Gly Gly Trp Met Arg Arg Val Arg
1               5

<210> SEQ ID NO 11
<211> LENGTH: 9
<212> TYPE: PRT
<213> ORGANISM: Artificial Sequence
<220> FEATURE:
<223> OTHER INFORMATION: peptide 6

<400> SEQUENCE: 11

Phe Gly Gly Trp Met Arg Arg Lys Arg
1               5

<210> SEQ ID NO 12
<211> LENGTH: 5
<212> TYPE: PRT
<213> ORGANISM: Artificial Sequence
<220> FEATURE:
<223> OTHER INFORMATION: consensus sequence 6
<220> FEATURE:
<221> NAME/KEY: SITE
<222> LOCATION: (1)..(1)
<223> OTHER INFORMATION: Xaa is Phe or Tyr
<220> FEATURE:
<221> NAME/KEY: SITE
<222> LOCATION: (5)..(5)
<223> OTHER INFORMATION: Xaa is Leu or Met

<400> SEQUENCE: 12

Xaa Gly Gly Phe Xaa
1               5

<210> SEQ ID NO 13
<211> LENGTH: 13
<212> TYPE: PRT
<213> ORGANISM: Homo sapiens
<220> FEATURE:
<221> NAME/KEY: SITE
<222> LOCATION: (1)..(1)
<223> OTHER INFORMATION: CH2-NH substituted
<220> FEATURE:
<221> NAME/KEY: SITE
<222> LOCATION: (13)..(13)
<223> OTHER INFORMATION: NH2 substituted
```

```
<400> SEQUENCE: 13

Phe Gly Gly Phe Thr Gly Ala Arg Lys Ser Ala Arg Lys
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Adrenorphin variant
<220> FEATURE:
<221> NAME/KEY: SITE
<222> LOCATION: (1)..(1)
<223> OTHER INFORMATION: D-isomer of Tyr
<220> FEATURE:
<221> NAME/KEY: SITE
<222> LOCATION: (2)..(3)
<223> OTHER INFORMATION: D-isomer of Gly
<220> FEATURE:
<221> NAME/KEY: SITE
<222> LOCATION: (4)..(4)
<223> OTHER INFORMATION: D-isomer of Phe
<220> FEATURE:
<221> NAME/KEY: SITE
<222> LOCATION: (5)..(5)
<223> OTHER INFORMATION: D-isomer of Met
<220> FEATURE:
<221> NAME/KEY: SITE
<222> LOCATION: (6)..(7)
<223> OTHER INFORMATION: D-isomer of Arg
<220> FEATURE:
<221> NAME/KEY: SITE
<222> LOCATION: (8)..(8)
<223> OTHER INFORMATION: D-isomer of Val

<400> SEQUENCE: 14

Tyr Gly Gly Phe Met Arg Arg Val
1               5

<210> SEQ ID NO 15
<211> LENGTH: 5
<212> TYPE: PRT
<213> ORGANISM: Artificial Sequence
<220> FEATURE:
<223> OTHER INFORMATION: consensus sequence 7
<220> FEATURE:
<221> NAME/KEY: SITE
<222> LOCATION: (5)..(5)
<223> OTHER INFORMATION: Xaa is Leu or Met

<400> SEQUENCE: 15

Tyr Gly Gly Phe Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: DADLE
<220> FEATURE:
<221> NAME/KEY: SITE
<222> LOCATION: (2)..(2)
<223> OTHER INFORMATION: D-isomer of Ala
<220> FEATURE:
<221> NAME/KEY: SITE
<222> LOCATION: (5)..(5)
<223> OTHER INFORMATION: D-isomer of Leu

<400> SEQUENCE: 16

Tyr Ala Gly Phe Leu
1               5
```

```
<210> SEQ ID NO 17
<211> LENGTH: 5
<212> TYPE: PRT
<213> ORGANISM: Artificial Sequence
<220> FEATURE:
<223> OTHER INFORMATION: DAMGO
<220> FEATURE:
<221> NAME/KEY: SITE
<222> LOCATION: (1)..(1)
<223> OTHER INFORMATION: hydrogen substituted
<220> FEATURE:
<221> NAME/KEY: SITE
<222> LOCATION: (2)..(2)
<223> OTHER INFORMATION: D-isomer of Ala
<220> FEATURE:
<221> NAME/KEY: SITE
<222> LOCATION: (4)..(4)
<223> OTHER INFORMATION: N-methyl substituted
<220> FEATURE:
<221> NAME/KEY: SITE
<222> LOCATION: (5)..(5)
<223> OTHER INFORMATION: OH-substituted

<400> SEQUENCE: 17

Tyr Ala Gly Phe Gly
1               5

<210> SEQ ID NO 18
<211> LENGTH: 17
<212> TYPE: PRT
<213> ORGANISM: Homo sapiens

<400> SEQUENCE: 18

Tyr Gly Gly Phe Leu Arg Arg Ile Arg Pro Lys Leu Lys Trp Asp Asn
1               5                   10                  15

Gln

<210> SEQ ID NO 19
<211> LENGTH: 16
<212> TYPE: PRT
<213> ORGANISM: Homo sapiens

<400> SEQUENCE: 19

Gly Gly Phe Leu Arg Arg Ile Arg Pro Lys Leu Lys Trp Asp Asn Gln
1               5                   10                  15

<210> SEQ ID NO 20
<211> LENGTH: 12
<212> TYPE: PRT
<213> ORGANISM: Homo sapiens
<220> FEATURE:
<221> NAME/KEY: SITE
<222> LOCATION: (12)..(12)
<223> OTHER INFORMATION: NH2-substituted

<400> SEQUENCE: 20

Gly Gly Phe Leu Arg Arg Ile Arg Pro Lys Leu Lys
1               5                   10

<210> SEQ ID NO 21
<211> LENGTH: 13
<212> TYPE: PRT
<213> ORGANISM: Homo sapiens

<400> SEQUENCE: 21

Tyr Gly Gly Phe Leu Arg Arg Ile Arg Pro Lys Leu Lys
1               5                   10
```

```
<210> SEQ ID NO 22
<211> LENGTH: 13
<212> TYPE: PRT
<213> ORGANISM: Homo sapiens

<400> SEQUENCE: 22

Tyr Gly Gly Phe Leu Arg Arg Gln Phe Lys Val Val Thr
1               5                   10

<210> SEQ ID NO 23
<211> LENGTH: 29
<212> TYPE: PRT
<213> ORGANISM: Homo sapiens

<400> SEQUENCE: 23

Tyr Gly Gly Phe Leu Arg Arg Gln Phe Lys Val Val Thr Arg Ser Gln
1               5                   10                  15

Glu Asp Pro Asn Ala Tyr Ser Gly Glu Leu Phe Asp Ala
            20                  25

<210> SEQ ID NO 24
<211> LENGTH: 32
<212> TYPE: PRT
<213> ORGANISM: Homo sapiens

<400> SEQUENCE: 24

Tyr Gly Gly Phe Leu Arg Arg Ile Arg Pro Lys Leu Lys Trp Asp Asn
1               5                   10                  15

Gln Lys Arg Tyr Gly Gly Phe Leu Arg Arg Gln Phe Lys Val Val Thr
            20                  25                  30

<210> SEQ ID NO 25
<211> LENGTH: 5
<212> TYPE: PRT
<213> ORGANISM: Homo sapiens

<400> SEQUENCE: 25

Tyr Gly Gly Phe Met
1               5

<210> SEQ ID NO 26
<211> LENGTH: 22
<212> TYPE: PRT
<213> ORGANISM: Homo sapiens

<400> SEQUENCE: 26

Tyr Gly Gly Phe Met Arg Arg Val Gly Arg Pro Glu Trp Trp Met Asp
1               5                   10                  15

Tyr Gln Lys Arg Tyr Gly
            20

<210> SEQ ID NO 27
<211> LENGTH: 17
<212> TYPE: PRT
<213> ORGANISM: Homo sapiens

<400> SEQUENCE: 27

Phe Gly Gly Phe Thr Gly Ala Arg Lys Ser Ala Arg Lys Leu Ala Asn
1               5                   10                  15

Gln
```

```
<210> SEQ ID NO 28
<211> LENGTH: 13
<212> TYPE: PRT
<213> ORGANISM: Homo sapiens
<220> FEATURE:
<221> NAME/KEY: SITE
<222> LOCATION: (13)..(13)
<223> OTHER INFORMATION: NH2 substituted

<400> SEQUENCE: 28

Phe Gly Gly Phe Thr Gly Ala Arg Lys Ser Ala Arg Lys
1               5                   10

<210> SEQ ID NO 29
<211> LENGTH: 4
<212> TYPE: PRT
<213> ORGANISM: Homo sapiens
<220> FEATURE:
<221> NAME/KEY: SITE
<222> LOCATION: (4)..(4)
<223> OTHER INFORMATION: NH2 substituted

<400> SEQUENCE: 29

Tyr Pro Trp Phe
1

<210> SEQ ID NO 30
<211> LENGTH: 4
<212> TYPE: PRT
<213> ORGANISM: Homo sapiens
<220> FEATURE:
<221> NAME/KEY: SITE
<222> LOCATION: (4)..(4)
<223> OTHER INFORMATION: NH2 substituted

<400> SEQUENCE: 30

Tyr Pro Phe Phe
1

<210> SEQ ID NO 31
<211> LENGTH: 32
<212> TYPE: PRT
<213> ORGANISM: Homo sapiens

<400> SEQUENCE: 31

Tyr Gly Gly Phe Met Thr Ser Glu Lys Ser Gln Thr Pro Leu Val Thr
1               5                   10                  15

Leu Phe Lys Asn Ala Ile Ile Ile Lys Asn Ala Tyr Lys Lys Gly Glu
            20                  25                  30

<210> SEQ ID NO 32
<211> LENGTH: 8
<212> TYPE: PRT
<213> ORGANISM: Artificial Sequence
<220> FEATURE:
<223> OTHER INFORMATION: peptide 7

<400> SEQUENCE: 32

Tyr Gly Gly Phe Met Arg Arg Val
1               5

<210> SEQ ID NO 33
<211> LENGTH: 8
<212> TYPE: PRT
<213> ORGANISM: Artificial Sequence
<220> FEATURE:
<223> OTHER INFORMATION: peptide 8
```

```
<400> SEQUENCE: 33

Lys Gly Gly Phe Met Arg Arg Val
1               5

<210> SEQ ID NO 34
<211> LENGTH: 8
<212> TYPE: PRT
<213> ORGANISM: Artificial Sequence
<220> FEATURE:
<223> OTHER INFORMATION: peptide 9

<400> SEQUENCE: 34

Ala Gly Gly Phe Met Arg Arg Val
1               5

<210> SEQ ID NO 35
<211> LENGTH: 8
<212> TYPE: PRT
<213> ORGANISM: Artificial Sequence
<220> FEATURE:
<223> OTHER INFORMATION: peptide 10 - mother peptide

<400> SEQUENCE: 35

Phe Gly Gly Phe Met Arg Arg Val
1               5

<210> SEQ ID NO 36
<211> LENGTH: 8
<212> TYPE: PRT
<213> ORGANISM: Artificial Sequence
<220> FEATURE:
<223> OTHER INFORMATION: peptide 11

<400> SEQUENCE: 36

Asn Gly Gly Phe Met Arg Arg Val
1               5

<210> SEQ ID NO 37
<211> LENGTH: 8
<212> TYPE: PRT
<213> ORGANISM: Artificial Sequence
<220> FEATURE:
<223> OTHER INFORMATION: peptide 12

<400> SEQUENCE: 37

Leu Gly Gly Phe Met Arg Arg Val
1               5

<210> SEQ ID NO 38
<211> LENGTH: 8
<212> TYPE: PRT
<213> ORGANISM: Artificial Sequence
<220> FEATURE:
<223> OTHER INFORMATION: peptide 13

<400> SEQUENCE: 38

Tyr Ala Gly Phe Met Arg Arg Val
1               5

<210> SEQ ID NO 39
<211> LENGTH: 8
<212> TYPE: PRT
<213> ORGANISM: Artificial Sequence
<220> FEATURE:
<223> OTHER INFORMATION: peptide 14

<400> SEQUENCE: 39
```

-continued

Tyr Ser Gly Phe Met Arg Arg Val
1               5

<210> SEQ ID NO 40
<211> LENGTH: 8
<212> TYPE: PRT
<213> ORGANISM: Artificial Sequence
<220> FEATURE:
<223> OTHER INFORMATION: peptide 15

<400> SEQUENCE: 40

Tyr Arg Gly Phe Met Arg Arg Val
1               5

<210> SEQ ID NO 41
<211> LENGTH: 8
<212> TYPE: PRT
<213> ORGANISM: Artificial Sequence
<220> FEATURE:
<223> OTHER INFORMATION: peptide 16

<400> SEQUENCE: 41

Tyr Gly Ala Phe Met Arg Arg Val
1               5

<210> SEQ ID NO 42
<211> LENGTH: 8
<212> TYPE: PRT
<213> ORGANISM: Artificial Sequence
<220> FEATURE:
<223> OTHER INFORMATION: peptide 17

<400> SEQUENCE: 42

Tyr Gly Ser Phe Met Arg Arg Val
1               5

<210> SEQ ID NO 43
<211> LENGTH: 8
<212> TYPE: PRT
<213> ORGANISM: Artificial Sequence
<220> FEATURE:
<223> OTHER INFORMATION: peptide 18

<400> SEQUENCE: 43

Tyr Gly Gly Tyr Met Arg Arg Val
1               5

<210> SEQ ID NO 44
<211> LENGTH: 8
<212> TYPE: PRT
<213> ORGANISM: Artificial Sequence
<220> FEATURE:
<223> OTHER INFORMATION: peptide 19

<400> SEQUENCE: 44

Tyr Gly Gly Trp Met Arg Arg Val
1               5

<210> SEQ ID NO 45
<211> LENGTH: 8
<212> TYPE: PRT
<213> ORGANISM: Artificial Sequence
<220> FEATURE:
<223> OTHER INFORMATION: peptide 20

<400> SEQUENCE: 45

```
Tyr Gly Gly Leu Met Arg Arg Val
1               5

<210> SEQ ID NO 46
<211> LENGTH: 8
<212> TYPE: PRT
<213> ORGANISM: Artificial Sequence
<220> FEATURE:
<223> OTHER INFORMATION: peptide 21

<400> SEQUENCE: 46

Tyr Gly Gly Ala Met Arg Arg Val
1               5

<210> SEQ ID NO 47
<211> LENGTH: 8
<212> TYPE: PRT
<213> ORGANISM: Artificial Sequence
<220> FEATURE:
<223> OTHER INFORMATION: peptide 22

<400> SEQUENCE: 47

Tyr Gly Gly Phe Leu Arg Arg Val
1               5

<210> SEQ ID NO 48
<211> LENGTH: 8
<212> TYPE: PRT
<213> ORGANISM: Artificial Sequence
<220> FEATURE:
<223> OTHER INFORMATION: peptide 23

<400> SEQUENCE: 48

Tyr Gly Gly Phe Ala Arg Arg Val
1               5

<210> SEQ ID NO 49
<211> LENGTH: 8
<212> TYPE: PRT
<213> ORGANISM: Artificial Sequence
<220> FEATURE:
<223> OTHER INFORMATION: peptide 24

<400> SEQUENCE: 49

Tyr Gly Gly Phe Lys Arg Arg Val
1               5

<210> SEQ ID NO 50
<211> LENGTH: 8
<212> TYPE: PRT
<213> ORGANISM: Artificial Sequence
<220> FEATURE:
<223> OTHER INFORMATION: peptide 25

<400> SEQUENCE: 50

Tyr Gly Gly Phe Gln Arg Arg Val
1               5

<210> SEQ ID NO 51
<211> LENGTH: 8
<212> TYPE: PRT
<213> ORGANISM: Artificial Sequence
<220> FEATURE:
<223> OTHER INFORMATION: peptide 26

<400> SEQUENCE: 51

Tyr Gly Gly Phe Phe Arg Arg Val
```

-continued

```
1               5

<210> SEQ ID NO 52
<211> LENGTH: 8
<212> TYPE: PRT
<213> ORGANISM: Artificial Sequence
<220> FEATURE:
<223> OTHER INFORMATION: peptide 27

<400> SEQUENCE: 52

Tyr Gly Gly Phe Asn Arg Arg Val
1               5

<210> SEQ ID NO 53
<211> LENGTH: 8
<212> TYPE: PRT
<213> ORGANISM: Artificial Sequence
<220> FEATURE:
<223> OTHER INFORMATION: peptide 28

<400> SEQUENCE: 53

Tyr Gly Gly Phe Met Ala Arg Val
1               5

<210> SEQ ID NO 54
<211> LENGTH: 8
<212> TYPE: PRT
<213> ORGANISM: Artificial Sequence
<220> FEATURE:
<223> OTHER INFORMATION: peptide 29

<400> SEQUENCE: 54

Tyr Gly Gly Phe Met Lys Arg Val
1               5

<210> SEQ ID NO 55
<211> LENGTH: 8
<212> TYPE: PRT
<213> ORGANISM: Artificial Sequence
<220> FEATURE:
<223> OTHER INFORMATION: peptide 30

<400> SEQUENCE: 55

Tyr Gly Gly Phe Met Arg Ala Val
1               5

<210> SEQ ID NO 56
<211> LENGTH: 8
<212> TYPE: PRT
<213> ORGANISM: Artificial Sequence
<220> FEATURE:
<223> OTHER INFORMATION: peptide 31

<400> SEQUENCE: 56

Tyr Gly Gly Phe Met Arg Lys Val
1               5

<210> SEQ ID NO 57
<211> LENGTH: 8
<212> TYPE: PRT
<213> ORGANISM: Artificial Sequence
<220> FEATURE:
<223> OTHER INFORMATION: peptide 32

<400> SEQUENCE: 57

Tyr Gly Gly Phe Met Arg Arg Leu
1               5
```

```
<210> SEQ ID NO 58
<211> LENGTH: 8
<212> TYPE: PRT
<213> ORGANISM: Artificial Sequence
<220> FEATURE:
<223> OTHER INFORMATION: peptide 33

<400> SEQUENCE: 58

Tyr Gly Gly Phe Met Arg Arg Ile
1               5

<210> SEQ ID NO 59
<211> LENGTH: 8
<212> TYPE: PRT
<213> ORGANISM: Artificial Sequence
<220> FEATURE:
<223> OTHER INFORMATION: peptide 34

<400> SEQUENCE: 59

Tyr Gly Gly Phe Met Arg Arg Ala
1               5

<210> SEQ ID NO 60
<211> LENGTH: 8
<212> TYPE: PRT
<213> ORGANISM: Artificial Sequence
<220> FEATURE:
<223> OTHER INFORMATION: peptide 35

<400> SEQUENCE: 60

Tyr Gly Gly Phe Met Arg Arg Phe
1               5

<210> SEQ ID NO 61
<211> LENGTH: 8
<212> TYPE: PRT
<213> ORGANISM: Artificial Sequence
<220> FEATURE:
<223> OTHER INFORMATION: peptide 36

<400> SEQUENCE: 61

Tyr Gly Gly Phe Met Arg Arg Lys
1               5

<210> SEQ ID NO 62
<211> LENGTH: 8
<212> TYPE: PRT
<213> ORGANISM: Artificial Sequence
<220> FEATURE:
<223> OTHER INFORMATION: peptide 37

<400> SEQUENCE: 62

Tyr Gly Gly Phe Met Arg Arg Gln
1               5

<210> SEQ ID NO 63
<211> LENGTH: 7
<212> TYPE: PRT
<213> ORGANISM: Artificial Sequence
<220> FEATURE:
<223> OTHER INFORMATION: peptide 38

<400> SEQUENCE: 63

Gly Gly Phe Met Arg Arg Val
1               5
```

<210> SEQ ID NO 64
<211> LENGTH: 9
<212> TYPE: PRT
<213> ORGANISM: Artificial Sequence
<220> FEATURE:
<223> OTHER INFORMATION: peptide 39

<400> SEQUENCE: 64

Ala Tyr Gly Gly Phe Met Arg Arg Val
1               5

<210> SEQ ID NO 65
<211> LENGTH: 9
<212> TYPE: PRT
<213> ORGANISM: Artificial Sequence
<220> FEATURE:
<223> OTHER INFORMATION: peptide 40

<400> SEQUENCE: 65

Tyr Gly Gly Phe Met Arg Arg Val Ala
1               5

<210> SEQ ID NO 66
<211> LENGTH: 9
<212> TYPE: PRT
<213> ORGANISM: Artificial Sequence
<220> FEATURE:
<223> OTHER INFORMATION: peptide 41

<400> SEQUENCE: 66

Tyr Gly Gly Phe Met Arg Arg Val Arg
1               5

<210> SEQ ID NO 67
<211> LENGTH: 9
<212> TYPE: PRT
<213> ORGANISM: Artificial Sequence
<220> FEATURE:
<223> OTHER INFORMATION: peptide 42

<400> SEQUENCE: 67

Tyr Gly Gly Phe Met Arg Arg Val Cys
1               5

<210> SEQ ID NO 68
<211> LENGTH: 8
<212> TYPE: PRT
<213> ORGANISM: Artificial Sequence
<220> FEATURE:
<223> OTHER INFORMATION: peptide 43

<400> SEQUENCE: 68

Phe Gly Gly Trp Met Arg Arg Val
1               5

<210> SEQ ID NO 69
<211> LENGTH: 8
<212> TYPE: PRT
<213> ORGANISM: Artificial Sequence
<220> FEATURE:
<223> OTHER INFORMATION: peptide 44

<400> SEQUENCE: 69

Phe Gly Gly Phe Met Arg Arg Phe
1               5

-continued

```
<210> SEQ ID NO 70
<211> LENGTH: 9
<212> TYPE: PRT
<213> ORGANISM: Artificial Sequence
<220> FEATURE:
<223> OTHER INFORMATION: peptide 45

<400> SEQUENCE: 70

Phe Gly Gly Phe Met Arg Arg Phe Arg
1               5

<210> SEQ ID NO 71
<211> LENGTH: 9
<212> TYPE: PRT
<213> ORGANISM: Artificial Sequence
<220> FEATURE:
<223> OTHER INFORMATION: peptide 46

<400> SEQUENCE: 71

Phe Gly Gly Trp Met Arg Arg Phe Arg
1               5

<210> SEQ ID NO 72
<211> LENGTH: 8
<212> TYPE: PRT
<213> ORGANISM: Artificial Sequence
<220> FEATURE:
<223> OTHER INFORMATION: peptide 47

<400> SEQUENCE: 72

Phe Gly Gly Trp Met Arg Arg Phe
1               5

<210> SEQ ID NO 73
<211> LENGTH: 4
<212> TYPE: PRT
<213> ORGANISM: Homo sapiens

<400> SEQUENCE: 73

Gly Arg Pro Glu
1

<210> SEQ ID NO 74
<211> LENGTH: 5
<212> TYPE: PRT
<213> ORGANISM: Homo sapiens

<400> SEQUENCE: 74

Gly Arg Pro Glu Trp
1               5

<210> SEQ ID NO 75
<211> LENGTH: 6
<212> TYPE: PRT
<213> ORGANISM: Homo sapiens

<400> SEQUENCE: 75

Gly Arg Pro Glu Trp Trp
1               5
```

-continued

```
<210> SEQ ID NO 76
<211> LENGTH: 7
<212> TYPE: PRT
<213> ORGANISM: Homo sapiens

<400> SEQUENCE: 76

Gly Arg Pro Glu Trp Trp Met
1               5
```

SELECTIVE ACKR3 MODULATORS AND USES THEREOF

CROSS-REFERENCE TO RELATED APPLICATIONS

This patent application is a U.S. National Phase application of International Patent Application No. PCT/EP2020/061981, filed Apr. 30, 2020, which claims the benefit of European Patent Application No. 19172560.5, filed May 3, 2019, each of which is incorporated by reference herein in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 16,971 byte ASCII (text) file named "757834_ST25.txt," dated Nov. 2, 2021.

FIELD

The invention is broadly in the medical field, and provides novel atypical chemokine receptor 3 (ACKR3) modulating molecules useful in different fields including diagnosis and therapy, both as such and as fusion proteins with other agents, and further provides methods and uses of said ACKR3 modulating molecules.

BACKGROUND

Opioid receptors are G protein-coupled receptors (GPCRs) expressed by the central nervous system and immune cells that play a central role in modulating analgesia, reward processing, as well as stress, anxiety or depression. The family of opioid receptors consists of three classical receptors: mu ($\mu$ or MOR), delta ($\delta$ or DOR), kappa ($\kappa$ or KOR); and the non-classical nociceptin receptor (NOP, or orphanin FQ receptor).

All endogenous opioid peptides derive from proteolytic cleavage of large protein precursors and are mainly produced in the central nervous system (CNS), but also in the adrenal and pituitary gland and by several types of immune cells. With some exceptions, these ligands trigger downstream signalling responses via G proteins, which is followed by $\beta$-arrestin recruitment, leading to receptor desensitization and internalization. Opioid receptors can also be modulated by non-peptide opioids such as morphine, fentanyl or naloxone. Opioid receptors represent attractive targets for pharmaceuticals and opioid receptor modulators remain the most widely used analgesics in the clinic. However, the use of these medicaments is often associated with tolerance, dependence and various adverse effects (e.g. respiratory depression) or misuse.

Opioid receptor expression, signalling and desensitization are furthermore influenced by their interactions with other GPCRs, notably chemokine receptors. Chemokine receptors bind to chemokines, which are small (8-14 kDa) secreted chemo-attractant cytokines, chemokines, regulating cellular processes like migration, adhesion and growth and thereby playing a crucial role in inflammatory and developmental processes. To date, nearly 50 chemokines and 20 classical receptors have been identified in humans. Similar to opioid receptor-ligand network, many chemokine receptors recognize multiple chemokines, and, vice versa, many chemokines activate more than one receptor. Recently, a new family, called atypical chemokine receptors (ACKRs), has emerged as small subgroup of chemokine receptors. ACKRs bind chemokines without triggering G protein signalling but instead participate in chemotactic events by transporting or capturing the chemokines or internalizing and degrading the ligands in order to resolve inflammatory processes or to shape appropriate chemokine gradients.

ACKR3, formerly CXCR7, is expressed in various cells such as B and T lymphocytes, neurons and endothelial cells and plays a crucial role in many processes including cardiovascular and neuronal development as well as in migration and homing of hematopoietic stem/progenitor cells. An increasing number of studies point to the involvement of ACKR3 in cardiovascular diseases and in many cancers. ACKR3 is expressed in various cancer cell types as well as on tumour-associated vasculature and accumulating evidence demonstrates its involvement in metastasis development. ACKR3 was also shown to be upregulated upon infection by several cancer-inducing viruses including HHV-8, EBV, HTLV-1 and to play an important role in cell transformation and proliferation. Due to its unusual biology, it has recently been classified as an atypical chemokine receptor. Indeed, ACKR3 binds two endogenous chemokines, C—X—C motif chemokine 12 (CXCL12) and C—X—C motif chemokine 11 (CXCL11), which are also recognized by C—X—C motif chemokine receptor 4 (CXCR4) and C—X—C motif chemokine receptor 3 (CXCR3), respectively but unlike conventional chemokine receptors, ACKR3 does not activate the canonical G protein pathways and is proposed to trigger $\beta$-arrestin-dependent signalling. In addition, through its continuous cycling between the plasma membrane and endosomal compartments and its capacity to efficiently internalise and degrade chemokines, ACKR3 functions as a scavenger receptor regulating the availability of CXCL12 and CXCL11 for CXCR4 and CXCR3. Moreover, ACKR3 was proposed to modulate the activity of CXCR4 by forming heterodimers or competing for intracellular effector proteins involved in signal transduction.

In view of the above, there is an urgent need to explore new ways to modulate disorders involving ACKR3.

SUMMARY

Present inventors discovered that the atypical chemokine receptor ACKR3 binds a large array of endogenous opioid peptides found in the central nervous system (CNS) and immune cells, including those from the enkephalin, dynorphin and nociceptin family. This broad-spectrum selectivity is atypical and unique among the opioid receptors. Furthermore, present inventors found that ACKR3, in contrast to the known opioid receptors and to what was proposed by Ikeda et al. (Ikeda et al., 2013, Modulation of circadian glucocorticoid oscillation through adrenal opioid-CXCR7 signaling alters emotional behavior, Cell. 155(6): 1323-1336), is unable to activate downstream signalling pathways, for instance via G proteins or $\beta$-arrestins, in response to endogenous opioid peptides, is present in different cellular compartments and acts as a scavenger, regulating their local and/or systemic concentrations and thus availability for the classical opioid receptors.

Present inventors found that ACKR3 can be modulated to alter levels of endogenous opioid peptides in the treatment of disorders linked with endogenous opioid peptide dysregulation, like distress dysfunction diseases or conditions such as depression or chronic pain, with a potentially improved safety profile.

To this end, present inventors developed selective ACKR3 modulators. More particularly, these selective ACKR3 modulators are peptides having a consensus sequence $FGGX_1MRRX_2$(SEQ ID NO: 1), wherein $X_1$ is F or W, $X_2$ is K, V or F, preferably having a length of at most 15 amino acids, which have high affinity and selectivity for ACKR3, and no modulating (e.g. agonistic or antagonistic) activity on any other type of receptor tested. Furthermore, the novel peptides having high affinity and selectivity for ACKR3 can act as ACKR3 agonists and can induce β-arrestin-1 and/or β-arrestin-2 to ACKR3. Additionally, when the peptides as taught herein have a length of at most 15 amino acids, these peptides take advantage of low production costs, which is very important for remaining competitive and allowing access for most patients.

In view of the above, a first aspect provides a selective ACKR3 modulating peptide comprising amino acid sequence $FGGX_1MRRX_2$(SEQ ID NO: 1), wherein $X_1$ is F or W; $X_2$ is K, V or F; and the peptide has a length of at most 15 amino acids.

In particular embodiments, $X_1$ is F.

In particular embodiments, $X_2$ is K.

In particular embodiments, the peptide comprises amino acid sequence $FGGX_1MRRX_2X_3$(SEQ ID NO: 2), wherein $X_3$ can be any amino acid, preferably wherein $X_3$ is R or A.

In particular embodiments, the peptide comprises an amino acid sequence selected from the group consisting of FGGFMRRK (SEQ ID NO: 3), FGGFMRRKR (SEQ ID NO: 4), FGGFMRRVR (SEQ ID NO: 5), and FGGWMRRK (SEQ ID NO: 6), preferably wherein the peptide comprises amino acid sequence FGGFMRRK (SEQ ID NO: 3), preferably wherein the C-terminus of the peptide is $NH_2$-substituted.

A further aspect provides a fusion protein comprising the peptide as taught herein.

A further aspect provides a nucleic acid encoding for the peptide as taught herein or the fusion protein as taught herein.

A further aspect provides a nucleic acid expression cassette comprising the nucleic acid as taught herein, operably linked to a promoter and/or transcriptional and translational regulatory signals.

A further aspect provides a vector comprising the nucleic acid as taught herein or the nucleic acid expression cassette as taught herein, such as a viral vector.

A further aspect provides a pharmaceutical composition comprising the peptide as taught herein, the fusion peptide as taught herein, the nucleic acid as taught herein, the nucleic acid expression cassette as taught herein or the vector as taught herein, and optionally a pharmaceutically acceptable carrier.

A further aspect provides the peptide as taught herein, the fusion protein as taught herein, the nucleic acid as taught herein, the nucleic acid expression cassette as taught herein, the vector as taught herein or the pharmaceutical composition as taught herein, for use as a medicament, preferably for use in the treatment of a disease or condition selected from the group consisting of distress dysfunction diseases or conditions, cancers, atherosclerotic vascular disease, cardiovascular diseases, fibrosis (e.g. cardiac fibrosis), inflammatory or autoimmune diseases and conditions, conditions of excessive or abnormal vascularization (e.g. wound healing and HIV infectivity), stem cell differentiation and mobilization disorders, brain and neuronal dysfunctions (e.g.

Alzheimer's disease, multiple sclerosis and demyelinating diseases), kidney dysfunction, renal dysfunction, preeclampsia and obesity in a subject.

A further aspect provides a method for in vitro or ex vivo diagnosis, prediction, prognosis and/or monitoring of a disease or condition characterized by an aberrant level of ACKR3 polypeptide, comprising the steps of obtaining a biological sample obtained from a subject, contacting said biological sample with the peptide as taught herein, wherein said peptide is fused to a detectable label, determining the level of ACKR3 polypeptide in said biological sample by detecting said peptide, and diagnosing, predicting, prognosing and/or monitoring the disease or condition based on the level of ACKR3 polypeptide.

A further aspect provides a therapeutic or prophylactic agent for use in the treatment of a distress dysfunction disease or condition in a subject, wherein said therapeutic or prophylactic agent is capable of modulating β-arrestin-1 and/or β-arrestin-2 recruitment to the atypical chemokine receptor 3 (ACKR3) polypeptide, and not to any other receptor polypeptide.

A further aspect provides an in vitro method for identifying an agent useful as a therapeutic, said method comprising determining whether a test agent is capable of inducing β-arrestin-1 and/or β-arrestin-2 recruitment to the ACKR3 polypeptide and not capable of inducing β-arrestin-1 and/or β-arrestin-2 recruitment to any other receptor polypeptide.

A further aspect provides an in vitro method for identifying an agent useful as a therapeutic, said method comprising determining whether a test agent is capable of inhibiting β-arrestin-1 and/or β-arrestin-2 recruitment to the ACKR3 polypeptide by the selective ACKR3 modulating peptide as taught herein.

A further aspect provides a kit for diagnosing, predicting, prognosing and/or monitoring a disease or condition characterized by an aberrant level of ACKR3 polypeptide in a subject, the kit comprising:

(a) the peptide as taught herein; and (b) a reference value of the level of ACKR3 polypeptide, wherein said reference value represents a known diagnosis, prediction and/or prognosis of the disease or condition characterized by an aberrant level of ACKR3 polypeptide.

Figure 1:
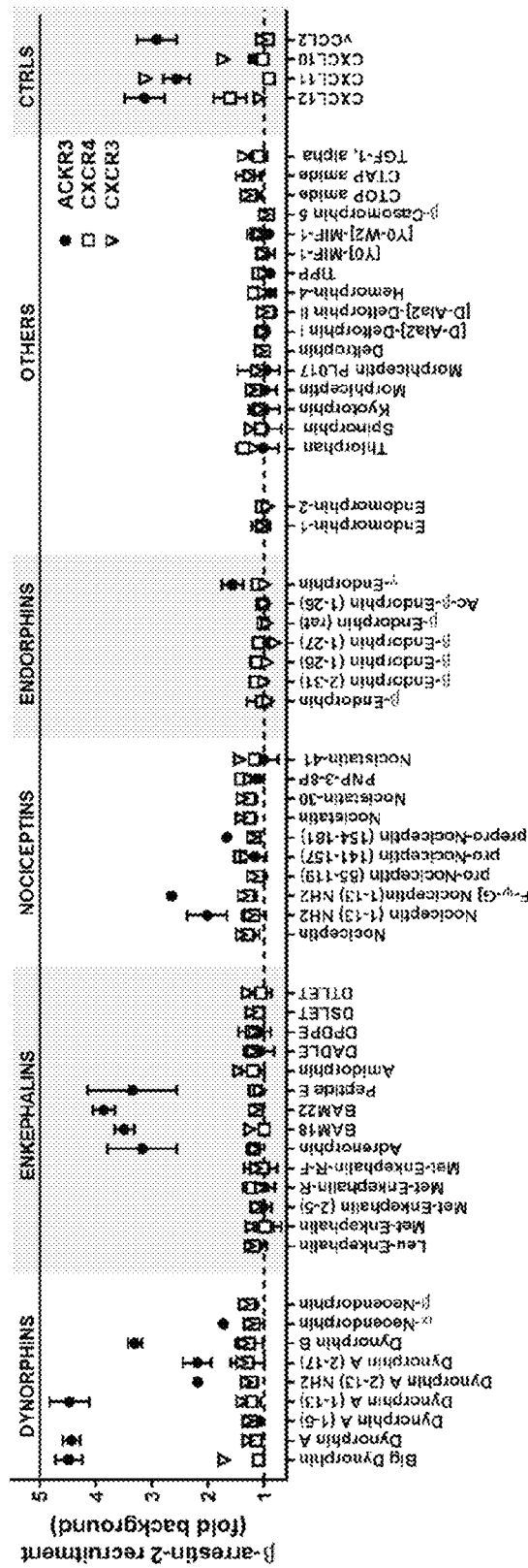
FIG. 1 Opioid peptide library screening on ACKR3, hit confirmation and comparison with classical opioid receptors. (A) The ability of 58 compounds, including natural opioid peptides from the four opioid families, variants thereof and small molecule opioid receptor modulators, to induce β-arrestin-2 recruitment to ACKR3, CXCR4 and CXCR3 in U87 cells at a concentration of 5 μM. Positive control chemokines were used at a concentration of 300 nM. Results are expressed as fold change over vehicle-treated cells and presented as mean±S.D of two replicates (B-F) Comparison of potency and efficacy of ACKR3-activating peptides in inducing β-arrestin-1 recruitment to the opioid receptors MOR (B), DOR (C), KOR (D), NOP (E) and ACKR3 (F) in U87 cells. Results are expressed as percentage of indicated agonist response. (G) Binding competition of ACKR3-activating peptides with Alexa Fluor 647-labelled CXCL12 (5 nM) on U87-ACKR3 cells determined by flow cytometry. (H) Sequences of opioid peptides representative of the four families and the potency and efficacy of said opioid peptides in inducing β-arrestin-1 recruitment to ACKR3 or competing with Alexa Fluor 647-labelled CXCL12. Results from B—H are presented as mean±S.E.M $(n \geqslant 3)$.
Figure 1:
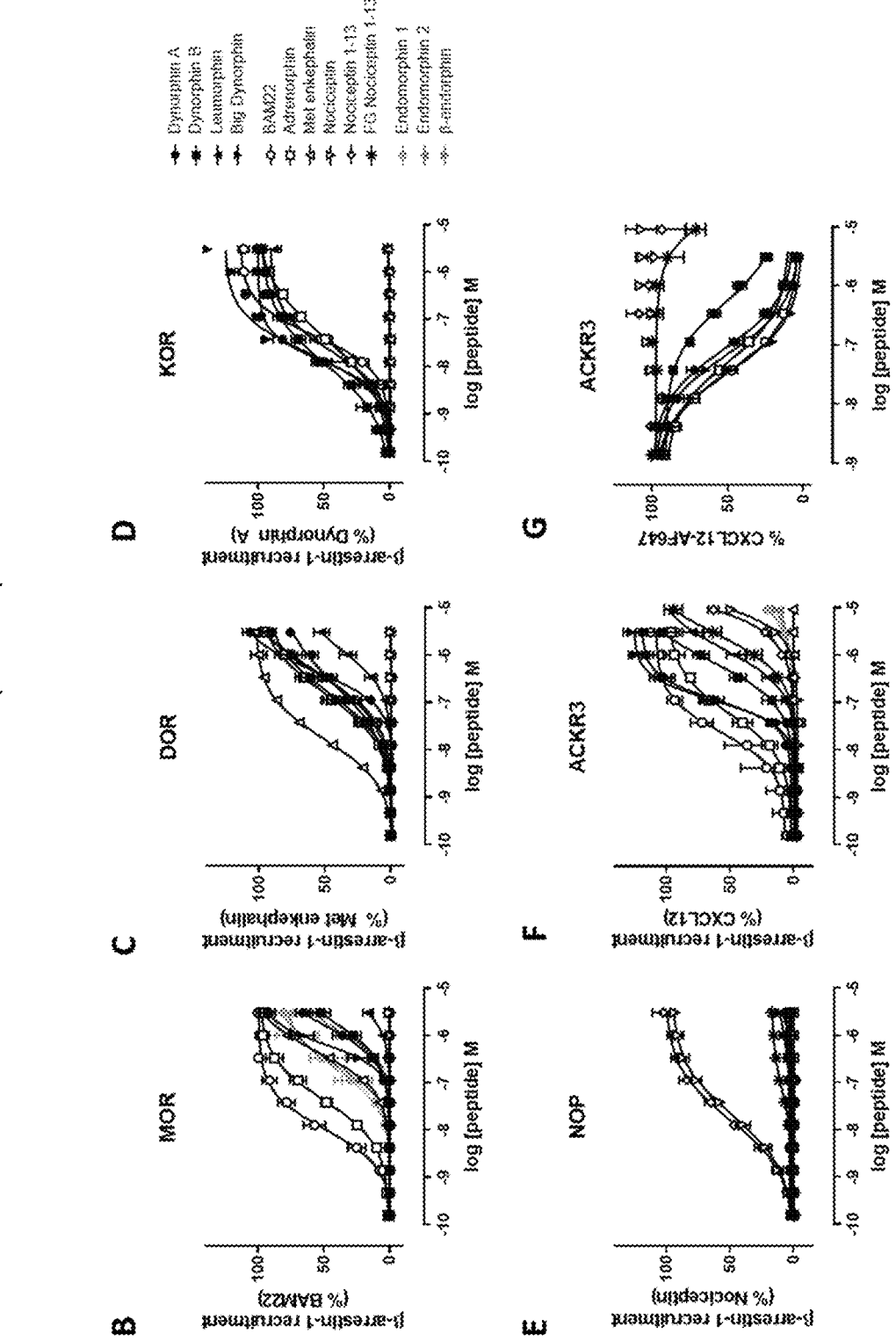

Opioid peptide-induced receptor-arrestin delivery to endosomes monitored by β-galactosidase complementation assay in U2OS cells stably expressing ACKR3. (E-G) Kinetics of opioid peptide-induced internalization of ACKR3 and classical opioid receptors monitored by HiBiT technology (E and G) and flow cytometry (F). (E) U87 cells expressing receptors N-terminally tagged with HiBiT were stimulated with opioid peptides, including dynorphin A, dynorphin B, big dynorphin, dynorphin A 1-13, adrenorphin, BAM22, met enkaphalin, endomorphin 1, endomorphin 2 and beta-endorphin (1 μM) or CXCL12 (300 nM) for indicated times and remaining membrane receptors were quantified with soluble LgBiT protein. (F) ACKR3 and KOR internalization and recycling profiles in U87 cells after ligand stimulation (1 μM for opioid peptides including dynorphin A, dynorphin B, big dynorphin, dynorphin A 1-13, adrenorphin, BAM22, met-enkaphalin, nociception, nociception 1-13 and F-G nociception 1-13, 300 nM for CXCL12) followed by acid wash monitored by flow cytometry. (G) Effect of bafilomycin A1 (1.5 μM) on endosomal trafficking/cycling of ACKR3 and KOR following 180-minute stimulation by various opioid peptides (1 μM) monitored by HiBiT technology. Results are presented as the mean (A) or the mean±S.E.M. (B-G) (n≥3). * p<0.05,  p<0.01, * p<0.001 by one-way ANOVA with Bonferroni correction (B), by two-way ANOVA: interaction between cell line and ligand treatment with Tukey's post hoc test (C), and by two-tailed unpaired t-test (G).

Figure 7:
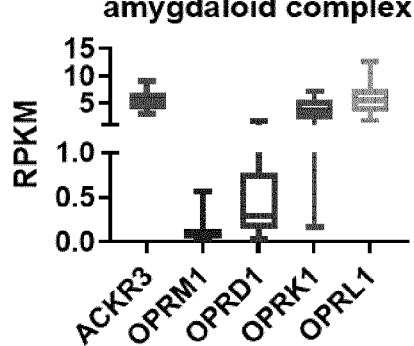
Figure 7:
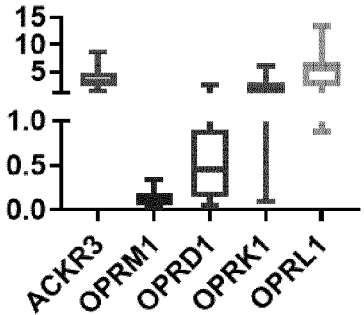
Figure 7:
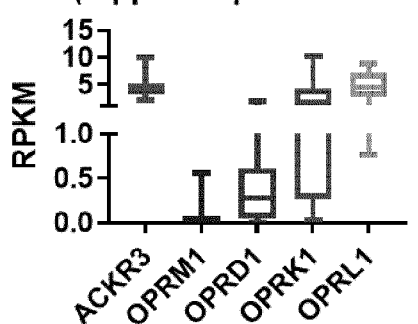
Figure 7:
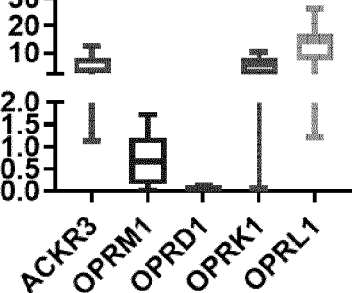
Figure 7:
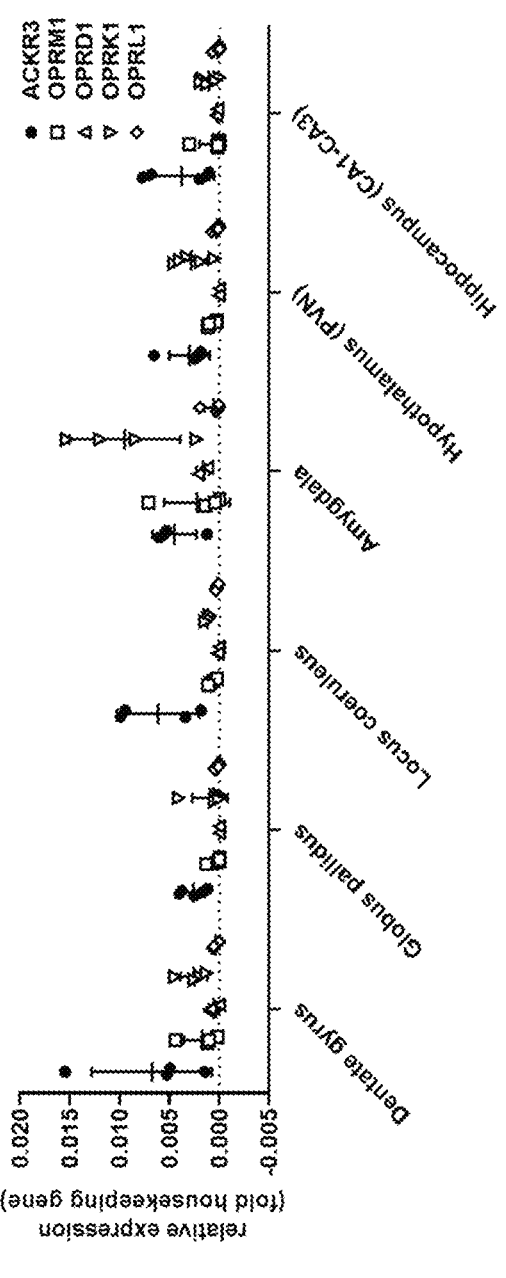
Figure 7:
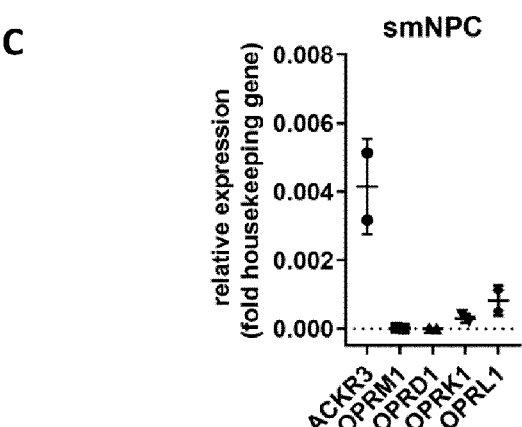
Figure 7:
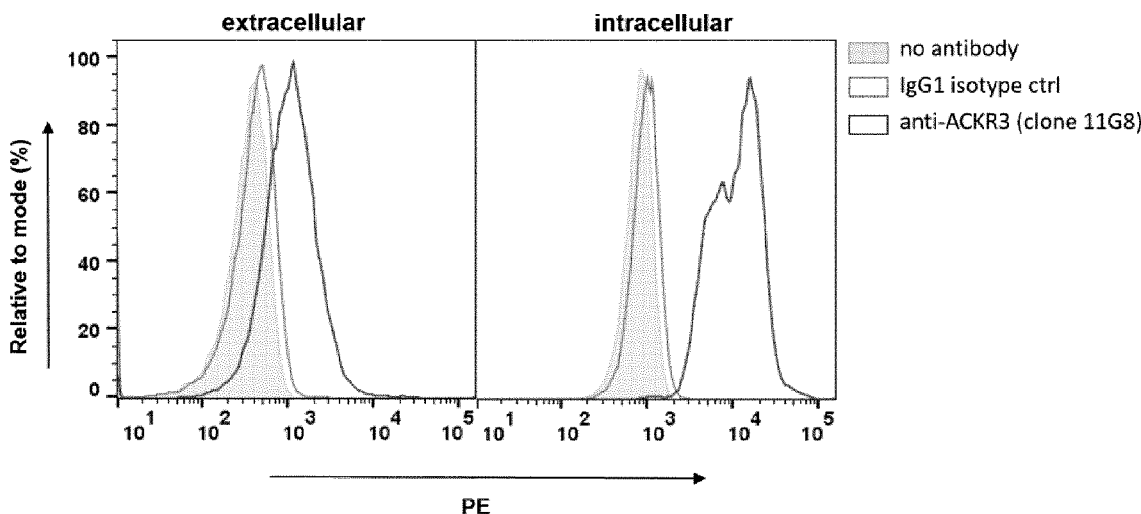
Figure 7:
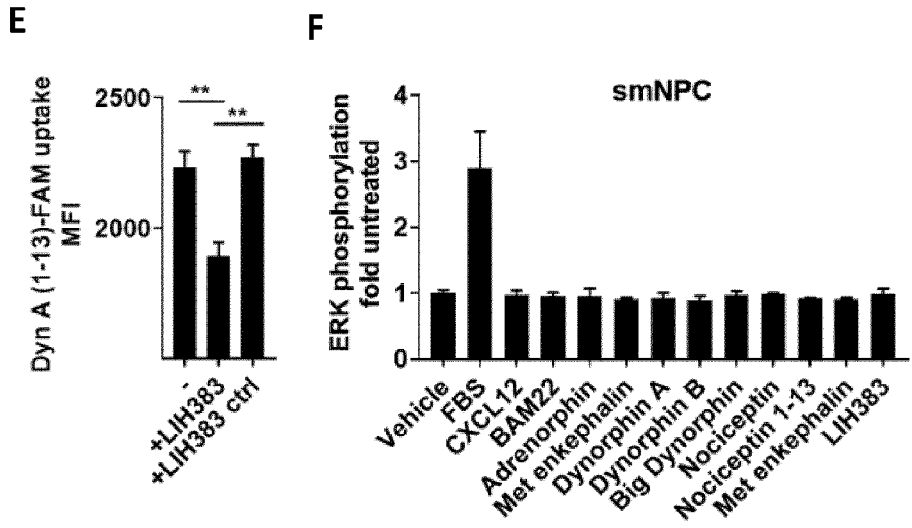
Figure 7:
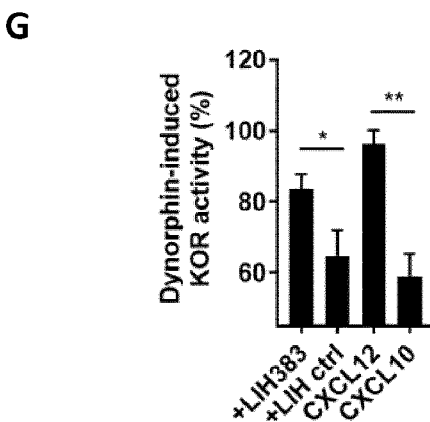
Figure 7:
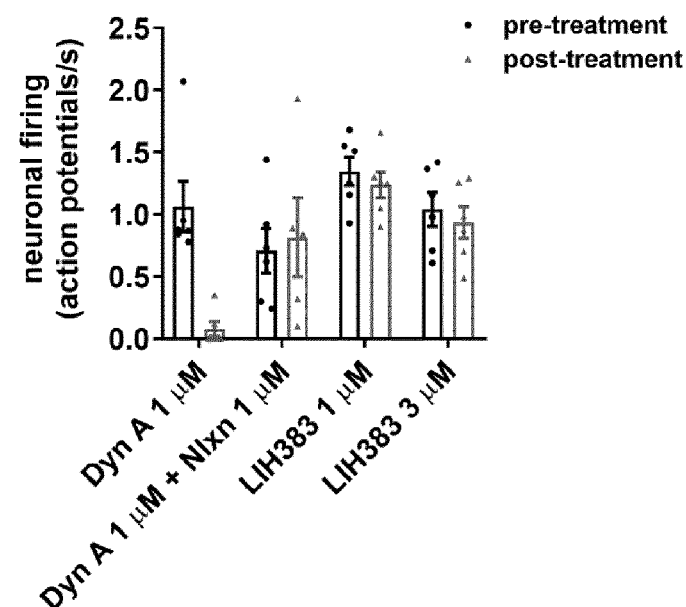
Figure 7:
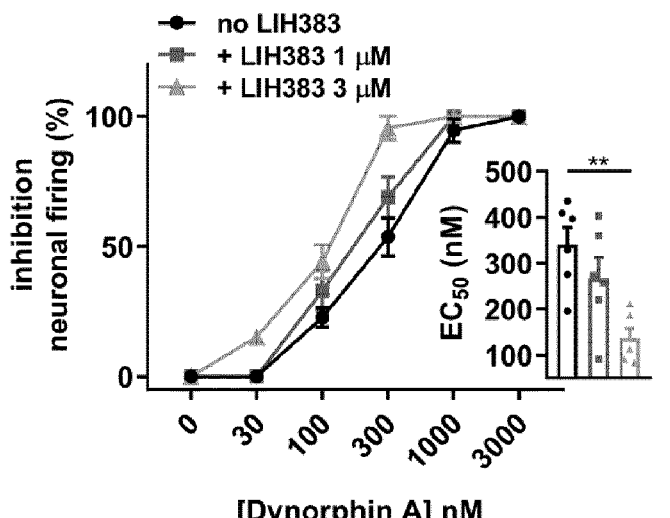

FIG. 7 ACKR3-mediated regulation of opioid peptide availability for classical receptors in neural progenitor cells and brain opioid centres. (A-C) Relative gene expression of ACKR3 and classical opioid receptors in smNPCs and different brain regions corresponding to centres important for opioid peptide activity. (A) RNA-Seq RPKM (reads per kilobase per million) values from an open-source database (brainspan.org) containing data from 16-22 donors. (B and C) mRNA expression determined by qPCR on five human adult brains (B) or two smNPC samples (C) normalised to the arithmetic mean of PPIA and GAPDH as stable housekeeping genes. (D) Extracellular and intracellular expression of ACKR3 monitored by flow cytometry using ACKR3-specific mAb antibody (11G8) or a matched isotype control (MG1-45) and a PE-conjugated secondary antibody in comparison to unstained cells. (E) Uptake of fluorescently labelled dynorphin A (1-13) by smNPCs evaluated by imaging flow cytometry. smNPCs pre-treated with LIH383 or LIH383ctrl (3 μM) for 15 minutes were incubated for 40 minutes at 37° C. with 250 nM (FAM)-labelled dynorphin A (1-13) and analysed by imaging flow cytometry. Results represent mean±S.E.M (n ≥ 3) (F) SRE (ERK1/2) signalling cascade activation in smNPCs in response to various opioid peptides (500 nM) or 10% FBS as positive control. Results represent the mean±S.E.M (n ≥ 3) (G) ACKR3-mediated depletion of ≥ extracellular dynorphin A monitored by the ability to activate KOR. smNPCs, pre-treated for 15 minutes with LIH383, LIH ctrl (1.5 μM), CXCL12 or CXCL10 (300 nM), were incubated for 4 hours with dynorphin A (3 μM). The activity of dynorphin A remaining in the cell supernatants was probed on U87 cells expressing SmBiT-tagged KOR and LgBiT-tagged mini Gi. Representative 30× supernatant dilution is shown. Results are expressed as mean±S.E.M (n ≥ 3). (H and I) Ex vivo rat ≥ locus coeruleus inhibition of neuron depolarisation induced by LIH383 alone, dynorphin A in the presence or absence of naloxone (H) or increasing concentrations of dynorphin A in the presence or absence of LIH383 (I). Data and the $EC_{50}$ values (inset) are presented as mean±S.E.M and are based on six independent depolarization experiments for each condition. *p<0.05, ** p<0.01 by one-way ANOVA with Bonferroni correction (E and G) and Kruskal-Wallis with Dunn's test (I).

DESCRIPTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The discussion of the background to the invention herein is included to explain the context of the invention. This is not to be taken as an admission that any of the material referred to was published, known, or part of the common general knowledge in any country as of the priority date of any of the claims.

Throughout this disclosure, various publications, patents and published patent specifications are referenced by an identifying citation. All documents cited in the present specification are hereby incorporated by reference in their entirety. In particular, the teachings or sections of such documents herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

In the following passages, different aspects or embodiments of the invention are defined in more detail. Each aspect or embodiment so defined may be combined with any other aspect(s) or embodiment(s) unless clearly indicated to the contrary. In particular, any feature indicated as being preferred or advantageous may be combined with any other feature or features indicated as being preferred or advantageous.

Reference throughout this specification to "one embodiment", "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

Present inventors identified the atypical chemokine receptor ACKR3 (also known as CXCR7) as a new key regulator of the opioid system.

More particularly, present inventors found that ACKR3 is abundantly expressed in the brain together with classical opioid receptors and demonstrate that in addition to BAM22 (Ikeda et al., 2013, Modulation of circadian glucocorticoid oscillation through adrenal opioid-CXCR7 signaling alters emotional behaviour, Cell. 155(6): 1323-1336), ACKR3 binds a large array of other endogenous opioid peptides found in the central nervous system (CNS) and immune cells, including those from the enkephalin, dynorphin and nociceptin family. This broad-spectrum selectivity is atypical and unique among the opioid receptors. Furthermore, present inventors found that ACKR3, in contrast to the known opioid receptors and to what was proposed by Ikeda et al. (Ikeda et al., 2013, Modulation of circadian glucocorticoid oscillation through adrenal opioid-CXCR7 signaling alters emotional behavior, Cell. 155(6): 1323-1336), is unable to activate downstream signalling pathways, for instance via G proteins or β-arrestins, in response to endogenous opioid peptides, is present in different cellular compartments and acts as a scavenger, regulating their local and/or systemic concentrations and thus availability for the classical opioid receptors.

Present inventors found that ACKR3 acts as a scavenger towards this family of neuromodulators, regulating their availability for signalling opioid receptors. Thus, ACKR3 acts as a new broad-spectrum receptor for opioid peptides. More particularly, present inventors showed in a rat ex-vivo model that blocking ACKR3 increased the availability and signalling induced by opioid peptides through classical receptors. Present inventors also have shown that inhibition of neuron firing cannot be achieved by specific activation of ACKR3, but only through activation of classical opioid receptors, whereas neutralisation of ACKR3 scavenging capacity clearly demonstrates an improved potency of dynorphin A towards its classical receptors. Opioid peptide scavenging was further confirmed in neural precursor cells (smNPC) and U87 cells.

Accordingly, ACKR3 can be used to modulate and/or restore normal levels of endogenous opioid peptides in the treatment of disorders linked with endogenous opioid peptide dysregulation, like distress dysfunction diseases or conditions such as depression or chronic pain, with a potentially improved safety profile. To this end, present inventors developed peptides having a consensus sequence FGGX$_1$MRRX$_2$(SEQ ID NO: 1), wherein X$_1$ is F or W, X$_2$ is K, V or F, preferably having a length of at most 15 amino acids, which have high affinity and selectivity for ACKR3, and no modulating (e.g. agonistic or antagonistic) activity on the mu(μ)-type opioid receptor (MOR), delta (δ)-type opioid receptor (DOR), kappa (κ)-type opioid receptor (KOR) and non-classical nociceptin receptor (NOP), or any of C—C chemokine receptor type 1 (CCR1), C—C chemokine receptor type 2A (CCR2A), C—C chemokine receptor type 2B (CCR2B), C—C chemokine receptor type 3 (CCR3), C—C chemokine receptor type 4 (CCR4), C—C chemokine receptor type 5 (CCR5), C—C chemokine receptor type 6 (CCR6), C—C chemokine receptor type 7 (CCR7), C—C chemokine receptor type 8 (CCR8), C—C chemokine receptor type 9 (CCR9), C—C chemokine receptor type 10 (CCR10), C—X—C motif chemokine receptor 1 (CXCR1), C—X—C motif chemokine receptor 2 (CXCR2), C—X—C motif chemokine receptor 3A (CXCR3A), C—X—C motif chemokine receptor 3B (CXCR3B), C—X—C motif chemokine receptor 4 (CXCR4), C—X—C motif chemokine receptor 5 (CXCR5), C—X—C motif chemokine receptor 6 (CXCR6), C—X—C motif chemokine receptor 8 (CXCR8), X—C motif chemokine receptor 1 (XCR1), C—X3-C motif chemokine receptor 1 (CX3CR1), atypical chemokine receptor 1 (ACKR1), atypical chemokine receptor 2 (ACKR2) and atypical chemokine receptor 4 (ACKR4). Furthermore, the novel peptides having high affinity and selectivity for ACKR3 can act as ACKR3 agonists and can induce β-arrestin-1 and/or β-arrestin-2 recruitment to ACKR3.

Additionally, when the peptides as taught herein have a length of at most 15 amino acids, these peptides take advantage of low production costs, which is very important for remaining competitive and allowing access for most patients.

Accordingly, a first aspect provides a peptide comprising, consisting essentially of or consisting of amino acid sequence FGGX$_1$MRRX$_2$ (SEQ ID NO: 1), wherein X$_1$ is F or W, X$_2$ is K, V or F, and optionally, wherein the peptide has a length of at most 15 amino acids.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

In particular embodiments, the peptide is non-naturally occurring, e.g., not present in or isolated from nature, e.g., produced or expressed natively or endogenously by a cell or tissue and optionally isolated therefrom.

In particular embodiments, the peptide is recombinant, i.e., produced by recombinant DNA technology, and/or can be, partly or entirely, chemically or biochemically synthesised. Without limitation, a peptide can be produced recombinantly by a suitable host or host cell expression system and optionally isolated therefrom (e.g., a suitable bacterial, yeast, fungal, plant or animal host or host cell expression system), or produced recombinantly by cell-free translation or cell-free transcription and translation, or non-biological peptide synthesis.

In particular embodiments, the peptide consists of 20 amino acids or less, 15 amino acids or less, such as 14 amino acids or less, 13 amino acids or less, 12 amino acids or less, 11 amino acids or less, preferably 10 amino acids or less, such as 9 amino acids or 8 amino acids. In particular embodiments, the peptide consists of from 8 to 20 amino acids, from 8 to 15 amino acids, from 8 to 14 amino acids, from 8 to 13 amino acids, from 8 to 12 amino acids, from 8 to 11 amino acids, from 8 to 10 amino acids, or 8 or 9 amino acids, preferably from 8 to 15 amino acids, more preferably from 8 to 10 amino acids.

In particular embodiments, the peptide comprises, consists essentially of or consists of an amino acid sequence $FGGX_1MRRX_2$ (SEQ ID NO: 1), wherein $X_1$ is F or W, preferably F, and $X_2$ is K or V, preferably K.

In preferred embodiments, $X_2$ of SEQ ID NO: 1 is $NH_2$ substituted when $X_2$ is located at the C-terminus of the peptide.

In particular embodiments, the peptide comprises, consists essentially of or consists of an amino acid sequence $FGGX_1MRRX_2$(SEQ ID NO: 1), wherein $X_1$ is W and $X_2$ is K or V, preferably K.

In particular embodiments, the peptide comprises, consists essentially of or consists of an amino acid sequence $FGGX_1MRRX_2$(SEQ ID NO: 1), wherein $X_1$ is F and $X_2$ is K or V, preferably K.

In particular embodiments, if $X_2$ is V, the peptide has a length of at most 15 amino acids.

In particular embodiments, the peptide as taught herein is not homoserine O-acetyltransferase from *Chromohalobacter salexigens* as annotated under NCBI Genbank accession number WP_110061560.1.

In particular embodiments, the peptide as taught herein is not BAM-22, wherein the N-terminal tyrosine (Y) is substituted by phenylalanine (F) as described in Ikeda et al. (Ikeda et al., 2013, Modulation of circadian glucocorticoid oscillation through adrenal opioid-CXCR7 signaling alters emotional behavior, Cell. 155(6): 1323-1336).

In particular embodiments, the peptide comprises, consists essentially of or consists of an amino acid sequence $FGGX_1MRRX_2$(SEQ ID NO: 1), wherein $X_1$ is F.

In particular embodiments, the peptide comprises, consists essentially of or consists of an amino acid sequence $FGGX_1MRRX_2$(SEQ ID NO: 1), wherein $X_1$ is W.

In particular embodiments, the peptide comprises, consists essentially of or consists of an amino acid sequence $FGGX_1MRRX_2$(SEQ ID NO: 1), wherein $X_2$ is K.

Present inventors found that especially a peptide comprising, consisting essentially of or consisting of, preferably consisting of, amino acid sequence FGGFMRRK (SEQ ID NO: 3; $NH_2$-substituted at C-terminus) (also referred to herein as "LIH383") is a highly potent (i.e. $EC_{50}$ in the subnanomolar range) and selective peptide modulator of ACKR3, being even 20 times more potent than known ACKR3 agonists, such as compound 18 as described in Menhaji-Klotz et al., Discovery of a novel small-molecule modulator of C—X—C chemokine receptor type 7 as a treatment of cardiac fibrosis, J. Med. Chem, 2018, 61(8): 3685-3696, which has a $EC_{50}$ of 11 nM.

Accordingly, in preferred embodiments, the peptide comprises, consists essentially of or consists of an amino acid sequence $FGGX_1MRRX_2$(SEQ ID NO: 1), wherein $X_1$ is F and $X_2$ is K. In other words, in preferred embodiments, the peptide comprises, consists essentially of or consists of amino acid sequence FGGFMRRK (SEQ ID NO: 3), in even more preferred embodiments the peptide comprises, consists essentially of or consists of amino acid sequence FGGFMRRK (SEQ ID NO: 3; $NH_2$-substituted at C-terminus).

In particular embodiments, the peptide comprises at least one (e.g. one, two, three or four, preferably one or two, more preferably one) amino acid C-terminally of the amino acid sequence $FGGX_1MRRX_2$ (SEQ ID NO: 1), wherein $X_1$ is F or W and $X_2$ is K, V or F. In other words, in particular embodiments, the peptide comprises, consists essentially of or consists of, preferably consists of, amino acid sequence: $FGGX_1MRRX_2X_3$(SEQ ID NO: 2) or $FGGX_1MRRX_2X3X_4$ (SEQ ID NO: 7), $FGGX_1MRRX_2X3\ X_4\ X_5$ (SEQ ID NO: 8), $FGGX_1MRRX_2X3\ X_4\ X_5\ X_6$ (SEQ ID NO: 9), wherein $X_1$ is F or W, $X_2$ is K, V or F and $X_3$, $X_4$, $X_5$ and $X_6$ can be any amino acid. In preferred embodiments, $X_3$ of SEQ ID NO: 2, $X_4$ of SEQ ID NO: 7, $X_5$ of SEQ ID NO: 8 or $X_6$ of SEQ ID NO: 9 is $NH_2$ substituted when $X_3$, $X_4$, $X_5$ or $X_{6s}$ respectively, is located at the C-terminus of the peptide. In particular embodiments, the peptide comprises, consists essentially of or consists of amino acid sequence: $FGGX_1MRRX_2X3$ (SEQ ID NO: 2), wherein $X_1$ is F or W, $X_2$ is K, V or F and $X_3$ is R or A.

In particular embodiments, the peptide comprises amino acid sequence G, GR, GRP, GRPE (SEQ ID NO: 73), GRPEW (SEQ ID NO: 74), GRPEWW (SEQ ID NO: 75), or GRPEWWM (SEQ ID NO: 76) C-terminally of the amino acid sequence $FGGX_1MRRX_2$(SEQ ID NO: 1), wherein $X_1$ is F or W and $X_2$ is K, V or F.

In particular embodiments, the peptide comprises, consists essentially of or consists of an amino acid sequence selected from the group consisting of FGGFMRRK (SEQ ID NO: 3), FGGFMRRKR (SEQ ID NO: 4), FGGFMRRVR (SEQ ID NO: 5), FGGWMRRK (SEQ ID NO: 6), FGGWMRRVR (SEQ ID NO: 10), FGGWMRRKR (SEQ ID NO: 11), FGGWMRRV (SEQ ID NO: 68), FGGFMRRF (SEQ ID NO: 69), FGGFMRRFR (SEQ ID NO: 70), FGGWMRRFR (SEQ ID NO: 71) or FGGWMRRF (SEQ ID NO: 72), preferably selected from the group consisting of FGGFMRRK (SEQ ID NO: 3), FGGFMRRKR (SEQ ID NO: 4), FGGFMRRVR (SEQ ID NO: 5), FGGWMRRK (SEQ ID NO: 6), FGGWMRRVR (SEQ ID NO: 10) or FGGWMRRKR (SEQ ID NO: 11), more preferably FGGFMRRK (SEQ ID NO: 3), FGGFMRRKR (SEQ ID NO: 4), FGGFMRRVR (SEQ ID NO: 5), FGGWMRRK (SEQ ID NO: 6), even more preferably FGGFMRRK (SEQ ID NO: 3).

In a preferred embodiment, the C-terminus of the peptide as taught herein is $NH_2$-substituted. If the C-terminal $NH_2$-substituted form of the peptide as taught herein is intended, the peptide will be referred to by its SEQ ID NO, followed by the phrase "$NH_2$-substituted at C-terminus". For example, the sequence of LIH383 will be indicated as "(SEQ ID NO: 3; $NH_2$-substituted at C-terminus)".

Accordingly, in particular embodiments, the peptide comprises, consists essentially of or consists of, preferably consists of, an amino acid sequence selected from the group consisting of FGGFMRRK (SEQ ID NO: 3; $NH_2$-substituted at C-terminus) wherein the C-terminal K is $NH_2$-substituted, FGGFMRRKR (SEQ ID NO: 4; $NH_2$-substituted at C-terminus) wherein the C-terminal R is $NH_2$-substituted, FGGFMRRVR (SEQ ID NO: 5; $NH_2$-substituted at C-terminus) wherein the C-terminal R is $NH_2$-substituted, FGGWMRRK (SEQ ID NO: 6; $NH_2$-substituted at C-terminus) wherein the C-terminal K is $NH_2$-substituted, FGGWMRRVR (SEQ ID NO: 10; $NH_2$-substituted at C-terminus) wherein the C-terminal R is $NH_2$-substituted, FGGWMRRKR (SEQ ID NO: 11; $NH_2$- substituted at C-terminus) wherein the C-terminal R is NH₂-substituted, FGGWMRRV (SEQ ID NO: 68; NH₂-substituted at C-terminus) wherein the C-terminal V is NH₂-substituted, FGGFMRRF (SEQ ID NO: 69; NH₂-substituted at C-terminus) wherein the C-terminal F is NH₂-substituted, FGGFMRRFR (SEQ ID NO: 70; NH₂-substituted at C-terminus) wherein the C-terminal R is NH₂-substituted, FGGWMRRFR (SEQ ID NO: 71; NH₂-substituted at C-terminus) wherein the C-terminal R is NH₂-substituted or FGGWMRRF (SEQ ID NO: 72; NH₂-substituted at C-terminus) wherein the C-terminal F is NH₂-substituted, preferably selected from the group consisting of FGGFMRRK (SEQ ID NO: 3; NH₂-substituted at C-terminus) wherein the C-terminal K is NH-substituted, FGGFMRRKR (SEQ ID NO: 4; NH₂-substituted at C-terminus) wherein the C-terminal R is NH₂-substituted, FGGFMRRVR (SEQ ID NO: 5; NH₂-substituted at C-terminus) wherein the C-terminal R is NH₂-substituted, FGGWMRRK (SEQ ID NO: 6; NH₂-substituted at C-terminus) wherein the C-terminal K is NH₂-substituted, FGGWMRRVR (SEQ ID NO: 10; NH₂-substituted at C-terminus) wherein the C-terminal R is NH₂-substituted or FGGWMRRKR (SEQ ID NO: 11; NH₂-substituted at C-terminus) wherein the C-terminal R is NH₂-substituted, more preferably FGGFMRRK (SEQ ID NO: 3; NH₂-substituted at C-terminus) wherein the C-terminal K is NH-substituted, FGGFMRRKR (SEQ ID NO: 4; NH₂-substituted at C-terminus) wherein the C-terminal K is NH-substituted, FGGFMRRVR (SEQ ID NO: 5; NH-substituted at C-terminus) wherein the C-terminal R is NH-substituted, FGGWMRRK (SEQ ID NO: 6; NH₂-substituted at C-terminus) wherein the C-terminal K is NH-substituted, even more preferably FGGFMRRK (SEQ ID NO: 3; NH₂-substituted at C-terminus) wherein the C-terminal K is NH₂-substituted. In particular embodiments, the peptide is capable of specifically binding ACKR3.

The terms "bind", "interact", "specifically bind" or "specifically interact" as used throughout this specification mean that an agent binds to or influences one or more desired molecules or analytes substantially to the exclusion of other molecules which are random or unrelated, and optionally substantially to the exclusion of other molecules that are structurally related. The terms do not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold or more greater, such as, e.g., at least about 1000-fold or more greater, at least about $1\times10^4$-fold or more greater, or at least about $1\times10^5$-fold or more greater, than its affinity for a non-target molecule.

The binding or interaction between the agent and its intended target(s) may be covalent (i.e., mediated by one or more chemical bonds that involve the sharing of electron pairs between atoms) or, more typically, non-covalent (i.e., mediated by non-covalent forces, such as for example, hydrogen bridges, dipolar interactions, van der Waals interactions, and the like). Preferably, the agent may bind to or interact with its intended target(s) with affinity constant ($K_A$) of such binding $K_A\geq1\times10^6$ M⁻¹, more preferably $K_A\geq1\times10^7$ M⁻¹, yet more preferably $K_A\geq1\times10^8$ M⁻¹, even more preferably $K_A\geq1\times10^9$ M⁻¹, and still more preferably $K_A\geq1\times10^{10}$ M⁻¹ or $K_A\geq1\times10^{11}$M⁻¹, wherein $K_A$=[A_T]/[A][T], A denotes the agent, T denotes the intended target. Determination of $K_A$ can be carried out by methods known in the art, such as for example, using equilibrium dialysis and Scatchard plot analysis.

A peptide is said to "specifically bind to" a particular target when that peptide has affinity for, specificity for, and/or is specifically directed against that target (i.e., against at least one part or fragment thereof).

The "specificity" of a peptide as taught herein can be determined based on affinity. The "affinity" of a polypeptide is represented by the equilibrium constant for the dissociation of the peptide and ACKR3, preferably human ACKR3 (e.g. as annotated under NCBI Genbank accession number NP_064707.1). The lower the KD value, the stronger the binding strength between the peptide and ACKR3. Alternatively, the affinity can also be expressed in terms of the affinity constant (KA), which corresponds to 1/KD. A KD value greater than about 1 millimolar is generally considered to indicate non-binding or non-specific binding.

The binding of an agent, such as a peptide, as described herein to a target and the affinity and specificity of said binding may be determined by any methods known in the art. Non-limiting examples thereof include binding competition assays using fluorescently labelled or radiolabelled ligands (e.g. fluorescently labelled or radiolabelled chemokines, such as CXCL12), co-immunoprecipitation, bimolecular fluorescence complementation, affinity electrophoresis, label transfer, phage display, proximity ligation assay (PLA), Tandem affinity purification (TAP), in-silico docking and calculation of the predicted Gibbs binding energy and competition binding assays.

Present inventors found that the peptides as taught herein have the ability to recruit β-arrestin-1 and β-arrestin-2 to the ACKR3 receptor when being used at nanomolar concentrations or even at subnanomolar concentrations.

In particular embodiments, the peptide as taught herein has a potency for ACKR3 that is characterized by an EC₅₀ of 10 nM or less, 9 nM or less, 8 nM or less, 7 nM or less, 6 nM or less, 5 nM or less, 4 nM or less, 3 nM or less, 2 nM or less, 1 nM or less, 0.95 nM or less, 0.90 nM or less, 0.85 nM or less, 0.80 nM or less, 0.75 nM or less, 0.70 nM or less or 0.65 nM or less, preferably an EC₅₀ of 5 nM or less, more preferably an EC₅₀ of 1 nM or less. For example, the peptide as taught herein has a potency for ACKR3 that is characterized by an EC₅₀ of 0.61 nM. The EC₅₀ in the context of the present invention was determined based on β-arrestin recruitment assay. β-arrestin recruitment can be determined by any methods known in the art such as by nanoluciferase complementation assays (e.g. NanoBiT, Promega), for instance using ACKR3 C-terminally fused to SmBiT and the β-arrestin N-terminally fused to LgBiT.

In particular embodiments, the peptide as taught herein is capable of binding the binding pocket of ACKR3.

In particular embodiments, the peptide as taught herein inhibits, reduces and/or prevents the interaction between ACKR3 and ACKR3 endogenous or exogenous ligands, such as endogenous opioid peptides (e.g. BAM-22), endogenous chemokines (e.g. CXCL12 or CXCL11), or exogenous opioid peptides.

In particular embodiments, the peptide as taught herein inhibits, reduces and/or prevents the interaction between ACKR3 and an endogenous opioid peptide, such as an endogenous opioid peptide derived from proenkephalin, prodynorphin, proopiomelanocortin or prepronociceptin.

Preferably, an endogenous opioid peptide selected from the group consisting of BAM-22, BAM-18, Peptide E, adrenorphin, dynorphin A or fragments thereof (e.g. dynorphin 1-13, dynorphin 2-17), dynorphin B, big dynorphin or a fragment thereof, nociceptin or a fragment thereof.

In particular embodiments, the peptide as taught herein inhibits, reduces and/or prevents the interaction between ACKR3 and an endogenous chemokine selected from the group consisting of CXCL12 (e.g. with Uniprot accession number P48061) and CXCL11 (e.g. with Uniprot accession number O14625).

The inhibition, reduction and/or prevention of the interaction between ACKR3 and endogenous ACKR3 ligands by the peptide as taught herein can be determined by any means known in the art, such as competition binding assays or displacement assays. In particular embodiments, the peptide is able to displace labelled CXCL12 at a concentration of less than 1 µM, more particularly less than 100 nM or less than 10 nM. As described earlier, present inventors found that ACKR3, in contrast to the known opioid receptors and in contrast to what was proposed by Ikeda et al. (Ikeda et al., 2013, Modulation of circadian glucocorticoid oscillation through adrenal opioid-CXCR7 signaling alters emotional behavior, Cell. 155(6): 1323-1336), is unable to activate downstream signalling pathways, for instance via G proteins or β-arrestins, in response to endogenous opioid peptides, but rather acts as a scavenger, regulating their local and/or systemic concentrations and thus availability for the classical opioid receptors. The absence or presence of downstream signalling pathway activation may be determined using methods known in the art, such as using a whole-cell biosensing approach based on dynamic mass redistribution, determining the recruitment of mini G proteins to the receptor, determining the phosphorylation level of ERK1/2, and determining activation of SRE (ERK1/2) and NFAT-RE ($Ca^{2+}$) signalling cascades.

Accordingly, in line with the inventor's finding that ACKR3 acts as a scavenger in response to endogenous opioid peptides, in particular embodiments, the peptide as taught herein does not induce G-protein-mediated signalling mediated by ACKR3. The absence or presence of G-protein-mediated signalling may be determined using methods known in the art, such as determining the recruitment of mini G proteins to the receptor, determining the phosphorylation level of ERK1/2, whole cell biosensing approaches based on dynamic mass redistribution and determining activation of SRE (ERK1/2) and NFAT-RE ($Ca^{2+}$) signalling cascades.

In more particular embodiments, the peptide as taught does not induce recruitment of mini G proteins (mGs) (e.g. $G_{\alpha s}$, $G_{\alpha i/o}$, $G_{\alpha q/11}$ and/or $G_{\alpha 12/13}$) to ACKR3. The recruitment of mGs to ACKR3 (or the absence thereof) can be determined by any established analytical technique for determining protein-protein binding, such as co-immunoprecipitation, bimolecular fluorescence complementation, label transfer, tandem affinity purification, chemical crosslinking, fluorescence resonance energy transfer and nanoluciferase complementation assays (e.g. NanoBiT, Promega), for instance using ACKR3 C-terminally fused to SmBiT and mGs N-terminally fused to LgBiT. Protein binding assays may be performed in a cell-free system or in a cell lysate or in isolated or cultured cells or in an isolated or cultured tissue.

In particular embodiments, the peptide as taught herein does not activate any signalling pathway (e.g. cAMP signalling and/or the MAPK/ERK signalling pathway) as a result of the recruitment of β-arrestin- and/or β-arrestin-2 to the ACKR3 receptor.

In particular embodiments, the peptide as taught herein is not capable of interacting with and/or activating mu (µ)-type opioid receptor (MOR), delta (δ)-type opioid receptor (DOR), kappa (κ)-type opioid receptor (KOR) and non-classical nociceptin receptor (NOP). In more particular embodiments, the peptide as taught herein does not reduce the recruitment of β-arrestin 1 and β-arrestin 2 to the MOR, DOR, KOR and/or NOP receptor(s) induced by a known ligand of the MOR, DOR, KOR and/or NOP receptor(s), respectively. In more particular embodiments, the peptide as taught herein does not induce G-protein-mediated signalling via the MOR, DOR, KOR and/or NOP receptor(s). In more particular embodiments, the peptide as taught herein is not capable of inducing the recruitment of β-arrestin 1 and β-arrestin 2 to the MOR, DOR, KOR and/or NOP receptor(s). The absence of G-protein-mediated signalling can be determined by any methods known in the art such as determining the phosphorylation level of ERK1/2 upon contacting an agent with ACKR3, wherein a lack of phosphorylated ERK1/2 is indicative of the absence of G-protein-mediated signalling.

In particular embodiments, the peptide as disclosed herein is not capable of inducing the recruitment of β-arrestin-1 and β-arrestin-2 to the MOR, DOR, KOR or NOP receptor. In more particular embodiments, the peptide as disclosed herein does not enhance or even reduces β-arrestin-1 or β-arrestin-2 recruitment to the MOR, DOR, KOR or NOP receptor compared to the baseline β-arrestin-1 or β-arrestin-2 recruitment or background β-arrestin-1 or β-arrestin-2 recruitment induced by a neutral substance or negative control. As described elsewhere herein, the recruitment of β-arrestin-1 and β-arrestin-2 to the MOR, DOR, KOR or NOP receptor can be measured by a nanoluciferase complementation assays.

Any existing, available or conventional separation, detection and quantification methods may be used herein to measure the presence or absence (e.g., readout being present vs. absent; or detectable amount vs. undetectable amount) and/or quantity (e.g., readout being an absolute or relative quantity, such as, for example, absolute or relative concentration) of peptides, polypeptides, proteins in samples. For example, such methods may include biochemical assay methods, immunoassay methods, mass spectrometry analysis methods, or chromatography methods, or combinations thereof.

In particular embodiments, the peptide as taught herein is not capable of inducing the recruitment of β-arrestin-1 and β-arrestin-2 to any other chemokine receptor than ACKR3, more particularly a chemokine receptor selected from the group consisting of C—C chemokine receptor type 1 (CCR1) (e.g. with UniProt accession number P32246), C—C chemokine receptor type 2 (CCR2) (e.g. with UniProt accession number P41597) such as CCR type 2A (CCR2A) or CCR type 2B (CCR2B), C—C chemokine receptor type 3 (CCR3) (e.g. with UniProt accession number P51677), C—C chemokine receptor type 4 (CCR4) (e.g. with UniProt accession number P51679), C—C chemokine receptor type 5 (CCR5) (e.g. with UniProt accession number P51681), C—C chemokine receptor type 6 (CCR6) (e.g. with UniProt accession number P51684), C—C chemokine receptor type 7 (CCR7) (e.g. with UniProt accession number P32248), C—C chemokine receptor type 8 (CCR8) (e.g. with UniProt accession number P51685), C—C chemokine receptor type 9 (CCR9) (e.g. with UniProt accession number P51686), C—C chemokine receptor type 10 (CCR10) (e.g. with UniProt accession number P46092), C—X—C motif chemokine receptor 1 (CXCR1) (e.g. with UniProt accession number P25024), C—X—C motif chemokine receptor 2 (CXCR2) (e.g. with UniProt accession number P25025), C—X—C motif chemokine receptor 3 (CXCR3) (e.g. with UniProt accession number P49682) such as CXCR type 3A (CXCR3A) and CXCR type 3B (CXCR3B), C—X—C motif chemokine receptor 4 (CXCR4) (e.g. with UniProt accession number P61073), C—X—C motif chemokine receptor 5 (CXCR5) (e.g. with UniProt accession number P32302), C—X—C motif chemokine receptor 6 (CXCR6) (e.g. with UniProt accession number 000574), C—X—C motif chemokine receptor 8 (CXCR8) (e.g. with UniProt accession number Q9HC97), X—C motif chemokine receptor 1 (XCR1) (e.g. with UniProt accession number P46094), C—X3-C motif chemokine receptor 1 (CX3CR1) (e.g. with UniProt accession number P49238), atypical chemokine receptor 1 (ACKR1) (e.g. with UniProt accession number Q16570), atypical chemokine receptor 2 (ACKR2) (e.g. with UniProt accession number 000590) and atypical chemokine receptor 4 (ACKR4) (e.g. with UniProt accession number Q9NPB9).

In particular embodiments, the peptide as disclosed herein is not capable of inducing the recruitment of β-arrestin-1 and β-arrestin-2 to the CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 or ACKR4 receptor. In even more particular embodiments, the peptide as disclosed herein does not enhance or reduces β-arrestin-1 or β-arrestin-2 recruitment to the CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 or ACKR4 receptor compared to the baseline β-arrestin-1 or β-arrestin-2 recruitment or background β-arrestin-1 or β-ar-restin-2 recruitment induced by a neutral substance or nega-tive control. As described elsewhere herein, the recruitment of β-arrestin-1 and β-arrestin-2 to the CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 or ACKR4 receptor can be measured by a nanoluciferase complementation assays.

By means of additional guidance, atypical chemokine receptor 3 (ACKR3) is also known in the art as chemokine receptor 7 (CXCR7). By means of an example, human ACKR3 mRNA is annotated under NCBI Genbank acces-sion number NM_020311.2. Human ACKR3 polypeptide is annotated under NCBI Genbank (www.ncbi.nlm.nih.gov) accession number NP_064707.1, and Uniprot accession number P25106.

By means of additional guidance, mu (μ)-type opioid receptor (MOR) is also known in the art as OPRM, LMOR or MOP. By means of an example, human MOR protein is annotated under NCBI Genbank (www.ncbi.nlm.nih.gov) accession number AY521028.1 and Uniprot accession num-ber P35372.

By means of additional guidance, delta (δ)-type opioid receptor (DOR) is also known in the art as OPRD or DOP. By means of an example, human DOR protein is annotated under NCBI Genbank (www.ncbi.nlm.nih.gov) accession number NM_000911.4 and Uniprot accession number P41143.

By means of additional guidance, kappa (κ)-type opioid receptor (KOR) is also known in the art as OPRK or KOP. By means of an example, human KOR protein is annotated under NCBI Genbank (www.ncbi.nlm.nih.gov) accession number AF498922.1 and Uniprot accession number P41145.

By means of additional guidance, non-classical nociceptin receptor (NOP) is also known in the art as orphanin FQ receptor, OPRL and opioid related nociceptin receptor 1. By means of an example, human NOP protein is annotated under NCBI Genbank (www.ncbi.nlm.nih.gov) accession number AY268428.1 and Uniprot accession number P41146.

A skilled person can appreciate that any sequences rep-resented in sequence databases or in the present specification may be of precursors of the respective peptides, polypep-tides, proteins or nucleic acids and may include parts which are processed away from mature molecules.

References to any peptides, polypeptides, proteins or nucleic acids denote the respective peptides, polypeptides, proteins or nucleic acids as commonly known under the respective designations in the art. More particularly, the references to "ACKR3", "MOR", "DOR", "KOR", "NOP", "CCR1", "CCR2A", "CCR2B", "CCR3", "CCR4", "CCR5", "CCR6", "CCR7", "CCR8", "CCR9", "CCR10", "CXCR1", "CXCR2", "CXCR3A", "CXCR3B", "CXCR4", "CXCR5", "CXCR6", "CXCR8", "XCR1", "CX3CR1", "ACKR1", "ACKR2" or "ACKR4" denote the respective peptides, polypeptides, proteins or nucleic acids, as apparent from the context, as commonly known under said designa-tions in the art.

The terms encompass the peptides, polypeptides, proteins or nucleic acids when forming a part of a living organism, organ, tissue or cell, when forming a part of a biological sample, as well as when at least partly isolated from such sources. The terms also encompass the peptides, polypep-tides, proteins or nucleic acids when produced by recombi-nant or synthetic means.

The reference to any peptides, polypeptides, proteins or nucleic acids encompass such peptides, polypeptides, pro-teins or nucleic acids of any organism where found, and particularly of animals, preferably warm-blooded animals, more preferably vertebrates, yet more preferably mammals, including humans and non-human mammals, still more preferably of humans.

Hence, in certain embodiments, one or more and prefer-ably all of ACKR3, MOR, DOR, KOR, NOP, CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 and ACKR4 as employed herein is or are of animal origin, preferably warm-blooded animal origin, more preferably vertebrate origin, yet more preferably mammalian origin, including human origin and non-human mammalian origin, still more preferably human origin.

For biological peptides, polypeptides, proteins or nucleic acids the native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of peptides, polypeptides, proteins or nucleic acids are intended herein. Accordingly, all sequences of peptides, polypeptides, proteins or nucleic acids found in or derived from nature are considered "native".

Unless otherwise apparent from the context, reference herein to any peptide, polypeptide, protein or nucleic acid also encompasses modified forms of said peptide, polypep-tide, protein or nucleic acid, such as forms bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulphonation, methylation, ubiquitination, signal peptide removal, N-terminal Met removal, conversion of pro-enzymes or pre-hormones into active forms, etc. The term further also includes protein variants or mutants which carry amino acid sequence variations vis-A-vis a corresponding native proteins, such as, e.g., amino acid deletions, additions and/or substitutions. The term contemplates both full-length proteins and protein parts or fragments, e.g., naturally occurring protein parts that ensue from processing of such full-length proteins.

The term "polypeptide" as used throughout this specification generally encompasses polymeric chains of amino acid residues linked by peptide bonds. Hence, especially when a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants, which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally occurring polypeptide parts that ensue from processing of such full-length polypeptides.

A polypeptide or protein can be naturally occurring, e.g., present in or isolated from nature, e.g., produced or expressed natively or endogenously by a cell or tissue and optionally isolated therefrom.

A polypeptide or protein can be recombinant, i.e., produced by recombinant DNA technology, and/or can be, partly or entirely, chemically or biochemically synthesised. Without limitation, polypeptide or protein can be produced recombinantly by a suitable host or host cell expression system and optionally isolated therefrom (e.g., a suitable bacterial, yeast, fungal, plant or animal host or host cell expression system), or produced recombinantly by cell-free translation or cell-free transcription and translation, or non-biological polypeptide or protein synthesis.

In particular embodiments, the peptide as taught herein may be fused to an agent.

In the context of present invention, the term "coupled" as used herein is synonymous with "connected", "bound", "fused", "joined" and refers to a physical link between at least two elements or components.

As used herein, the term "agent" broadly refers to any chemical (e.g., inorganic or organic), biochemical or biological substance, molecule or macromolecule (e.g., biological macromolecule), a combination or mixture thereof, a sample of undetermined composition, or an extract made from biological materials such as bacteria, fungi, plants, or animal cells or tissues. Preferred though non-limiting "agents" include nucleic acids, oligonucleotides, ribozymes, peptides, polypeptides, proteins, peptidomimetics, antibodies, antibody fragments, antibody-like protein scaffolds, aptamers, photoaptamers, spiegelmers, chemical substances, preferably organic molecules, more preferably small organic molecules, lipids, carbohydrates, polysaccharides, etc., and any combinations thereof.

In particular embodiments, the peptide as taught herein may be coupled to an agent selected from the group consisting of a chemical substance, an antibody, an antibody fragment, an antibody-like protein scaffold, a protein or polypeptide and a peptide, a peptidomimetic, an aptamer, a photoaptamer, a spiegelmer and a nucleic acid.

As used herein, the term "chemical substance" is used in its broadest sense and generally refers to any substantially pure substance that has a constant chemical composition and characteristic properties.

The chemical substance may be an organic molecule, preferably a small organic molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

The term "antibody" is used herein in its broadest sense and generally refers to any immunologic binding agent, such as a whole antibody, including without limitation a chimeric, humanized, human, recombinant, transgenic, grafted and single chain antibody, and the like, or any fusion proteins, conjugates, fragments, or derivatives thereof that contain one or more domains that selectively bind to an antigen of interest. The term antibody thereby includes a whole immunoglobulin molecule, a monoclonal antibody, a chimeric antibody, a humanized antibody, a human antibody, or an immunologically effective fragment of any of these. The term thus specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest), as well as multivalent and/or multi-specific composites of such fragments. The term "antibody" is not only inclusive of antibodies generated by methods comprising immunisation, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro, in cell culture, or in vivo.

The term "antibody fragment" or "antigen-binding moiety" comprises a portion or region of a full length antibody, generally the antigen binding or variable domain thereof. Examples of antibody fragments include Fab, Fab', F(ab)2, Fv, scFv fragments, single domain (sd)Fv, such as $V_H$ domains, $V_L$ domains and $V_{HH}$ domains, diabodies, linear antibodies, single-chain antibody molecules, in particular heavy-chain antibodies; and multivalent and/or multispecific antibodies formed from antibody fragment(s), e.g., dibodies, tribodies, and multibodies. The above designations Fab, Fab', F(ab')2, Fv, scFv etc. are intended to have their art-established meaning.

In more particular embodiments, the peptide as taught herein may be coupled to an agent selected from the group consisting of a detectable label such as a fluorescent protein or enzyme, an immunoglobulin Fc region (e.g. IgG2a Fc), protoxin, toxin or pharmaceutical, preferably a fluorescent protein, an enzyme, an immunoglobulin Fc region, a protoxin or a toxin.

In particular embodiments, the peptide as taught herein may be fused to a detectable label.

The term "label" refers to any atom, molecule, moiety or biomolecule that may be used to provide a detectable and preferably quantifiable read-out or property, and that may be attached to or made part of an entity of interest, such as the peptide as taught herein. Labels may be suitably detectable by for example mass spectrometric, spectroscopic, optical, colourimetric, magnetic, photochemical, biochemical, immunochemical or chemical means. Labels include without limitation dyes; radiolabels such as $^{32}P$, $^{33}P$, $^{35}S$, $^{125}I$, $^{131}I$; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes (e.g., fluorophores such as fluorescein, carboxyfluorescein (FAM), tetrachloro-fluorescein, TAMRA, ROX, Cy3, Cy3.5, Cy5, Cy5.5, Texas Red, etc.) alone or in combination with moieties that may suppress or shift emission spectra by fluorescence resonance energy transfer (FRET).

In some embodiments, the peptide as taught herein may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin:streptavidin, his-tag:metal ion (e.g., Ni$^{2+}$), maltose:maltose binding protein, etc.

In particular embodiments, the label may be Large BiT (LgBiT) or Small BiT (SmBiT) or HiBiT of NanoLuc® Binary Technology (NanoBiT).

The peptide as taught herein may be associated with or attached to a detection agent to facilitate detection. Examples of detection agents include, but are not limited to, luminescent labels; colorimetric labels, such as dyes; fluorescent labels (e.g. green fluorescent protein (GFP)); or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulphate particles; colloidal iron sulphate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads.

In particular embodiments, the peptide as taught herein may be coupled to the agent by one or more linkers.

As used herein, the term "linker" refers to a connecting element that serves to link other elements. The linker may be a rigid linker or a flexible linker. In particular embodiments, the linker is a covalent linker, achieving a covalent bond. The terms "covalent" or "covalent bond" refer to a chemical bond that involves the sharing of one or more electron pairs between two atoms. For many molecules, the sharing of electrons allows each atom to attain the equivalent of a full outer electron shell, corresponding to a stable electronic configuration. Covalent bonds include different types of interactions, including σ-bonds, π-bonds, metal-to-metal bonds, agostic interactions, bent bonds and three-center two-electron bonds.

In particular embodiments, the linker is a (poly) peptide linker or a non-peptide linker, such as a non-peptide polymer, such as a non-biological polymer. Preferably, the linkage(s) between the peptide as taught herein and the second peptide, protein or polypeptide may be hydrolytically stable linkage(s), i.e., substantially stable in water at useful pH values, including in particular under physiological conditions, for an extended period of time, e.g., for days. In particular embodiments, the linker is a peptide linker of one or more amino acids.

The term "amino acid" encompasses naturally occurring amino acids, naturally encoded amino acids, non-naturally encoded amino acids, non-naturally occurring amino acids, amino acid analogues and amino acid mimetics that function in a manner similar to the naturally occurring amino acids, all in their D and L stereoisomers, provided their structure allows such stereo-isomeric forms. Amino acids are referred to herein by either their name, their commonly known three letter symbols or by the one-letter symbols recommended by the IUPAC-IUB Biochemical Nomenclature Commission. The term "naturally occurring" generally refers to materials which are found in nature and are not manipulated by man. The terms "non-naturally occurring", "un-natural" and the like generally refer to a material that is not found in nature or that has been structurally modified, semi-synthesised or synthesised by man. The term includes without limitation amino acids that occur by a modification (such as a post-translational modification) of a naturally encoded amino acid, but are not themselves naturally incorporated into a growing polypeptide chain by the translation complex. Also included are amino acid analogues, in which one or more individual atoms have been replaced either with a different atom, an isotope of the same atom, or with a different functional group. Also included are un-natural amino acids and amino acid analogues described in Ellman et al. Methods Enzymol. 1991, vol. 202, 301-36. The incorporation of non-natural amino acids into proteins or polypeptides may be advantageous in a number of different ways. For example, D-amino acid-containing polypeptides exhibit increased stability in vitro or in vivo compared to L-amino acid-containing counterparts. More specifically, D-amino acid-containing polypeptides may be more resistant to endogenous peptidases and proteases, thereby providing improved bioavailability of the agent and prolonged lifetimes n vivo.

More particularly, the peptide linker may be 1 to 50 amino acids long or 2 to 50 amino acids long or 1 to 45 amino acids long or 2 to 45 amino acids long, preferably 1 to 40 amino acids long or 2 to 40 amino acids long or 1 to 35 amino acids long or 2 to 35 amino acids long, more preferably 1 to 30 amino acids long or 2 to 30 amino acids long. Further preferably, the linker may be 5 to 25 amino acids long or 5 to 20 amino acids long. Particularly preferably, the linker may be 5 to 15 amino acids long or 7 to 15 amino acids long. Hence, in certain embodiments, the linker may be 1, 2, 3 or 4 amino acids long. In other embodiments, the linker may be 5, 6, 7, 8 or 9 amino acids long. In further embodiments, the linker may be 10, 11, 12, 13 or 14 amino acids long. In still other embodiments, the linker may be 15, 16, 17, 18 or 19 amino acids long. In further embodiments, the linker may be 20, 21, 22, 23, 24 or 25 amino acids long. In certain embodiments, the linker is 4-10 or 5-9 or 6-8 or 7 amino acids long. In other embodiments, the linker is 12-18 or 13-17 or 14-16 or 15 amino acids long.

The nature of amino acids constituting the linker is not of particular relevance so long as the biological activity of the polypeptide segments linked thereby is not substantially impaired and the linker provides for the intended spatial separation of the peptide as taught herein and the second peptide, protein or polypeptide. Preferred linkers are essentially non-immunogenic and/or not prone to proteolytic cleavage.

In certain preferred embodiments, the peptide linker may comprise, consist essentially of or consist of amino acids selected from the group consisting of Glycine, Serine, Alanine, Threonine, and combinations thereof. In even more preferred embodiments, the linker may comprise, consist essentially of or consist of amino acids selected from the group consisting of Glycine, Serine, and combinations thereof. Such linkers provide for particularly good flexibility. In certain embodiments, the linker may consist of only Glycine residues. In certain embodiments, the linker may consist of only Serine residues.

In particular embodiments, the linker is a non-peptide linker. In preferred embodiments, the non-peptide linker may comprise, consist essentially of or consist of a non-peptide polymer. The term "non-peptide polymer" as used herein refers to a biocompatible polymer including two or more repeating units linked to each other by a covalent bond excluding the peptide bond. For example, the non-peptide polymer may be 2 to 200 units long or 2 to 100 units long or 2 to 50 units long or 2 to 45 units long or 2 to 40 units long or 2 to 35 units long or 2 to 30 units long or 5 to 25 units long or 5 to 20 units long or 5 to 15 units long. The non-peptide polymer may be selected from the group consisting of polyethylene glycol, polypropylene glycol, copolymers of ethylene glycol and propylene glycol, polyoxyethylated polyols, polyvinyl alcohol, polysaccharides, dextran, polyvinyl ethyl ether, biodegradable polymers such as PLA (poly(lactic acid) and PLGA (polylactic-glycolic acid), lipid polymers, chitins, hyaluronic acid, and combinations thereof. Particularly preferred is poly(ethylene glycol) (PEG). The molecular weight of the non-peptide polymer preferably may range from 1 to 100 kDa, and preferably 1 to 20 kDa. The non-peptide polymer may be one polymer or a combination of different types of polymers. The non-peptide polymer has reactive groups capable of binding to the peptide as taught herein and the second peptide, protein or polypeptide, which are to form the conjugate. Preferably, the non-peptide polymer has a reactive group at each end. Preferably, the reactive group is selected from the group consisting of a reactive aldehyde group, a propione aldehyde group, a butyl aldehyde group, a maleimide group and a succinimide derivative. The succinimide derivative may be succinimidyl propionate, hydroxy succinimidyl, succinimidyl carboxymethyl or succinimidyl carbonate. The reactive groups at both ends of the non-peptide polymer may be the same or different. In certain embodiments, the non-peptide polymer has a reactive aldehyde group at both ends. For example, the non-peptide polymer may possess a maleimide group at one end and, at the other end, an aldehyde group, a propionic aldehyde group or a butyl aldehyde group. When a polyethylene glycol (PEG) having a reactive hydroxy group at both ends thereof is used as the non-peptide polymer, the hydroxy group may be activated to various reactive groups by known chemical reactions, or a PEG having a commercially-available modified reactive group may be used so as to prepare the protein conjugate.

In particular embodiments, the agent is fused to the C-terminal end of the peptide as taught herein. A related aspect provides a fusion protein comprising the peptide as taught herein.

The terms "fusion protein" or "fusion polypeptide" and "protein conjugate" or "polypeptide conjugate" denote hybrid or chimeric molecules comprising at least two peptides, proteins or polypeptides linked, connected or joined together in a manner not normally found in nature. The molecules may be suitably denoted as amino acid-based compounds, i.e., as substances or molecules as including primarily but not necessarily exclusively amino acid residues. Any recombinantly, semi-synthetically or synthetically produced fusions or conjugates are encompassed. The fusions or conjugates may be if desired modified by glycosylation, phosphorylation, sulphonation, methylation, acetylation, lipidation, pegylation or the like.

More particularly, the terms "fusion protein" or "fusion polypeptide" denote genetic fusions, whereby two or more peptides, proteins, polypeptides or variants or fragments thereof are joined by a co-linear, covalent linkage via their individual polypeptide backbones, through genetic expression of a single contiguous polynucleotide molecule encoding the fusion product. Typically, to produce the contiguous polynucleotide molecule encoding the fusion product, two or more open reading frames (ORFs) each encoding a given polypeptide segment are joined to form a continuous longer ORF in a manner that maintains the correct reading frame for each original ORF. In the resulting recombinant fusion polypeptide the two or more polypeptide segments encoded by the original ORFs are joined in the same polypeptide molecule, whereas they are not normally so joined in nature. While the reading frame is thus made continuous throughout the fused genetic segments, the so fused polypeptide segments may be physically or spatially separated by, for example, an in-frame polypeptide or peptide linker.

In particular embodiments, the fusion protein further comprises an agent as described elsewhere herein, wherein agent is a peptide, protein or polypeptide, preferably a detectable label or tag; or immunoglobulin Fc region.

In particular embodiments, the fusion protein further comprises one or more linkers as described elsewhere herein, wherein the linker is located between the peptide as taught herein and the agent as described elsewhere herein.

A further aspect provides a nucleic acid encoding for the peptide as taught herein or the fusion protein as taught herein.

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups.

Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

By "encoding" is meant that a nucleic acid sequence or part(s) thereof corresponds, by virtue of the genetic code of an organism in question to a particular amino acid sequence, e.g., the amino acid sequence of one or more desired proteins or polypeptides, or to another nucleic acid sequence in a template-transcription product (e.g. RNA or RNA analogue) relationship.

To allow expression of the nucleic acid encoding the peptide or the fusion protein as taught herein, the nucleic acid may be inserted into a nucleic acid expression cassette and/or vector, as is well-known in the art.

A further aspect provides a nucleic acid expression cassette comprising the nucleic acid as taught herein, operably linked to a promoter and/or transcriptional and translational regulatory signals.

The term "nucleic acid expression cassettes" as used herein refers to nucleic acid molecules, typically DNA, to which nucleic acid fragments may be inserted to be expressed, wherein said nucleic acid molecules comprise one or more nucleic acid sequences controlling the expression of the nucleic acid fragments. Non-limiting examples of such more nucleic acid sequences controlling the expression of the nucleic acid fragments include promoter sequences, open reading frames and transcription terminators.

Preferably, the nucleic acid expression cassette may comprise one or more open reading frames (ORF) encoding said one or more proteins, polypeptides or peptides. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a protein, polypeptide or peptide. Hence, the term may be synonymous with "coding sequence" as used in the art.

An "operable linkage" is a linkage in which regulatory sequences and sequences sought to be expressed are connected in such a way as to permit said expression. For example, sequences, such as, e.g., a promoter and an ORF, may be said to be operably linked if the nature of the linkage between said sequences does not: (1) result in the introduction of a frame-shift mutation, (2) interfere with the ability of the promoter to direct the transcription of the ORF, (3) interfere with the ability of the ORF to be transcribed from the promoter sequence. Hence, "operably linked" may mean incorporated into a genetic construct so that expression control sequences, such as a promoter, effectively control transcription/expression of a sequence of interest.

The precise nature of transcriptional and translational regulatory sequences or elements required for expression may vary between expression environments, but typically include a transcription terminator, and optionally an enhancer.

Reference to a "promoter" is to be taken in its broadest context and includes transcriptional regulatory sequences required for accurate transcription initiation and where applicable accurate spatial and/or temporal control of gene expression or its response to, e.g., internal or external (e.g., exogenous) stimuli. More particularly, "promoter" may depict a region on a nucleic acid molecule, preferably DNA molecule, to which an RNA polymerase binds and initiates transcription. A promoter is preferably, but not necessarily, positioned upstream, i.e., 5', of the sequence the transcription of which it controls. Typically, in prokaryotes a promoter region may contain both the promoter per se and sequences which, when transcribed into RNA, will signal the initiation of protein synthesis (e.g., Shine-Dalgarno sequence). A promoter sequence can also include "enhancer regions", which are one or more regions of DNA that can be bound with proteins (namely the trans-acting factors) to enhance transcription levels of genes in a gene-cluster. The enhancer, while typically at the 5' end of a coding region, can also be separate from a promoter sequence, e.g., can be within an intronic region of a gene or 3' to the coding region of the gene.

In embodiments, promoters contemplated herein may be constitutive or inducible. A constitutive promoter is understood to be a promoter whose expression is constant under the standard culturing conditions. Inducible promoters are promoters that are responsive to one or more induction cues. For example, an inducible promoter can be chemically regulated (e.g., a promoter whose transcriptional activity is regulated by the presence or absence of a chemical inducing agent such as an alcohol, tetracycline, a steroid, a metal, or other small molecule) or physically regulated (e.g., a promoter whose transcriptional activity is regulated by the presence or absence of a physical inducer such as light or high or low temperatures). An inducible promoter can also be indirectly regulated by one or more transcription factors that are themselves directly regulated by chemical or physical cues. Non-limiting examples of promoters include T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter.

The terms "terminator" or "transcription terminator" refer generally to a sequence element at the end of a transcriptional unit which signals termination of transcription. For example, a terminator is usually positioned downstream of, i.e., 3' of ORF(s) encoding a polypeptide of interest. For instance, where a recombinant nucleic acid contains two or more ORFs, e.g., successively ordered and forming together a multi-cistronic transcription unit, a transcription terminator may be advantageously positioned 3' to the most downstream ORF.

In particular embodiments, the nucleic acid expression cassette comprises the nucleic acid encoding the peptide or fusion protein as disclosed herein, operably linked to one or more promoters, enhancers, ORFs and/or transcription terminators.

A further aspect provides a vector comprising the nucleic acid as taught herein or the nucleic acid expression cassette as taught herein, such as a viral vector.

The term "vector" or "expression vector" as used in the application refers to nucleic acid molecules, e.g. double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a peptide, protein or polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The vectors can be episomal vectors (i.e., that do not integrate into the genome of a host cell), or can be vectors that integrate into the host cell genome. The term 'vector' may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, plasmid vectors (e.g. pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus. Another example encompasses viral vectors mixed with cationic lipids.

The peptide or fusion protein as taught herein may be suitably obtained through expression by host cells or host organisms, transformed with an expression construct encoding and configured for expression of said peptide or fusion protein in said host cells or host organisms, followed by purification of the peptide or fusion protein.

Hence, a further aspect provides a host cell comprising the nucleic acid, nucleic acid expression cassette or vector as taught herein.

In certain embodiments, the host cell may be a bacterial cell, a yeast cell, an animal cell, or a mammalian cell.

The terms "host cell" and "host organism" may suitably refer to cells or organisms encompassing both prokaryotes, such as bacteria, and eukaryotes, such as yeast, fungi, protozoan, plants and animals. Contemplated as host cells are inter alia unicellular organisms, such as bacteria (e.g., *E. coli, Salmonella tymphimurium, Serratia marcescens*, or *Bacillus subtilis*), yeast (e.g., *Saccharomyces cerevisiae* or

*Pichia pastoris*), (cultured) plant cells (e.g., from *Arabidopsis thaliana* or *Nicotiana tobaccum*) and (cultured) animal cells (e.g., vertebrate animal cells, mammalian cells, primate cells, human cells or insect cells). Contemplated as host organisms are inter alia multi-cellular organisms, such as plants and animals, preferably animals, more preferably warm-blooded animals, even more preferably vertebrate animals, still more preferably mammals, yet more preferably primates; particularly contemplated are such animals and animal categories which are non-human.

Such protein, polypeptide or peptide may be suitably isolated and/or purified. Purified nucleic acids, proteins, polypeptides or peptides may be obtained by known methods including, for example, laboratory or recombinant synthesis, chromatography, preparative electrophoresis, centrifugation, precipitation, affinity purification, etc.

In particular embodiments, the vector comprising the nucleic acid as described herein is a viral vector, preferably a viral vector specifically directed towards the central and/or peripheral nervous system (e.g., a brain-specific viral vector).

In particular embodiments, the nucleic acid encoding the agent as taught herein may be comprised within a vector providing for a signal peptide. The signal peptide may be a homologous or heterologous signal peptide, depending on the host cell used for production of the agent as taught herein. Furthermore, for prokaryotic expression of the agent as taught herein, a protease cleavage site motif may be present C-terminally of said signal peptide and N-terminally of the agent as taught herein.

A further aspect provides a pharmaceutical composition comprising the peptide as taught herein, the fusion peptide as taught herein, the nucleic acid as taught herein, the nucleic acid expression cassette as taught herein or the vector as taught herein, and optionally a pharmaceutically acceptable carrier.

The term "pharmaceutically acceptable" as used herein is consistent with the art and means compatible with the other ingredients of a pharmaceutical composition and not deleterious to the recipient thereof. As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, antioxidants, tonicity controlling agents, absorption delaying agents, and the like. The use of such media and agents for pharmaceutical active substances is well known in the art. Except insofar as any conventional media or agent is incompatible with the active substance, its use in the therapeutic compositions may be contemplated.

Illustrative, non-limiting carriers for use in formulating the pharmaceutical compositions include, for example, oil-in-water or water-in-oil emulsions, aqueous compositions with or without inclusion of organic co-solvents suitable for intravenous (IV) use, liposomes or surfactant-containing vesicles, microspheres, microbeads and microsomes, powders, tablets, capsules, suppositories, aqueous suspensions, aerosols, and other carriers apparent to one of ordinary skill in the art.

Pharmaceutical compositions as intended herein may be formulated for essentially any route of administration, such as without limitation, oral administration (such as, e.g., oral ingestion or inhalation), intranasal administration (such as, e.g., intranasal inhalation or intranasal mucosal application), parenteral administration (such as, e.g., subcutaneous, intravenous (I.V.), intramuscular, intraperitoneal or intrasternal injection or infusion), transdermal or transmucosal (such as, e.g., oral, sublingual, intranasal) administration, topical administration, rectal, vaginal or intra-tracheal instillation, and the like. In this way, the therapeutic effects attainable by the methods and compositions can be, for example, systemic, local, tissue-specific, etc., depending of the specific needs of a given application.

In preferred embodiments, the peptide, the fusion protein, the nucleic acid encoding the peptide or fusion protein, the nucleic acid expression cassette comprising the nucleic acid, the vector comprising the nucleic acid or the nucleic acid expression cassette, the host cell or the pharmaceutical composition as taught herein is administered parenterally. More preferably, the peptide, the fusion protein, the nucleic acid encoding the peptide or fusion protein, the nucleic acid expression cassette comprising the nucleic acid, the vector comprising the nucleic acid or the nucleic acid expression cassette, the host cell or the pharmaceutical composition as taught herein is administered intravenously, for example by infusion.

The dosage or amount of the agent as taught herein, optionally in combination with one or more other active compounds to be administered, depends on the individual case and is, as is customary, to be adapted to the individual circumstances to achieve an optimum effect. Thus, the unit dose and regimen depend on the nature and the severity of the disorder to be treated, and also on factors such as the species of the subject, the sex, age, body weight, general health, diet, mode and time of administration, immune status, and individual responsiveness of the human or animal to be treated, efficacy, metabolic stability and duration of action of the compounds used, on whether the therapy is acute or chronic or prophylactic, or on whether other active compounds are administered in addition to the agent of the invention. In order to optimize therapeutic efficacy, the peptide, the fusion protein, the nucleic acid encoding the peptide or fusion protein, the nucleic acid expression cassette comprising the nucleic acid, the vector comprising the nucleic acid or the nucleic acid expression cassette, the host cell or the pharmaceutical composition as taught herein can be first administered at different dosing regimens. Typically, levels of the agent in a tissue can be monitored using appropriate screening assays as part of a clinical testing procedure, e.g., to determine the efficacy of a given treatment regimen. The frequency of dosing is within the skills and clinical judgement of medical practitioners (e.g., doctors, veterinarians or nurses). Typically, the administration regime is established by clinical trials which may establish optimal administration parameters. However, the practitioner may vary such administration regimes according to the one or more of the aforementioned factors, e.g., subject's age, health, weight, sex and medical status. The frequency of dosing can be varied depending on whether the treatment is prophylactic or therapeutic.

Toxicity and therapeutic efficacy of the agent as described herein or pharmaceutical compositions comprising the same can be determined by known pharmaceutical procedures in, for example, cell cultures or experimental animals. These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Pharmaceutical compositions that exhibit high therapeutic indices are preferred. While pharmaceutical compositions that exhibit toxic side effects can be used, care should be taken to design a delivery system that targets such compounds to the site of affected tissue in order to minimize potential damage to normal cells (e.g., non-target cells) and, thereby, reduce side effects.

The data obtained from the cell culture assays and animal studies can be used in formulating a range of dosage for use in appropriate subjects. The dosage of such pharmaceutical compositions lies generally within a range of circulating concentrations that include the ED50 with little or no toxicity. The dosage may vary within this range depending upon the dosage form employed and the route of administration utilised. For a pharmaceutical composition used as described herein, the therapeutically effective dose can be estimated initially from cell culture assays. A dose can be formulated in animal models to achieve a circulating plasma concentration range that includes the IC50 (i.e., the concentration of the pharmaceutical composition which achieves a half-maximal inhibition of symptoms) as determined in cell culture. Such information can be used to more accurately determine useful doses in humans. Levels in plasma can be measured, for example, by high performance liquid chromatography.

In particular embodiment, the peptide or the fusion protein as taught herein is the main or only active ingredient of the pharmaceutical composition.

The selectivity and high affinity of the peptides as taught herein for ACKR3 provides the peptides as taught herein with many valuable in vitro, ex vivo and in vivo applications.

A further aspect provides the use of the peptide as described herein in stabilizing the ACKR3 polypeptide, for instance, during nuclear magnetic resonance (NMR) analysis. Conformational flexibility of receptors can be an obstacle in protein production and crystallography studies. As the peptide as taught herein specifically recognizes ACKR3 polypeptide, the peptide could be used to specifically target agents, such as detectable labels, pharmaceuticals, or toxins, to the ACKR3 polypeptide.

Accordingly, a further aspect provides the use of the peptide or the fusion protein as described herein for targeted delivery of an agent, such a pharmaceutical or toxin, to the ACKR3 polypeptide.

For example, ACKR3 is expressed in various cells such as B and T lymphocytes, neurons and endothelial cells and plays a role in many types of cancer, cardiovascular and neuronal development, cardiac and immune pathophysiology and migration and homing of hematopoietic stem/progenitor cells. ACKR3 is expressed in various cancer cell types (such as colorectal cancer, breast cancer, prostate cancer, lung cancer, liver cancer, lymphoma, leukaemia, glioblastoma and head and neck cancer) as well as on tumour-associated vasculature and is involved in metastasis development. ACKR3 is also upregulated upon infection by several cancer-inducing viruses including HHV-8, EBV, HTLV-1 and plays an important role in cell transformation and proliferation.

Accordingly, in particular embodiments, the peptide as taught herein fused to a toxin, is used in the treatment of cancer.

A related aspect provides the use of the peptide as described herein as a peptide tracer, for instance a peptide tracer for in vivo, ex vivo or in vitro imaging. For instance, the peptide as taught herein, when fused to a detectable label, could be used for visualizing cells, tissues and/or organs expressing ACKR3 (e.g. certain types of cancer cells). Accordingly, the peptide as taught herein, when fused to a detectable label, could also be used for visualizing diseases or conditions related to ACKR3, such as cancer, diseases or conditions involving excessive or abnormal angiogenesis, and inflammatory or autoimmune diseases and conditions (e.g. arthritis). More particularly, the peptide as taught herein, when fused to a detectable label, could be used for visualizing cancer, atherosclerotic vascular disease, cardiac fibrosis, or brain and neuronal dysfunction (e.g. Alzheimer's disease, multiple sclerosis and demyelinating diseases), in vivo, ex vivo or in vitro. Non-limiting examples of cancers which can be visualised using the peptide as taught herein include carcinomas, gliomas, mesotheliomas, melanomas, lymphomas, leukaemias, adenocarcinomas, breast cancer, ovarian cancer, cervical cancer, glioblastoma, prostate cancer, Burkitt's lymphoma, head and neck cancer, colon cancer, colorectal cancer, non-small cell lung cancer, small-cell lung cancer, cancer of the oesophagus, stomach cancer, pancreatic cancer, hepatobiliary cancer, cancer of the gallbladder, cancer of the small intestine, rectal cancer, kidney cancer, bladder cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, and non-Hodgkin's lymphoma.

A further aspect provides a method for in vitro or ex vivo detecting and/or determining the level of the ACKR3 polypeptide in a biological sample, comprising the steps of obtaining a biological sample obtained from a subject, contacting said biological sample with the peptide as taught herein, wherein said peptide is fused to a detectable label, detecting and/or determining the level of the ACKR3 polypeptide in said biological sample by detecting the peptide as taught herein.

The terms "level", "quantity", "amount" and are synonymous and generally well-understood in the art. The terms as used herein may particularly refer to an absolute quantification of a molecule or an analyte in a sample, or to a relative quantification of a molecule or analyte in a sample, i.e., relative to another value such as relative to a reference value as taught herein, or to a range of values indicating a base-line expression of the molecule or analyte. These values or ranges can be obtained from a single patient or from a group of patients.

A related aspect provides the peptide as taught herein for use in a method of diagnosis, prediction, prognosis and/or monitoring of a disease or condition characterized by an aberrant level of ACKR3 polypeptide in a subject, wherein the peptide is fused to a detectable label and corresponding methods of use.

Except when noted, the terms "subject" or "patient" can be used interchangeably and refer to animals, preferably warm-blooded animals, more preferably vertebrates, even more preferably mammals, still more preferably primates, and specifically includes human patients and non-human mammals and primates. Preferred subjects are human subjects. The terms "subject" or "patient" include subjects in need of treatment, more particularly subjects that would benefit from treatment of a given condition. Such subjects may include, without limitation, those that have been diagnosed with said condition, those prone to develop said condition and/or those in who said condition is to be prevented.

An absolute quantity of a molecule or analyte in a sample may be advantageously expressed as weight or as molar amount, or more commonly as a concentration, e.g., weight per volume or mol per volume. A relative quantity of a molecule or analyte in a sample may be advantageously expressed as an increase or decrease or as a fold-increase or fold-decrease relative to said another value, such as relative to a reference value as taught herein. Performing a relative comparison between first and second parameters (e.g., first and second quantities) may but need not require first to determine the absolute values of said first and second parameters. For example, a measurement method can produce quantifiable readouts (such as, e.g., signal intensities) for said first and second parameters, wherein said readouts are a function of the value of said parameters, and wherein said readouts can be directly compared to produce a relative value for the first parameter vs. the second parameter, without the actual need first to convert the readouts to absolute values of the respective parameters.

The terms "predicting" or "prediction", "diagnosing" or "diagnosis" and "prognosticating" or "prognosis" are commonplace and well-understood in medical and clinical practice. It shall be understood that the phrase "a method for the diagnosis, prediction and/or prognosis" a given disease or condition may also be interchanged with phrases such as "a method for diagnosing, predicting and/or prognosticating" of said disease or condition or "a method for making (or determining or establishing) the diagnosis, prediction and/or prognosis" of said disease or condition, or the like.

By means of further explanation and without limitation, "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

The terms "diagnosing" or "diagnosis" generally refer to the process or act of recognising, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition). As used herein, "diagnosis of" the diseases or conditions as taught herein in a subject may particularly mean that the subject has such, hence, is diagnosed as having such. "Diagnosis of no" diseases or conditions as taught herein in a subject may particularly mean that the subject does not have such, hence, is diagnosed as not having such. A subject may be diagnosed as not having such despite displaying one or more conventional symptoms or signs reminiscent of such.

The terms "prognosticating" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

Hence, prediction or prognosis of a disease or condition can inter alia allow to predict or make a prognosis of the occurrence of the disease or condition, or to predict or make a prognosis of the progression, aggravation, alleviation or recurrence of the disease or condition or response to treatment or to other external or internal factors, situations or stressors, etc.

Further, monitoring a disease or condition can inter alia allow to predict the occurrence of the disease or condition, or to monitor the progression, aggravation, alleviation or recurrence of the disease or condition, or response to treatment or to other external or internal factors, situations or stressors, etc. Advantageously, monitoring may be applied in the course of a medical treatment of a subject, preferably medical treatment aimed at alleviating the so-monitored disease or condition. Such monitoring may be comprised, e.g., in decision making whether a patient may be discharged, needs a change in treatment or needs further hospitalisation. As intended herein, a reference to monitoring of a disease or condition also specifically includes monitoring of the probability, risk or chance of a subject to develop the disease or condition, i.e., monitoring change(s) in said probability, risk or chance over time.

A related aspect provides a method for in vitro or ex vivo diagnosis, prediction, prognosis and/or monitoring of a disease or condition characterized by an aberrant level of ACKR3 polypeptide, comprising the steps of obtaining a biological sample obtained from a subject, contacting said biological sample with the peptide as taught herein, wherein said peptide is fused to a detectable label, determining the level of ACKR3 polypeptide in said biological sample by detecting the peptide as taught herein, and diagnosing, predicting, prognosing and/or monitoring the disease or condition based on the level of ACKR3 protein.

The term "in vitro" generally denotes outside, or external to, a body, e.g., an animal or human body.

The term also encompasses "ex vivo". One example of "in vitro" is in tissue cell culture.

The terms "sample" or "biological sample" as used herein include any biological specimen obtained and isolated from a subject. Samples may include, without limitation, organ tissue (i.e., tumour tissue, more particular breast tumour tissue), whole blood, plasma, serum, whole blood cells, red blood cells, white blood cells (e.g., peripheral blood mononuclear cells), saliva, urine, stool (i.e., faeces), tears, sweat, sebum, nipple aspirate, ductal lavage, tumour exudates, synovial fluid, cerebrospinal fluid, lymph, fine needle aspirate, amniotic fluid, any other bodily fluid, cell lysates, cellular secretion products, inflammation fluid, semen and vaginal secretions. Preferably, a sample may be readily obtainable by minimally invasive methods, such as blood collection or tissue biopsy, allowing the removal/isolation/provision of the sample from the subject. The term "tissue" as used herein encompasses all types of cells of the human body including cells of organs but also including blood and other body fluids recited above.

The term "contact" or "contacting" as used herein means bringing one or more first components (such as one or more molecules, biological entities, cells, or materials) together with one or more second components (such as one or more molecules, biological entities, cells, or materials) in such a manner that the first component(s) can—if capable thereof—bind or modulate the second component(s) or that the second component(s) can—if capable thereof—bind or modulate the first component(s). Such modulation may occur either directly, i.e., by way of direct interaction between the first and second component(s); or indirectly, e.g., when the first component(s) interact with or modulate one or more further component(s), one or more of which in turn interact with or modulate the second component(s), or vice versa. The term "contacting" may depending on the context be synonymous with "exposing", "incubating", "mixing", "reacting", "treating", or the like.

In particular embodiments, the peptide as taught herein for use or the method may comprise a step of comparing the level of ACKR3 polypeptide in a biological sample from a subject with a given reference value; finding a deviation or no deviation between the level of ACKR3 polypeptide in the biological sample from the subject and the reference value; and attributing said finding of a deviation or no deviation to a particular diagnosis, prediction or prognosis of the disease or condition characterized by aberrant levels of ACKR3 polypeptide.

Such comparison may generally include any means to determine the presence or absence of at least one difference and optionally of the size of such difference between values or profiles being compared. A comparison may include a visual inspection, an arithmetical or statistical comparison of measurements. Such statistical comparisons include, but are not limited to, applying an algorithm.

Reference values for the level of ACKR3 polypeptide may be established according to known procedures previously employed for other biomarkers. For example, a reference value of the amount of ACKR3 polypeptide for a particular diagnosis, prediction, prognosis and/or monitoring of a proliferative disease as taught herein may be established by determining the quantity or expression level of ACKR3 polypeptide in sample(s) from one individual or from a population of individuals characterised by said particular diagnosis, prediction, prognosis and/or monitoring of said disease or condition. Such population may comprise without limitation $\geq 2$, $\geq 10$, $\geq 100$, or even several hundred individuals or more.

The skilled person will understand that the reference value is dependent on whether diagnosis, prediction, prognosis and/or monitoring of a disease or condition characterized by an aberrant level of ACKR3 polypeptide is envisioned. For instance, distinct reference values may represent the diagnosis of a disease or condition characterized by an aberrant level of ACKR3 polypeptide vs. the absence of a disease or condition characterized by an aberrant level of ACKR3 polypeptide (such as, e.g., healthy or recovered from a disease or condition characterized by an aberrant level of ACKR3 polypeptide).

A "deviation" of a first value from a second value may generally encompass any direction (e.g., increase: first value>second value; or decrease: first value<second value) and any extent of alteration. Preferably, a deviation may refer to a statistically significant observed alteration. For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

In a further embodiment, a deviation may be concluded if an observed alteration is beyond a given threshold or cut-off. Such threshold or cut-off may be selected as generally known in the art to provide for a chosen sensitivity and/or specificity of the prediction methods.

In the methods provided herein the observation of a deviation between the ACKR3 polypeptide level in a biological sample from a subject and a reference value can lead to the conclusion that the diagnosis, prediction and/or prognosis of said proliferative disease in said subject is different from that represented by said reference value. Similarly, when no deviation is found between the quantity or expression level of the ACKR3 polypeptide level in a biological sample from a subject and a reference value, the absence of such deviation can lead to the conclusion that the diagnosis, prediction and/or prognosis of said proliferative disease in said subject is substantially the same as that represented by said reference value.

The ACKR3 polypeptide is preferentially expressed in cancer cells over normal (non-cancer) cells.

Accordingly, in particular embodiments, the disease characterized by aberrant level of ACKR3 polypeptide is a proliferative disease, preferably a cancer, more preferably a cancer selected from the group consisting of carcinomas, gliomas, mesotheliomas, melanomas, lymphomas, leukemias, adenocarcinomas, breast cancer, ovarian cancer, cervical cancer, glioblastoma, prostate cancer, Burkitt's lymphoma, head and neck cancer, colon cancer, colorectal cancer, non-small cell lung cancer, small cell lung cancer, cancer of the oesophagus, stomach cancer, pancreatic cancer, hepatobiliary cancer, cancer of the gallbladder, cancer of the small intestine, rectal cancer, kidney cancer, bladder cancer, penile cancer, urethral cancer, testicular cancer, vaginal cancer, uterine cancer, thyroid cancer, parathyroid cancer, adrenal cancer, pancreatic endocrine cancer, carcinoid cancer, bone cancer, skin cancer, retinoblastomas, Hodgkin's lymphoma, and non-Hodgkin's lymphoma. In further particular embodiments, the disease characterized by aberrant level of ACKR3 polypeptide is fibrosis. In further particular embodiments, the disease characterized by aberrant level of ACKR3 polypeptide is atherosclerosis or atherosclerotic plaque formation.

A further aspect of the invention relates to a kit for diagnosing, predicting, prognosing and/or monitoring a disease or condition characterized by an aberrant level of ACKR3 polypeptide in a subject, the kit comprising:

(a) a peptide as taught herein, preferably wherein said peptide is fused to a detectable label; and (b) a reference value of the level of ACKR3 polypeptide, wherein said reference value represents a known diagnosis, prediction and/or prognosis of the disease or condition characterized by an aberrant level of ACKR3 polypeptide, such as wherein said reference value corresponds to the level of ACKR3 polypeptide in a tissue not affected by the disease or condition characterized by an aberrant level of ACKR3 polypeptide, such as in a healthy tissue, or wherein said reference value corresponds to the level of ACKR3 polypeptide in a tissue affected by the disease or condition characterized by an aberrant level of ACKR3 polypeptide.

The kit for diagnosing, predicting, prognosing and/or monitoring a disease or condition characterized by an aberrant level of ACKR3 polypeptide in a subject may further comprise ready-to use substrate solutions, wash solutions, dilution buffers and instructions. The diagnostic kit may also comprise positive and/or negative control samples.

Preferably, the instructions included in the diagnostic kit are unambiguous, concise and comprehensible to those skilled in the art. The instructions typically provide information on kit contents, how to collect the tissue sample, methodology, experimental read-outs and interpretation thereof and cautions and warnings.

In particular embodiments, the kit further comprises means for detecting said peptide as taught herein.

The means for measuring the level of ACKR3 polypeptide in a tissue sample from a subject may comprise binding agents as discussed elsewhere in this specification and/or carriers which allow visualization and/or a qualitative read-out of the measurement, for example, by spectrophotometry. Optionally, these carriers allow for cascade testing. Non-limiting examples of carriers are translucent microtiter plates, translucent stripwells or translucent tubes.

A further aspect provides an in vitro method for identifying an agent useful as a therapeutic, said method comprising determining whether a test agent is capable of modulating (i.e. inducing or inhibiting) $\beta$-arrestin-1 and/or $\beta$-arrestin-2 recruitment to the ACKR3 polypeptide.

A further aspect provides an in vitro method for identifying an agent useful as a therapeutic, said method comprising determining whether a test agent is capable of inducing $\beta$-arrestin-1 and/or $\beta$-arrestin-2 recruitment to the ACKR3 polypeptide and is not capable of inducing $\beta$-arrestin-1 and/or $\beta$-arrestin-2 recruitment to any other receptor polypeptide, such as to any opioid receptor polypeptide selected from the group consisting of the MOR, DOR, KOR and NOP receptor, or to any chemokine receptor polypeptide selecting from the group consisting of CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 or ACKR4.

The term "test agent" as used herein refers to any chemical (e.g., inorganic or organic), biochemical or biological substance, molecule or macromolecule (e.g., biological macromolecule), a combination or mixture thereof, a sample of undetermined composition, or an extract made from biological materials such as bacteria, fungi, plants, or animal cells or tissues of which it is desired to determine whether it specifically binds and activates the ACKR3 polypeptide.

Determining the induction (or absence thereof) of $\beta$-arrestin-1 and/or $\beta$-arrestin-2 recruitment to the ACKR3, MOR, DOR, KOR, NOP, CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 or ACKR4 polypeptide may be determined as described elsewhere herein.

When reference is made herein to β-arrestin-1 and/or β-arrestin-2 recruitment to a receptor, it indicates the recruitment of β-arrestin-1 and/or β-arrestin-2 recruitment to a receptor, induced by or mediated by binding of an agent to the same receptor. Hence, it does not encompass any indirect effects on other receptors resulting from binding of the agent to the receptor, for instance, as a result of the scavenger function of a receptor. For instance, β-arrestin-1 and/or β-arrestin-2 recruitment to the MOR polypeptide, does not encompass the β-arrestin-1 and/or β-arrestin-2 recruitment to the MOR polypeptide as a result from binding of the peptide as taught herein to the ACKR3 receptor, resulting in an increased availability of the endogenous opioid peptides to the MOR polypeptide.

In particular embodiments, the in vitro method for identifying an agent useful as a therapeutic as disclosed herein comprises contacting the test agent with a cell capable of β-arrestin-1 and β-arrestin-2 recruitment to the ACKR3 polypeptide, and selectively measuring said β-arrestin-1 and/or β-arrestin-2 recruitment to the ACKR3 polypeptide, and contacting the test agent with a cell capable of β-arrestin-1 and/or β-arrestin-2 recruitment to the MOR, DOR, KOR, NOP, CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 and/or ACKR4 polypeptide(s), and selectively measuring said β-arrestin-1 and/or β-arrestin-2 recruitment to the MOR, DOR, KOR, NOP, CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 and/or ACKR4 polypeptide(s).

Selectively measuring β-arrestin-1 and/or β-arrestin-2 recruitment to a certain receptor can be performed as elsewhere described herein. For instance, selectively measuring β-arrestin-1 and/or β-arrestin-2 recruitment to the ACKR3 polypeptide can be performed using ACKR3 C-terminally fused to SmBiT and the β-arrestin N-terminally fused to LgBiT. Likewise, selectively measuring β-arrestin-1 and/or β-arrestin-2 recruitment to the MOR, DOR, KOR, NOP, CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 or ACKR4 polypeptide can be performed using the MOR, DOR, KOR, NOP, CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 or ACKR4 polypeptide C-terminally fused to SmBiT and the β-arrestin N-terminally fused to LgBiT. Alternatively, the ACKR3, MOR, DOR, KOR, NOP, CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 or ACKR4 polypeptide can be C-terminally fused to LgBiT and the β-arrestin can be C-terminally or N-terminally fused to SmBiT. In these examples, the interaction between the SmBiT-tagged receptor polypeptide and the LgBiT-tagged β-arrestin, or alternatively between the SmBiT-tagged β-arrestin and the LgBiT-tagged receptor polypeptide is determined.

Cells capable of β-arrestin-1 and β-arrestin-2 recruitment to the ACKR3 receptor are typically cells that comprise β-arrestin-1 and β-arrestin-2 in their cytosol and express ACKR3 polypeptide at their plasma membrane. Cells capable of β-arrestin-1 and β-arrestin-2 recruitment to the MOR, DOR, KOR and/or NOP receptor are typically cells that comprise β-arrestin-1 and β-arrestin-2 in their cytosol and express MOR, DOR, KOR and/or NOP polypeptide at their plasma membrane. Cells capable of β-arrestin-1 and -arrestin-2 recruitment to the CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 and/or ACKR4 receptor are typically cells that comprise f-arrestin-1 and β-arrestin-2 in their cytosol and express CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 and/or ACKR4 polypeptide at their plasma membrane.

In particular embodiments, when selectively measuring β-arrestin-1 and/or β-arrestin-2 recruitment to a certain receptor by nanoluciferase complementation assays (e.g. NanoBiT, Promega), the cells capable of β-arrestin-1 and β-arrestin-2 recruitment to the ACKR3 receptor are typically cells that express LgBiT-tagged or SmBiT-tagged β-arrestin-1 and/or LgBiT-tagged or SmBiT tagged β-arrestin-2 in their cytosol and express SmBiT-tagged or LgBiT-tagged ACKR3 polypeptide at their plasma membrane. Cells capable of β-arrestin-1 and β-arrestin-2 recruitment to the MOR, DOR, KOR and/or NOP receptor are typically cells that comprise LgBiT-tagged or SmBiT-tagged β-arrestin-1 and/or LgBiT-tagged or SmBiT-tagged β-arrestin-2 in their cytosol and express SmBiT-tagged or LgBiT-tagged MOR, DOR, KOR and/or NOP polypeptide at their plasma membrane. Cells capable of β-arrestin-1 and β-arrestin-2 recruitment to the CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 and/or ACKR4 receptor are typically cells that comprise LgBiT-tagged or SmBiT-tagged β-arrestin-1 and/or LgBiT-tagged or SmBiT-tagged β-arrestin-2 in their cytosol and express SmBiT-tagged or LgBiT-tagged CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 and/or ACKR4 polypeptide at their plasma membrane. The skilled person will understand that, in present embodiment, if β-arrestin-1 and/or β-arrestin-2 is tagged by LgBiT, the receptor polypeptide will have to be tagged by SmBiT, and vice versa. As described elsewhere herein, the absence of, or the not comprising or containing of, a receptor polypeptide does in this context not per se refer to the complete absence of said receptor polypeptide at the cell membrane, but may refer to an amount of the receptor polypeptide which is not detectable by, or falls below the sensitivity range of, protein assays known by the person skilled in the art.

Preliminary screens can be conducted by screening the test agent for its capability of binding to ACKR3 polypeptide.

In particular embodiments, the in vitro method for identifying an agent useful as a therapeutic as disclosed herein comprises determining whether the test agent is capable of binding to the ACKR3 polypeptide, and optionally determining whether the test agent is capable of binding to any other receptor polypeptide, such as the MOR, DOR, KOR, NOP, CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 and/or ACKR4 polypeptide.

The binding assay may involve contacting a ACKR3 polypeptide, a MOR polypeptide, a DOR polypeptide, a KOR polypeptide, a NOP polypeptide, a CCR1 polypeptide, a CCR2A polypeptide, a CCR2B polypeptide, a CCR3 polypeptide, a CCR4 polypeptide, a CCR5 polypeptide, a CCR6 polypeptide, a CCR7 polypeptide, a CCR8 polypeptide, a CCR9 polypeptide, a CCR10 polypeptide, a CXCR1 polypeptide, a CXCR2 polypeptide, a CXCR3A polypeptide, a CXCR3B polypeptide, a CXCR4 polypeptide, a CXCR5 polypeptide, a CXCR6 polypeptide, a CXCR8 polypeptide, a XCR1 polypeptide, a CX3CR1 polypeptide, a ACKR1 polypeptide, a ACKR2 polypeptide or a ACKR4 polypeptide with the test agent and allowing sufficient time for the test agent and the ACKR3 polypeptide, the MOR polypeptide, the DOR polypeptide, the KOR polypeptide, the NOP polypeptide, the CCR1 polypeptide, the CCR2A polypeptide, the CCR2B polypeptide, the CCR3 polypeptide, the CCR4 polypeptide, the CCR5 polypeptide, the CCR6 polypeptide, the CCR7 polypeptide, the CCR8 polypeptide, the CCR9 polypeptide, the CCR10 polypeptide, the CXCR1 polypeptide, the CXCR2 polypeptide, the CXCR3A polypeptide, the CXCR3B polypeptide, the CXCR4 polypeptide, the CXCR5 polypeptide, the CXCR6 polypeptide, the CXCR8 polypeptide, the XCR1 polypeptide, the CX3CR1 polypeptide, the ACKR1 polypeptide, the ACKR2 polypeptide or the ACKR4 polypeptide to form a binding complex. Formation of a binding complex may be detected using any established analytical technique for determining protein-protein binding, such as binding competition assays using fluorescently labelled or radiolabelled ligands (e.g. fluorescently labelled or radiolabelled chemokines, such as CXCL12), co-immunoprecipitation, bimolecular fluorescence complementation, label transfer, tandem affinity purification, chemical cross-linking and fluorescence resonance energy transfer. Protein binding assays may be performed in a cell-free system or in a cell lysate or in isolated or cultured cells or in an isolated or cultured tissue.

In a binding assay, one or more of the agent, the ACKR3 polypeptide, the MOR polypeptide, the DOR polypeptide, the KOR polypeptide, the NOP polypeptide, the CCR1 polypeptide, the CCR2A polypeptide, the CCR2B polypeptide, the CCR3 polypeptide, the CCR4 polypeptide, the CCR5 polypeptide, the CCR6 polypeptide, the CCR7 polypeptide, the CCR8 polypeptide, the CCR9 polypeptide, the CCR10 polypeptide, the CXCR1 polypeptide, the CXCR2 polypeptide, the CXCR3A polypeptide, the CXCR3B polypeptide, the CXCR4 polypeptide, the CXCR5 polypeptide, the CXCR6 polypeptide, the CXCR8 polypeptide, the XCR1 polypeptide, the CX3CR1 polypeptide, the ACKR1 polypeptide, the ACKR2 polypeptide and/or the ACKR4 polypeptide may be joined to a label, where the label can directly or indirectly provide a detectable signal. Non-limiting examples of such labels or signals include radioisotopes, fluorescent labels or signals, chemiluminescent labels or signals, enzymes, specific binding molecules, or particles (e.g. magnetic particles).

In particular embodiments, the in vitro method for identifying an agent useful as a therapeutic as disclosed herein may further comprise the use of one or more reagents which improve the efficiency of the assay, facilitate optimal protein-protein binding and/or reduce non-specific or background interactions. Non-limiting examples of such reagents are salts, neutral proteins (e.g. albumin), detergents, protease inhibitors, nuclease inhibitors, and anti-microbial agents.

In particular embodiments, the level of β-arrestin-1 and/or β-arrestin-2 recruitment to the ACKR3 polypeptide induced by the test agent may be compared to the level of β-arrestin-1 and/or β-arrestin-2 recruitment to the ACKR3 polypeptide induced by the peptide as taught herein.

In particular embodiments, the binding affinity of the test agent to the ACKR3 polypeptide may be compared to binding affinity of the peptide as taught herein the ACKR3 polypeptide.

In particular embodiments, test agent may be identified as an agent useful as a therapeutic as disclosed herein if the agent induces at least 1.5-fold more, at least 2-fold more, at least 2.5-fold more, at least 3-fold more, at least 4.5-fold more, at least 5-fold more, at least 6-fold more, at least 7-fold more, at least 8-fold more, at least 9-fold more, at least 10-fold more, at least 20-fold more, or at least 30-fold more β-arrestin-1 and/or β-arrestin-2 recruitment to the ACKR3 polypeptide compared to the baseline β-arrestin-1 and/or β-arrestin-2 recruitment or background β-arrestin-1 and/or β-arrestin-2 recruitment to the ACKR3 polypeptide induced by a neutral substance or negative control, for example as measured in an assay as described elsewhere herein.

In particular embodiments, test agent may be identified as an agent useful as a therapeutic as disclosed herein:

if the agent induces β-arrestin-1 and/or β-arrestin-2 recruitment to the ACKR3 polypeptide which is equal to or higher than, such as at least 1.1-fold more, at least 1.2-fold more, at least 1.3-fold more, at least 1.4-fold more, at least 1.5-fold more, at least 2-fold more, at least 2.5-fold more, at least 3-fold more, at least 4.5-fold more, at least 5-fold more, at least 6-fold more, at least 7-fold more, at least 8-fold more, at least 9-fold more, at least 10-fold more, at least 20-fold more, or at least 30-fold more the β-arrestin-1 and/or β-arrestin-2 recruitment to the ACKR3 polypeptide induced by the peptide as taught herein, for example as measured in an assay as described elsewhere herein; and/or if the agent binds to the ACKR3 polypeptide with an affinity which is equal to or higher than, such as at least 1.1-fold more, at least 1.2-fold more, at least 1.3-fold more, at least 1.4-fold more, at least 1.5-fold more, at least 2.-fold more, at least 2.5-fold more, at least 3-fold more, at least 4.5-fold more, at least 5-fold more, at least 6-fold more, at least 7-fold more, at least 8-fold more, at least 9-fold more, at least 10-fold more, at least 20-fold more, or at least 30-fold more the binding affinity of the peptide as taught herein to the ACKR3 polypeptide.

The selective ACKR3 modulating peptide as taught herein can be used in competitive binding studies for identifying ACKR3 antagonists or positive/negative allosteric modulators. For example, ACKR3 can be pre-treated with a test agent before exposing ACKR3 to the selective ACKR3 modulating peptide as taught herein. If β-arrestin-1 and/or β-arrestin-2 recruitment to the ACKR3 polypeptide upon exposure to the selective ACKR3 modulating peptide as taught herein is inhibited, the test agent can be identified as an antagonist or positive/negative allosteric modulators of the ACKR3 polypeptide Accordingly, a further aspect provides an in vitro method for identifying an agent useful as a therapeutic, said method comprising determining whether a test agent is capable of modulating, preferably inhibiting, β-arrestin-1 and/or β-arrestin-2 recruitment to the ACKR3 polypeptide by the selective ACKR3 modulating peptide as taught herein.

In particular embodiments, the in vitro method for identifying an agent useful as a therapeutic as disclosed herein comprises determining whether the test agent is capable of binding specifically to the ACKR3 polypeptide.

Present inventors found that ACKR3 acts as a scavenger for endogenous opioid peptides, regulating the local and/or systemic concentrations and thus availability for the classical opioid receptors.

Accordingly, all agents specifically binding to the ACKR3 polypeptide and/or specifically inducing β-arrestin-1 and/or β-arrestin-2 recruitment to the ACKR3 polypeptide could be used to regulate the availability of endogenous opioid peptides for other opioid receptors, including the MOR, KOR, DOR and NOP polypeptides.

Accordingly, a further aspect provides a therapeutic or prophylactic agent for use in the treatment of a distress dysfunction disease or condition in a subject, wherein said therapeutic or prophylactic agent is capable of modulating (e.g. inducing or antagonizing), preferably capable of inducing, β-arrestin-1 and/or β-arrestin-2 recruitment to the ACKR3 polypeptide and is not capable of inducing β-arrestin-1 and/or β-arrestin-2 recruitment to any other receptor polypeptide, including any opioid receptor polypeptide selected from the group consisting of the MOR, DOR, KOR and NOP receptor, and any chemokine receptor polypeptide selecting from the group consisting of CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 and ACKR4.

The terms "treat" or "treatment" encompass both the therapeutic treatment of an already developed disease or condition, as well as prophylactic or preventive measures, wherein the aim is to prevent or lessen the chances of incidence of an undesired affliction. Beneficial or desired clinical results may include, without limitation, alleviation of one or more symptoms or one or more biological markers, diminishment of extent of disease, stabilised (i.e., not worsening) state of disease, delay or slowing of disease progression, amelioration or palliation of the disease state, and the like. "Treatment" can also mean prolonging survival as compared to expected survival if not receiving treatment.

In particular embodiments, distress dysfunction disease or condition is selected from the group consisting of anxiety disorders, depression, anger, insomnia, mood disorders, substance and behavioural addictions (e.g. opiate, cocaine or alcohol abuse and/or dependence), and eating disorders (e.g. anorexia). In preferred embodiments, the distress dysfunction disease or condition is selected from the group consisting of anxiety disorders and depression.

In particular embodiments, the therapeutic or prophylactic agent is selected from the group consisting of a chemical substance, an antibody, an antibody fragment, an antibody-like protein scaffold, a protein or polypeptide, a peptide, a peptidomimetic, an aptamer, a photoaptamer, a spiegelmer and a nucleic acid, preferably wherein said agent is a protein or polypeptide or peptide.

Methods for determining whether the agent is capable of inducing β-arrestin-1 and/or β-arrestin-2 recruitment to the ACKR3 polypeptide, and is not capable of inducing β-arrestin-1 and/or β-arrestin-2 recruitment to any other receptor polypeptide, including any opioid receptor polypeptide selected from the group consisting of the MOR, DOR, KOR and NOP receptor, and any chemokine receptor polypeptide selecting from the group consisting of CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR5, XCR1, CX3CR1, ACKR1, ACKR2 and ACKR4 are known by the person skilled in the art, as described elsewhere herein.

A related aspect provides a method for treating a distress dysfunction disease or condition in a subject comprising administering a therapeutically and/or prophylactically effective amount of a therapeutic or prophylactic agent to said subject, wherein said therapeutic or prophylactic agent is capable of inducing β-arrestin-1 and/or β-arrestin-2 recruitment to the ACKR3 polypeptide, and is not capable of inducing β-arrestin-1 and/or β-arrestin-2 recruitment to any other receptor polypeptide, including any opioid receptor polypeptide selected from the group consisting of the MOR, DOR, KOR and NOP receptor, and any chemokine receptor polypeptide selecting from the group consisting of CCR1, CCR2A, CCR2B, CCR3, CCR4, CCR5, CCR6, CCR7, CCR5, CCR9, CCR10, CXCR1, CXCR2, CXCR3A, CXCR3B, CXCR4, CXCR5, CXCR6, CXCR8, XCR1, CX3CR1, ACKR1, ACKR2 and ACKR4.

The term "therapeutically effective amount" as used herein, refers to an amount of therapeutic agent that elicits the biological or medicinal response in a subject that is being sought by a surgeon, researcher, veterinarian, medical doctor or other clinician, which may include inter alia alleviation of the symptoms of the disease or condition being treated. The term "prophylactically effective amount" refers to an amount of the prophylactic agent that inhibits or delays in a subject the onset of a disorder as being sought by a researcher, veterinarian, medical doctor or other clinician. Methods are known in the art for determining therapeutically and/or prophylactically effective amounts of the therapeutic or prophylactic agent as described herein.

The peptide as taught herein can be used in the treatment of diseases or conditions that are, at least in part, dependent on ACKR3 activity.

ACKR3 acts as a scavenger for chemokines, regulating the local and/or systemic concentrations and thus availability for the other chemokine receptors. Accordingly, the peptide as taught herein could be used to regulate the availability of endogenous (such as CXCL11 or CXCL12) or exogenous (such as vCCL2 (vMIP-II)) chemokines for other chemokine receptors, including the CCR1, CCR2A, CCR2B, CCR3, CCR4, CCR5, CCR6, CCR7, CCR8, CCR9, CCR10, CXCR1, CXCR2, CXCR3A, CXCR3B, CXCR4, CXCR5, CXCR6, CXCR8, XCR1, CX3CR1, ACKR1, ACKR2 and ACKR4 polypeptides.

As a result thereof, the peptide as taught herein, the fusion protein as taught herein, the nucleic acid encoding the agent or fusion protein as taught herein, the nucleic acid expression cassette as taught herein, the vector as taught herein or the pharmaceutical composition as taught herein could be used in the treatment of diseases or conditions in which these endogenous or exogenous chemokines play a role.

Accordingly, a further aspect provides the peptide as taught herein, the fusion protein as taught herein, the nucleic acid encoding the agent or fusion protein as taught herein, the nucleic acid expression cassette as taught herein, the vector as taught herein or the pharmaceutical composition as taught herein for use as a medicament.

ACKR3 plays a key role in controlling the angiogenic process, for example, in cancers. Accordingly, the present invention encompasses decreasing angiogenesis in any subject in need thereof (e.g. subject having a disease or condition involving excessive or abnormal angiogenesis) by administering the peptide as taught herein.

A further aspect provides the peptide as taught herein, the fusion protein as taught herein, the nucleic acid encoding the agent or fusion protein as taught herein, the nucleic acid expression cassette as taught herein, the vector as taught herein or the pharmaceutical composition as taught herein for use in the treatment of a disease or condition selected from the group consisting of distress dysfunction diseases or conditions, cancers, atherosclerotic vascular disease (or atherosclerosis), cardiovascular diseases, fibrosis (e.g. cardiac fibrosis), inflammatory or autoimmune diseases and conditions, conditions of excessive or abnormal vascularization (e.g. wound healing and HIV infectivity), stem cell differentiation and mobilization disorders, brain and neuronal dysfunctions (e.g. Alzheimer's disease, multiple sclerosis and demyelinating diseases), kidney dysfunction, renal dysfunction, preeclampsia and obesity, preferably a disease or condition selected from the group consisting of distress dysfunction diseases or conditions, cancers, atherosclerotic vascular disease, cardiovascular diseases and fibrosis, in a subject.

Non-limiting examples of inflammatory or autoimmune diseases and conditions include inflammatory bowel disease, rheumatoid arthritis, osteoarthritis, psoriatic arthritis, polyarticular arthritis, renal inflammatory disorders, multiple sclerosis, colitis, allergic diseases, psoriasis, atopic dermatitis and asthma. A related aspect provides a method for treating a disease or condition selected from the group consisting of distress dysfunction diseases or conditions, cancers, atherosclerotic vascular disease (or atherosclerosis), cardiovascular diseases, fibrosis (e.g. cardiac fibrosis), inflammatory or autoimmune diseases and conditions, conditions of excessive or abnormal vascularization (e.g. wound healing and HIV infectivity), stem cell differentiation and mobilization disorders, brain and neuronal dysfunctions (e.g. Alzheimer's disease, multiple sclerosis and demyelinating diseases), kidney dysfunction, renal dysfunction, preeclampsia and obesity, preferably a disease or condition selected from the group consisting of distress dysfunction diseases or conditions, cancers, atherosclerotic vascular disease, cardiovascular diseases and fibrosis, in a subject comprising administering a therapeutically and/or prophylactically effective amount of the peptide as taught herein, the fusion protein as taught herein, the nucleic acid encoding the agent or fusion protein as taught herein, the nucleic acid expression cassette as taught herein, the vector as taught herein or the pharmaceutical composition as taught herein to said subject.

A further aspect provides the use of the peptide as taught herein, the fusion protein as taught herein, the nucleic acid encoding the agent or fusion protein as taught herein, the nucleic acid expression cassette as taught herein, the vector as taught herein or the pharmaceutical composition as taught herein for reducing tumour cell proliferation, tumour formation, tumour vascularization and metastasis. A further aspect provides the use of the peptide as taught herein, the fusion protein as taught herein, the nucleic acid encoding the agent or fusion protein as taught herein, the nucleic acid expression cassette as taught herein, the vector as taught herein or the pharmaceutical composition as taught herein for increasing T cell recruitment in a subject.

A further aspect provides the use of the peptide as taught herein, the fusion protein as taught herein, the nucleic acid encoding the agent or fusion protein as taught herein, the nucleic acid expression cassette as taught herein, the vector as taught herein or the pharmaceutical composition as taught herein for reducing viral reproduction in a subject.

In particular embodiment, the peptide as taught herein, the fusion protein as taught herein, the nucleic acid encoding the agent or fusion protein as taught herein, the nucleic acid expression cassette as taught herein, the vector as taught herein or the pharmaceutical composition as taught herein are used in combination with agents known to be used in the treatment of the diseases or conditions listed above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The herein disclosed aspects and embodiments of the invention are further supported by the following non-limiting examples.

EXAMPLES

Example 1. Material and Methods Used for Examples 2 to 7

1.1. Peptides and Chemokines

Non-labelled chemokines CXCL12, CXCL11 and vCCL2 were purchased from PeproTech. Alexa Fluor 647-labelled CXCL12 (CXCL12-AF647) was purchased from Almac. The opioid peptide library and all opioid peptides as well as FAM-labelled Dynorphin A (1-13) and FAM-labelled nociceptin were acquired from Phoenix Pharmaceuticals. BAM22 and big dynorphin labelled with Cy5 were generated using an Amersham QuickStain Cy5 kit for proteins according to manufacturer's protocol. Adrenorphin-derived peptides were synthesised by JPT. These peptides contain a free amine at the N terminus and an amide group at the C terminus to avoid additional negative charge. Besides Levallorphan, which was purchased from Sigma, all non-peptide opioids were obtained from Tocris.

1.2. Cell Culture

U87 cells derived from human brain glioblastoma were obtained through the NIH AIDS Reagent Program from Dr. Deng and Dr. Littman. U87 stably expressing ACKR3 and CXCR4 were generated as previously described in Szpakowska, M. et al. Different contributions of chemokine N-terminal features attest to a different ligand binding mode and a bias towards activation of ACKR3/CXCR7 compared with CXCR4 and CXCR3. *Br J Pharmacol* 175, 1419-1438 (2018). U87 cells were grown in Dulbecco's modified Eagle medium (DMEM) supplemented with 15% foetal bovine serum and penicillin/streptomycin (100 Units/ml and 100 µg/ml). U87-ACKR3 and U87-CXCR4 were maintained under puromycin (1 µg/ml) selective pressure. smNPCs (small molecule neural precursor cells) derived from a healthy donor (C1-1) whose informed consent was obtained, were grown on Geltrex™-coated surface in N2B27 medium supplemented with 0.5 µM Purmorphamine, 3 µM CHIR 99021 and 150 µM ascorbic acid. N2B27 medium consisted of DMEM/F12 and NeuroBasal medium 50:50 with 0.5% N2 supplement, 1% B27 supplement lacking vitamin A, 1% GlutaMAX and 1% penicilin/streptomycin. Medium was renewed every other day.

1.3. Binding Competition Assays

U87-ACKR3 cells were distributed into 96-well plates ($1.5 \times 10^5$ cells per well) and incubated with a mixture of 5 nM CXCL12-AF647 and unlabelled chemokines or opioid peptides at indicated concentrations for 90 minutes on ice, then washed twice with FACS buffer (PBS, 1% BSA, 0.1% $NaN_3$) at 4° C. Dead cells were excluded using Zombie Green viability dye (BioLegend). ACKR3-negative U87 cells were used to evaluate non-specific binding of CXCL12-AF647. 0% receptor binding of CXCL12-AF647 was defined as the signal obtained after addition of 1 µM of unlabelled CXCL12. The signal obtained for CXCL12-AF647 in the absence of unlabelled chemokines was used to define 100% binding. Ligand binding was quantified by mean fluorescence intensity on a BD FACS Fortessa cytometer (BD Biosciences).

1.4. Nanoluciferase Complementation Assays

Ligand-induced β-arrestin recruitment to chemokine and opioid receptors was monitored by NanoLuc complementation assay (NanoBiT, Promega) as previously described in Szpakowska, M. et al. Mutational analysis of the extracellular disulphide bridges of the atypical chemokine receptor ACKR3/CXCR7 uncovers multiple binding and activation modes for its chemokine and endogenous non-chemokine agonists. *Biochem Pharmacol* 153, 299-309 (2018). In brief, $1.2 \times 10^6$ U87 cells were plated in 10 cm-culture dishes and 48 hours later co-transfected with pNBe vectors encoding GPCRs C-terminally tagged to SmBiT and human β-arrestin-1 or -2 or mini G proteins (mG, engineered GTPase domains of Gα subunits,) N-terminally fused to LgBiT. 48 hours post-transfection cells were harvested, incubated 25 minutes at 37° C. with Nano-Glo Live Cell substrate diluted 200-fold and distributed into white 96-well plates ($5 \times 10^4$ cells per well). Ligand-induced, β-arrestin and mG recruitment to GPCRs was evaluated with a Mithras LB940 luminometer (Berthold Technologies) for 20 minutes. For concentration-response curves, the signal recorded with a saturating concentration of full agonist for each receptor was set as 100%. To evaluate the antagonist properties of ligands, full agonists of each receptor (50 nM BAM22 for MOR, 50 nM dynorphin A for KOR, 70 nM met-enkephalin for DOR, 70 nM nociception for NOP and 4 nM CXCL12 for ACKR3) were added after the 20-minute incubation with the ligands. Signal from wells treated with full agonist only was defined as 0% inhibition and signals from wells treated with no agonist were used to set 100% inhibition. For dynorphin A scavenging experiments with U87 cells, $1.5 \times 10^5$ U87 or U87.ACKR3 cells were distributed per well in a white 96-well plate. After 15-minute incubation at 37° C. with 400 nM L1H383 or LIH383 control peptide, (200 nM CXCL12 or CXCL10), dynorphin A was added at concentrations ranging from 0.15 nM to 3 µM and incubated for 25 minutes at 37° C. $1.5 \times 10^4$U87 cells, cotransfected 48 hours before the experiment with SmBiT-tagged KOR and LgBiT-tagged β-arrestin-1 or mini Gi and pre-incubated for 25 minutes with Nano-Glo Live substrate were then added per well and signal was measured for 20 minutes. For dynorphin A scavenging experiments with smNPC, $2 \times 10^6$ smNPC were pretreated for 15 minutes with 1.5 µM LIH383 or LIH383 control peptide (300 nM CXCL12 or CXCL10) before 4-hour incubation with 3 µM dynorphin A. Cells were centrifuged and the activity of the remaining dynorphin A in serially diluted supernatants was determined on U87 cells expressing SmBiT-tagged KOR and LgBiT-tagged mini Gi protein.

1.5. Label-Free Dynamic Mass Redistribution (DMR) Assay

Dynamic mass redistribution (DMR) experiments were conducted using the Corning Epic (Corning) biosensor system as previously described in Schröder, R. et al. Deconvolution of complex G protein-coupled receptor signaling in live cells using dynamic mass redistribution measurements. *Nat Biotechnol* 28, 943-949 (2010) and Schröder, R. et al. Applying label-free dynamic mass redistribution technology to frame signaling of G protein-coupled receptors noninvasively in living cells. *Nat Protoc.* 6(11): 1748-1760 (2011). In brief, $6 \times 10^5$ U87 cells were seeded in 6-cm dishes. 24 hours later cells were transfected with pcDNA3.1-based expression plasmids coding for the respective chemokine (ACKR3, CXCR4) or opioid (KOR, NOP) receptors using polyethylenimine (PEI) reagent (Polysciences). 24 hours after transfection $1 \times 10^4$ cells per well were transferred to a 384-well Epic biosensor plate and incubated (37° C., 5% $CO_2$) overnight. Cells were then washed twice with Hanks' balanced salt solution (HBSS) (Life Technologies) containing 20 mM HEPES (Life Technologies) and subsequently incubated in the DMR-reader for 1.5 hours to achieve temperature equilibration (37° C.). Five minutes after equilibration of the baseline DMR traces, compounds were added to the biosensor plate. Alterations of ligand-induced DMR were monitored for at least 3000 seconds. Raw data were processed and analysed using GraphPad Prism 7.05 (GraphPad Inc). For quantification, negative and positive areas under the curve (AUC) between 0 and 3000 seconds were used.

1.6 Homogeneous Time-Resolved Fluorescence (HTRF)-Based Extracellular Signal Regulated Kinases 1 and 2 (ERK1/2) Phosphorylation Assays Homogeneous Time-Resolved Fluorescence (HTRF)-based phospho-ERK1/2 and total-ERK1/2 assays were performed using phospho-ERK1/2 (Thr202/Tyr204) and total-ERK1/2 cellular kits (Cisbio International). In short, for quantification of total and phosphorylated ERK1/2 protein, U87 cells stably expressing (or not) ACKR3 or CXCR4 were seeded at a density of $3.5 \times 10^4$ cells per well into 96-well poly-D-lysine (PDL)-coated microtiter plates (Sigma-Aldrich). After overnight incubation, cells were starved for 4 hours at 37° C. in serum-free medium. Cells were then stimulated for the indicated time intervals with chemokine or opioid ligands, respectively, before termination by replacement of supernatants with lysis buffer followed by 1.5 hours incubation on an orbital shaker. Lysates were transferred to white 384-well plates, and D2-labeled anti-phospho-ERK1/2 and $Eu^{3+}$-Cryptate-labelled anti-phospho-ERK1/2 antibodies were added to each well for phospho-ERK1/2 determination. D2-labeled anti-total-ERK1/2 and $Eu^{3+}$-Cryptate-labelled anti-total-ERK1/2 antibodies were added for quantification of total-ERK1/2 abundance. Following an incubation time of at least 2 hours (phospho-ERK1/2) or 24 hours (total-ERK1/2), time-resolved FRET signals were measured using the Mithras LB 940 multimode reader (Berthold Technologies) equipped with 320 nm excitation filter and 620 nm (donor) and 665 nm (acceptor) emission filters.

1.7. Transcriptional Nanoluciferase Reporter Assays

Activation of the MAPK/ERK signalling pathway was evaluated using a serum response element (SRE) Nanoluciferase reporter assay. Activation of calcium-dependent signalling pathways was evaluated using a Nuclear Factor of Activated T-cell response element (NFAT-RE) Nanoluciferase reporter assay. For both assays, $1.2 \times 10^6$ U87 cells were seeded in 10-cm dishes and 48 hours later co-transfected with the pNanoLuc/SRE or pNanoLuc/NFAT-RE vectors (Promega), containing the Nanoluciferase gene downstream of SRE or NFAT-RE, and pcDNA3.1 encoding the respective chemokine or opioid receptors. 24 hours later, $2.5 \times 10^4$ cells/well ($2.5 \times 10^5$ for smNPCs) were seeded in a white 96-well plate. 24 hours later, the medium was replaced by serum-free and phenol red-free DMEM (serum-free DMEM/F12 for smNPCs) and further incubated for two hours. Opioid peptides (500 nM), chemokines (200 nM) were then added to the cells and incubated for six hours. 30 nM phorbol 12-myristate 13-acetate (PMA), 10% FBS or 30 nM PMA, 1 uM ionomycin, 10% FBS were used as positive controls for SRE and NFAT-RE assays, respectively. Nano-Glo Live Cell substrate (Promega) was then added and luminescence was read over 20 minutes on a Mithras LB940 plate reader (Berthold technologies).

1.8. Visualization of Fluorescently Labelled Opioid Peptides Uptake by Imagestream Cells were distributed into 96-well plates ($2\times10^5$ cells/well in Opti-MEM for U87 and U87-ACKR3 and $3\times10^5$ cells/well in N2B27 medium for smNPCs). After 15-minute incubation at 37° C. with LIH383 (3 µM) or Opti-MEM only, FAM-labelled dynorphin A (1-13) (250 nM), BAM22-Cy5 (400 nM), big dynorphin-Cy5 (400 nM) or nociception-FAM (1 µM) was added, incubated for 40 minutes at 37° C. and washed twice with FACS buffer. For comparison of labelled opioid peptide-uptake by ACKR3 or classical opioid receptors, $1.2\times10^6$ U87 cells were seeded in 10-cm dishes and transfected 48 hours later with 4 µg pcDNA3.1 plasmid encoding ACKR3 or KOR, MOR or NOP. 48 hours post transfection, cells were harvested and treated as described above. Dead cells were excluded using Zombie NIR or Zombie Green viability dye (BioLegend) for FAM-labelled peptides and Cy5-labelled peptides, respectively. Images of $1\times10^4$ in-focus, living single cells were acquired with an ImageStream MKII imaging flow cytometer (Amnis) using 40× magnification (60× magnification for smNPCs). Samples were analysed using Ideas6.2 software. The number of spots per cell was determined using a mask-based software wizard.

1.9. Ex Vivo Rat Neuron Depolarization 1.9.1. Animals

Adult male Wistar rats (6 to 8-week old) were housed at room temperature in groups of three or four with a 12:12 hour light-dark cycle. All animals had access to ad libitum food and water. All procedures were carried out in accordance with guidelines of the European Communities Council Directive of 24 Nov. 1986 (86609EE) and were accepted by the Ethics Committee for Animal Use of the University of Liège (protocol 2061). All efforts were made to minimize animal suffering.

1.9.2. Brain Explant Preparation and Recording Procedures

Rats were anaesthetized with chloral hydrate (400 mg/kg, i.p.) and placed under a cap with oxygenated air (95% $O_2$, 5% $CO_2$) two minutes prior to decapitation. After decapitation, the brain was rapidly removed and placed in ice cold (~2° C.) oxygenated artificial cerebrospinal fluid (aCSF) of the following composition: NaCl 130 mM, KCl 3.5 mM, $NaH_2PO_4$ 1.25 mM, $NaHCO_3$ 24 mM, Glucose 10 mM, $CaCl_2$ 2 mM, $MgSO_4$ 1.25 mM. A block of tissue containing the pons was placed in a vibrating blade microtome (Vibratome 1000 Plus, Sectioning System) and a slice containing the locus coeruleus (LC) immediately rostral to the fourth ventricle and the VIIth nerve, used as anatomical landmarks, was cut coronally (400 µm thick). The slice was placed on a nylon mesh in a recording chamber (volume: 0.5 ml) where it was superfused by oxygenated aCSF (34.0±0.5° C.) at a rate of 2 to 3 ml/min. The LC was recognized as a translucent region during transillumination, lateral to the fourth ventricle. All experiments were performed in oxygenated aCSF with synaptic blockers consisting of 10 µM CNQX, 10 µM SR95531, 1 µM MK801, and 1 µM CGP55845, which block AMPA/Kainate, GABAA, NMDA, and GABAB receptors, respectively. This ensured that the spontaneous firing of the neurons was only due to its endogenous pace making.

Extracellular single cell recordings of LC neurons were performed with glass microelectrodes filled with aCSF (resistance 10-20 MΩ). Signals were passed through an impedance adapter and were amplified 1000× using a home-made amplifier. They were displayed on a Fluke Combiscope oscilloscope and fed to an analog-digital interface (CED 1401, Cambridge Electronic Design, Cambridge, UK) connected to a computer. Data were collected and analysed with the Spike 2 software (Cambridge Electronic Design). All recorded neurons had a firing rate of 0.5 to 3 Hz with a good regularity (coefficient of variation of the interspike interval was 0.13±0.01, N=18) and a cessation of firing during application of the α2-adrenergic receptor agonist clonidine (10-20 nM). The duration of the extracellularly recorded action potentials was 2-3 ms. Drugs and peptides were applied for at least 10 minutes.

The mean firing rate over 1 minute was calculated during each condition. Next, the inhibition of firing by the peptides and drugs used (LIH383 and dynorphin) was quantified as the % of total inhibition. For this purpose, present inventors considered the mean firing rate during the last minute of each condition (control, LIH383 alone, LIH383 plus a given concentration of dynorphin). The $EC_{50}$ of dynorphin was obtained using the Hill equation ($E/E_{max}$=[dynorphin]/$EC_{50}$ (dynorphin)+[dynorphin] in GraphPad Prism (version 6). Individual values of the $EC_{50}$ values in the different conditions were compared using a Kruskal-Wallis test. One aberrant value (in the LIH383 3 µM group: 559 nM, which was >2SD away from the mean value for this group) was omitted.

1.10. RNA Extraction and Quantitative PCR on Human Brain Samples and smNPCs

Post-mortem samples from six brain regions of five patients suffering lethal non-head trauma were collected within 2-10 hours of death as reported in Cao-Lei, L. et al. Glucocorticoid receptor gene expression and promoter CpG modifications throughout the human brain. *J Psychiatr Res* 47, 1597-1607 (2013). Total RNA was extracted from biopsies using the AllPrep DNA/RNA mini kit (Qiagen) or from smNPC using RNeasy mini kit (Quiagen) and stored at −80° C. until cDNA synthesis. First-strand synthesis was performed in a two-step process. Initially samples were incubated with RNaseOUT (Invitrogen) at 65° C. for 5 minutes. The reverse transcription reaction was subsequently performed at 55° C. for 60 minutes using Superscript III RT (Invitrogen) and 2 µM dT20 primer (Eurogentec). Quantitative PCR was performed on a CFX96 thermal cycler (Bio-Rad). Thermal cycling was performed as follows: denaturation at 95° C. for 15 minutes, 40 cycles at 95° C. for 15 seconds, annealing for 30 seconds, elongation at 72° C. for 30 seconds and a final elongation for 10 minutes at 72° C. For each primer the specificity of amplification was verified by melting curve analysis and visualization of PCR products on an agarose gel with SYBR Safe (Invitrogen). Relative PCR quantification was performed using the comparative threshold cycle method using the arithmetic mean of PPIA and GAPDH as stable housekeeping genes. Samples with Ct values greater than three standard deviations from the mean were excluded from further analysis.

1.1. Brainbank Database Analysis of Gene Expression

CNS gene expression data were extracted from Allen Institute, BrainSpan: Atlas of the Developing Human Brain (www brainspan.org/static/download.html, file: RNA-Seg Gencode v10 summarized to genes). The dataset contains RNA-Seq RPKM (reads per kilobase per million) values averaged to genes. For detailed descriptions of sample preparation, tissue selection criteria and data normalization, see the technical white paper, Developmental Transcriptome (help.brain-map.org/display/devhumanbrain/Documentation). Depending on the brain region, gene expression data were extracted form 16-22 donors aged from 4 months to 40 years old. Note that prenatal samples of the database were excluded (pcw 8-37). Brain samples from male and female donors were equally represented.

1.12. Detection and Localization of Receptors by Flow Cytometry

Intracellular and surface ACKR3 levels were analysed by flow cytometry using ACKR3-specific mAb (12.5 μg/ml, clone 11G8 (R&D Systems) or a matched isotype control (12.5 μl/ml, clone MG1-45, BioLegend) and phycoerythrin-conjugated F(ab')2 fragment anti-mouse IgG (Jackson ImmunoResearch). Dead cells were excluded using the Zombie NIR fixable viability dye (BioLegend). For intracellular staining, cells were treated with the BD Cytofix/Cytoperm Fixation/Permeabilization solution kit (BD Biosciences) according to manufacturer recommendations. Fluorescence intensity was quantified on a Novocyte Quanteon flow cytometer (ACEA Biosciences).

1.13 Opioid Peptide-Induced Arrestin-Dependent ACKR3 Delivery to Endosomes

Opioid peptide-induced receptor-arrestin complex delivery to endosomes was monitored by β-galactosidase complementation using a PathHunter eXpress ACKR3 activated GPCR internalization assay (DiscoverX). In brief, U20S cells stably expressing ACKR3, β-arrestin-2 fused to the enzyme acceptor of β-galactosidase and an endosome marker fused to the β-galactosidase ProLink donor peptide were seeded 24 hours before the experiment in a 96-well plate at a density of $1\times10^4$ cells/well. Opioid peptides (3 μM and 300 nM) were then added and after 4-hour incubation at 37° C., luminescent signal was generated through addition of 55 si f-galactosidase substrate (PathHunter Detection reagent). After 1-hour incubation at room temperature, chemiluminescent signal was measured on a Mithras LB940 plate reader (Berthold Technologies).

1.14 Monitoring of Opioid Peptide-Induced Changes in Receptor Cell Surface Levels Determination of receptor surface expression level by NanoLuc complementation assay was performed using the Nano-Glo HiBiT extracellular detection system (Promega) according to manufacturer's protocol. In brief, $1.2\times10^6$ U87 cells were seeded on a 10-cm dish and 48 hours later transfected with 100 ng plasmid encoding ACKR3 or the respective opioid receptors N-terminally tagged with HiBiT, a small part of the Nanoluciferase with high affinity towards LgBiT. 48 hours later, $5\times10^4$ cells/well were seeded in 96-well plates and stimulated for the indicated time with CXCL12 (300 nM) or opioid peptides (1 μM) at 37° C. Cells were then incubated with HiBiT extracellular reagent, consisting of Nanoluciferase extracellular substrate and LgBiT protein in HiBiT buffer. Light emission from complementation of LgBiT protein with remaining surface receptor-fused HiBiT was determined on a Mithras LB940 plate reader (Berthold Technologies). Signal was normalised to the measurement recorded at t=1 min. Noteworthy the impact of nociceptin and derivatives could not be determined in this assay due to significant LgBiT protein cross-complementation by nociceptin. Where indicated, cells were treated with bafilomycin A1 (1.5 μM in 0.15% DMSO) (Santa Cruz Biotechnology) or 0.15% DMSO for 45 minutes prior ligand stimulation and during ligand stimulation (180 minutes).

For determination of receptor surface expression levels by flow cytometry, U87-ACKR3 or U87-KOR cells were stimulated with opioid peptides (1 μM) or CXCL12 (300 nM) for 60 minutes at 37° C. The remaining surface-bound ligands were then removed by a brief wash with 150 mM NaCl, 50 mM glycine, pH 3 and twice with FACS buffer. Where indicated, cells were incubated for additional 120 minutes to allow surface receptor recovery. Cell surface levels of ACKR3 or KOR were then measured by flow cytometry using a saturating concentration (12.5 μg/ml) of receptor-specific mAb (clones 11G8 for ACKR3 and 387301 for KOR, R&D Systems) and a secondary phycoerythrin-conjugated F(ab')2 fragment anti-mouse IgG (Jackson ImmunoResearch). Dead cells were excluded using the Zombie NIR fixable viability dye (BioLegend). Mean fluorescence intensity was quantified on a Novocyte Quanteon flow cytometer (ACEA Biosciences).

1.15. Data Analysis

Concentration-response curves were fitted to the four-parameter Hill equation using an iterative, least-squares method (GraphPad Prism version 8.0.1). All curves were fitted to data points generated from the mean of at least three independent experiments.

Example 2. ACKR3 is Activated by a Broad Range of Opioid Peptides from Different Families In a recent study, present inventors suggested that the proenkephalin-derived peptide BAM22 shares structural and functional features important for/involved in ACKR3 binding and activation with the N terminus of chemokine ligands. Given that all endogenous opioid peptides show remarkable sequence homologies including the F/YGGFL/M (SEQ ID NO: 12) motif at their N termini, as well as several positively charged residues throughout the sequence, present inventors wondered whether BAM22 and the related peptides are the only opioid peptides able to activate ACKR3 (FIG. 1H; Table 1a). Therefore, present inventors screened a library of 58 opioid peptides for their ability to induce β-arrestin-2 recruitment to ACKR3, and, additionally to CXCR4 and CXCR3, two classical chemokine receptors sharing CXCL12 and CXCL11, respectively, as ligands with ACKR3, which served as negative controls. Besides BAM22, BAM18 and Peptide E previously reported as ACKR3 ligands, present inventors' screening revealed that numerous other opioid peptides are capable of inducing β-arrestin-2 recruitment to ACKR3. These included adrenorphin, another proenkephalin-derived peptide, but also peptides from the nociceptin and dynorphin families (FIG. 1A). Endorphins and endomorphins, however, did not activate ACKR3. None of these peptides acted as ACKR3 antagonist (data not shown) or induced β-arrestin-2 recruitment to CXCR4 or CXCR3 (FIG. 1A).

Present inventors next analysed and compared the potency and efficacy of the different hits towards ACKR3 and the classical opioid receptors in β-arrestin-1 and β-arrestin-2 recruitment (FIGS. 1B-F and H, Table 1b, data for β-arrestin-2 are not shown). ACKR3 was activated by several endogenous opioid peptides such as dynorphin A, dynorphin A 1-13, big dynorphin, BAM22 or adrenorphin at low concentrations comparable to their activity on the classical opioid receptors. Higher concentrations of dynorphin B, nociceptin or nociception 1-13 amide were necessary for ACKR3 activation. Surprisingly, ACKR3 was also activated by the NOP antagonist Phe1ψ(CH₂—NH)-Gly2-Nociceptin-1-13 amide (F-G nociceptin 1-13) (SEQ ID NO: 13; NH₂-substituted at C-terminus) as well as by endogenous truncated dynorphin variants, dynorphin 2-13 (SEQ ID NO: 20; NH₂-substituted at C-terminus) and dynorphin 2-17 (SEQ ID NO: 19) (FIG. 1H, Table 1b), which do not activate the classical opioid receptors but were shown to have a physiological effect. ACKR3 seems to show some degree of selectivity as several peptides, like endorphins, short endomorphins and Leu- or Met-enkephalin did not trigger β-arrestin recruitment. These data were further confirmed in HEK293T and CHO-K1 cellular backgrounds (data not shown) and in binding competition studies, showing that all of the identified ligands were able to compete with and displace Alexa Fluor 647-labelled CXCL12 from ACKR3 (FIG. 1G). To conclude, these data reveal that ACKR3, unlike CXCR3 or CXCR4, is selectively activated by a variety of endogenous opioid peptides from different families in a concentration range similar to that observed for activation and signalling via opioid receptors.

ACKR3 is the Only Chemokine Receptor Activated by Opioid Peptides

Figure 2:
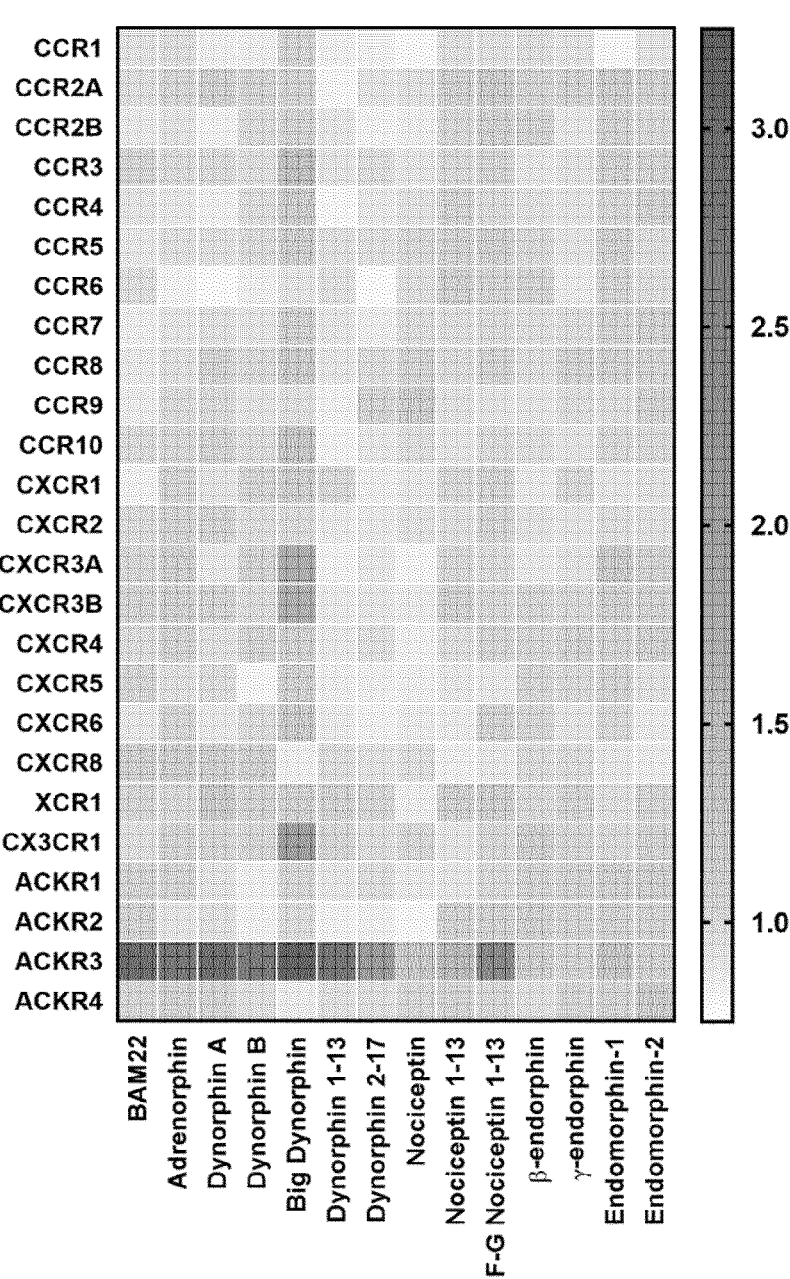
FIG. 2. Specific activation of ACKR3 by opioid peptides. Agonist activity of opioid peptides (3 μM) representative of the four opioid families towards the 21 classical and 4 atypical chemokine receptors evaluated in β-arrestin-1 recruitment assay in U87 cells. For each receptor, 100 nM of one known agonist chemokine listed in the IUPHAR repository of chemokine receptor ligands was added as positive control. Results are expressed as fold change over vehicle and presented as mean $(n \geqslant 3)$.

Just like classical opioid receptors, many chemokine receptors have multiple ligands, which they often share with other receptors. Thus, present inventors wondered whether ACKR3 is the only member of the chemokine receptor family activated by opioid peptides. To this end, present inventors tested all chemokine receptors for arrestin recruitment in response to the different ACKR3-binding opioid peptide ligands at a saturating concentration using the same Nanoluciferase complementation assay. None of the peptides induced similar β-arrestin-1 or β-arrestin-2 recruitment to any of the 24 other chemokine receptors (FIG. 2, data for β-arrestin-2 are not shown). A faint induction of β-arrestin recruitment was detectable towards several receptors such as CX3CR1, CXCR3 and CCR3 treated with big dynorphin. However contrary to ACKR3 or opioid receptors, their responses to big dynorphin were severely reduced compared to those achieved with their cognate chemokines (data not shown). These data provide strong support for the notion that the capacity to recruit arrestins in response to endogenous opioid peptides is unique and distinguishing for ACKR3 among all chemokine receptor family members.

Figure 3:
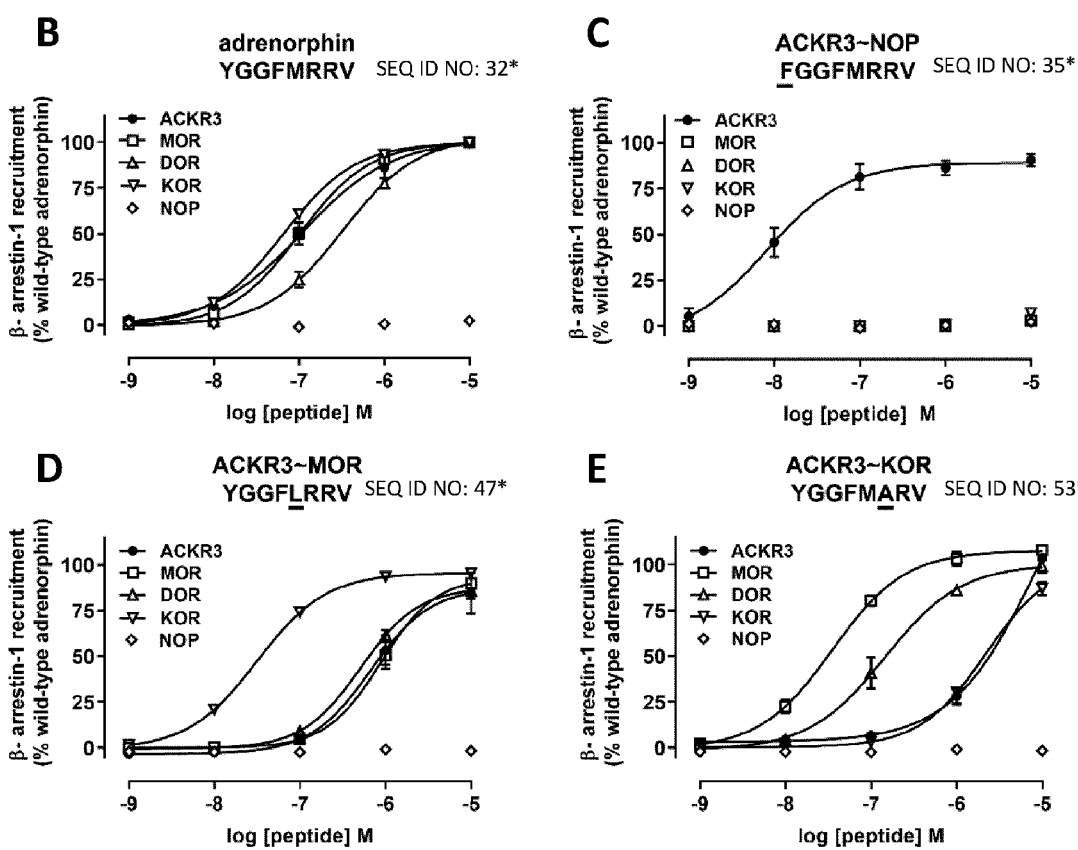
FIG. 3. Structure-activity relationship analysis of adrenorphin variants on ACKR3 and classical opioid receptors. (A) Comparison of the impact of substitutions, truncations, extensions, D-amino acid replacement or dimerization on the agonist activity of adrenorphin towards ACKR3, MOR, DOR, KOR and NOP. The agonist activity or each variant was evaluated in β-arrestin-1 recruitment assay in U87 cells and expressed as fold change over the activity of wild-type adrenorphin. (B-E) Comparison of potency and efficacy of adrenorphin (B) and its variants bearing mutations Y1F (C), M5L (D) and R6A (E) to induce β-arrestin-1 recruitment to ACKR3 and the opioid receptors KOR, MOR, DOR and NOP in U87 cells. "~" indicates a similar impact of the modification on the potency of the peptide towards ACKR3 and the indicated opioid receptor. Results represent the mean±S.E.M. $(n \geqslant 3)$ (F) Comparison of the potencies of peptide variants combining mutations Y1F with other modifications (mutations and/or extension) to induce β-arrestin-1 recruitment to ACKR3. Modified amino acids with respect to the mother peptide (Y1F adrenorphin FGGFMRRV) are underlined and in bold.

Similarities and Differences of ACKR3 and Classical Opioid Receptor Binding Pocket: Adrenorphin Structure-Activity-Relationship Study To gain further insights into the binding and activation modes of ACKR3 compared to classical opioid receptors, present inventors performed a structure-activity relationship study based on the octapeptide adrenorphin (YGGFMRRV (SEQ ID NO: 32; $NH_2$-substituted at C-terminus), formerly metorphamide). Adrenorphin triggered arrestin recruitment to ACKR3, MOR, DOR and KOR with roughly the same potency (FIG. 3B), providing a suitable base for investigating the activation mode of the four receptors. Present inventors performed an alanine scan of adrenorphin and introduced substitutions by closely related amino acids or other modifications such as N- and C-terminal extension, D-amino acid replacement or dimerization. Present inventors evaluated the ability of these modified peptides to activate ACKR3 and the opioid receptors in β-arrestin-1 recruitment assay (FIG. 3A). Interestingly, the "message" and "address" sequences were somewhat different for ACKR3 compared to classical opioid receptors, despite a similar trend in potency changes. ACKR3 appears to be more tolerant to modifications of the N-terminal tyrosine residue, critical for the activation of classical opioid receptors. Indeed, variants displaying a leucine or a phenylalanine retained the parental activity, with Y1F mutation, mimicking the nociceptin peptide N terminus resulting in a tenfold improvement in potency (FIGS. 3A and C). However, similarly to classical receptors, the phenylalanine at position 4 of the YGGF-L/M (SEQ ID NO: 15) core was found to be crucial for ACKR3 binding, as any mutation, with the exception of F4W, was detrimental for receptor activation.

Methionine-to-leucine substitution at position 5, mimicking peptides of the dynorphin family, improved binding to KOR but significantly reduced the binding to MOR and ACKR3 (FIG. 3D), whereas mutations at positions 6 in the di-arginine motif abolished the activity towards KOR and ACKR3, but largely improved the activity towards MOR (FIG. 3E).

Based on the above SAR analysis present inventors concluded that the interaction mode of ACKR3 with opioid peptides is in some aspects distinct from that of the classical opioid receptors, with ACKR3 sharing important interaction determinants with all of the other four receptors. This feature likely explains its ability to bind and respond to peptides from different families.

ACKR3 is Unresponsive to Alkaloid Opioids and Synthetic Opioid Drugs

Figure 4:
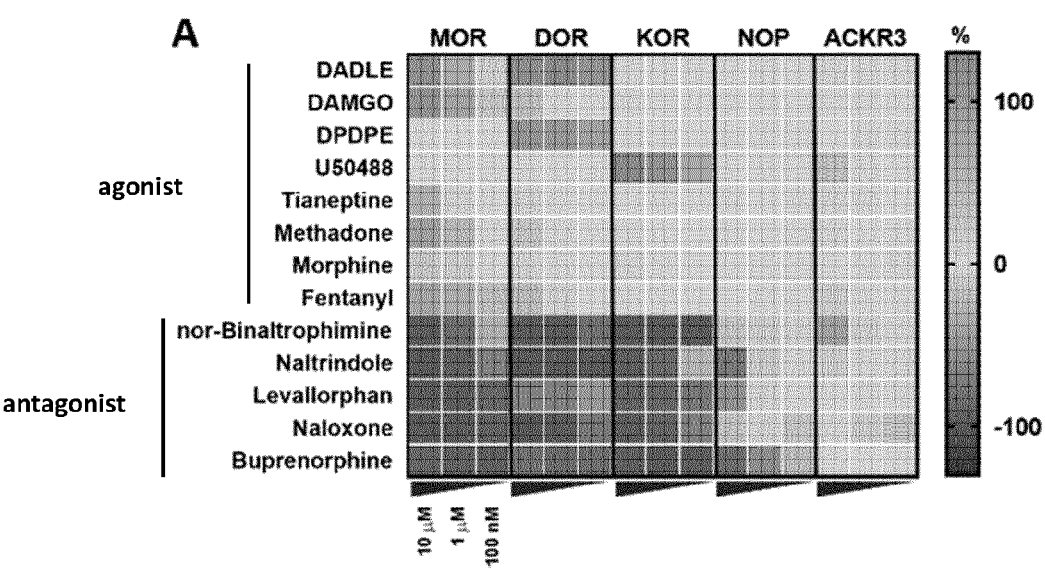
FIG. 4. Activity of classical opioid modulators towards ACKR3 and development of LIH383 as subnanomolar ACKR3-selective agonist. (A) Agonist and antagonist activity towards ACKR3 of opioid modulators (10 μM, 1 μM and 100 nM) commonly used for research purposes or in clinic and comparison with the opioid receptors MOR, DOR, KOR and NOP monitored in a β-arrestin-1 recruitment assay. Antagonist activity was measured following addition of BAM22 (50 nM), met-enkephalin (70 nM), dynorphin A (50 nM), nociceptin (70 nM) and CXCL12 (4 nM) on MOR, DOR, KOR, NOP and ACKR3, respectively. (B and E) Agonist activity of LIH383 towards human (B) and mouse (E) ACKR3 and comparison with other endogenous ACKR3 chemokine ligands, and a control peptide (MRRKFGGF), consisting of the 8 amino acids building LIH383 in a different arrangement. (C and D) LIH383 selectivity evaluated by comparison of β-arrestin-1 recruitment to ACKR3 and the opioid receptors MOR, DOR, KOR and NOP (C) or all the other known chemokine receptors (3 μM) (D). (F) Selective binding of fluorescently labelled LIH383 (LIH383-Cy5) to ACKR3-expressing cells. All assays were performed in U87 cells. Results represent the mean±S.E.M. $(n \geqslant 3)$. (G) Binding competition of increasing concentrations of ACKR3-activating chemokines, adrenorphin or LIH383 with Alexa Fluor 647-labelled CXCL12 (5 nM) on U87-ACKR3 cells determined by flow cytometry. (H) Activation of Serum Responsive Element (SRE) linked to ERK1/2 signalling cascade in U87 cells (–) or U87 expressing ACKR3, CXCR4 or classical opioid receptors (MOR, DOR, KOR or NOP) in response to LIH383 or positive controls (+ctrl, 30 nM PMA, 10% FBS). Bars for untreated cells (Medium) are used as baseline reference. (I) Dose dependent antagonist activity of LIH383 (3000 nM-12.3 nM) towards classical opioid receptors DOR, MOR, KOR and NOP monitored by β-arrestin-1 recruitment. Naloxone (1000 nM-4.1 nM) for DOR, MOR and KOR or buprenorphine (27000 nM-111 nM) for NOP were used as positive control antagonists. Antagonist activity was measured following addition of BAM22 (50 nM), met-enkephalin (70 nM), dynorphin A (50 nM), nociceptin (70 nM) on MOR, DOR, KOR and NOP, respectively. Results are presented as mean±S.E.M $(n \geqslant 3)$.
Figure 4:
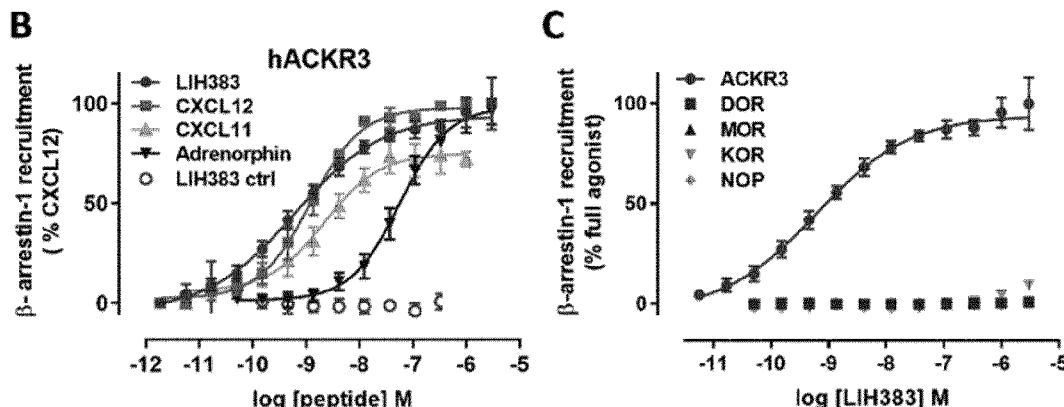
Figure 4:
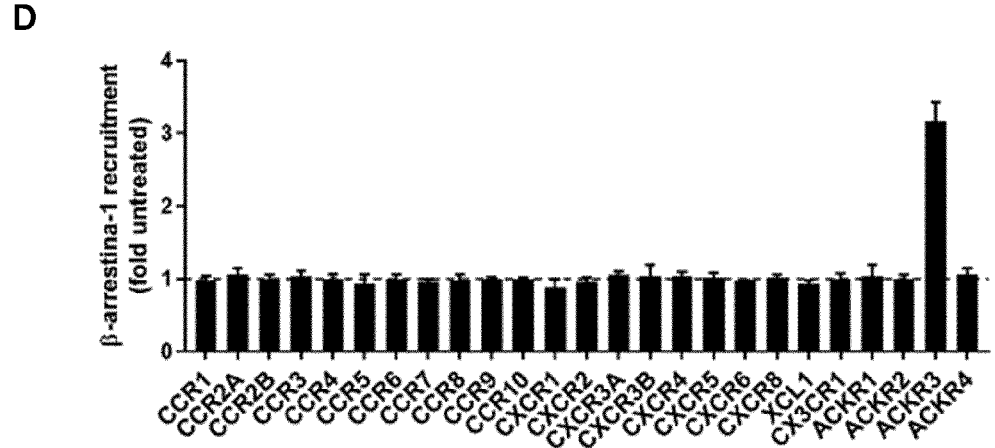
Figure 4:
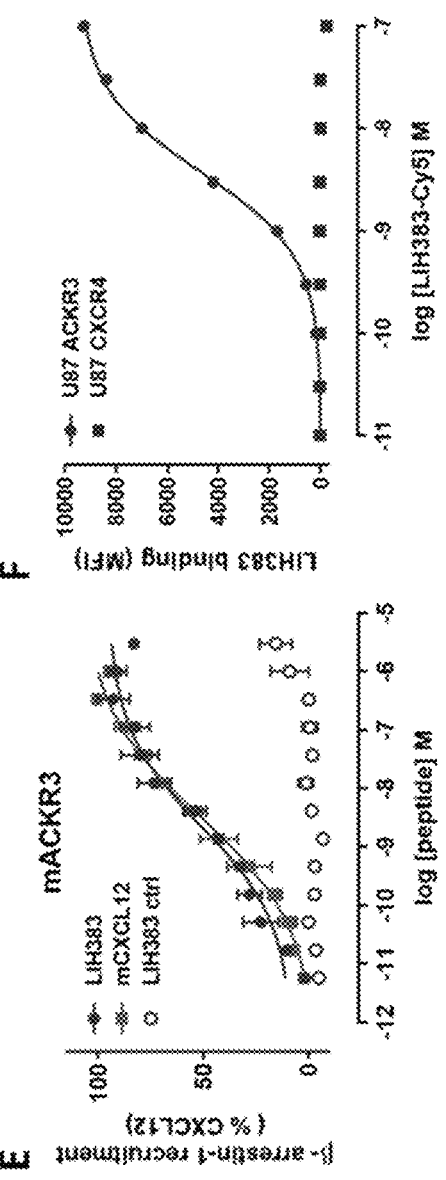
Figure 4:
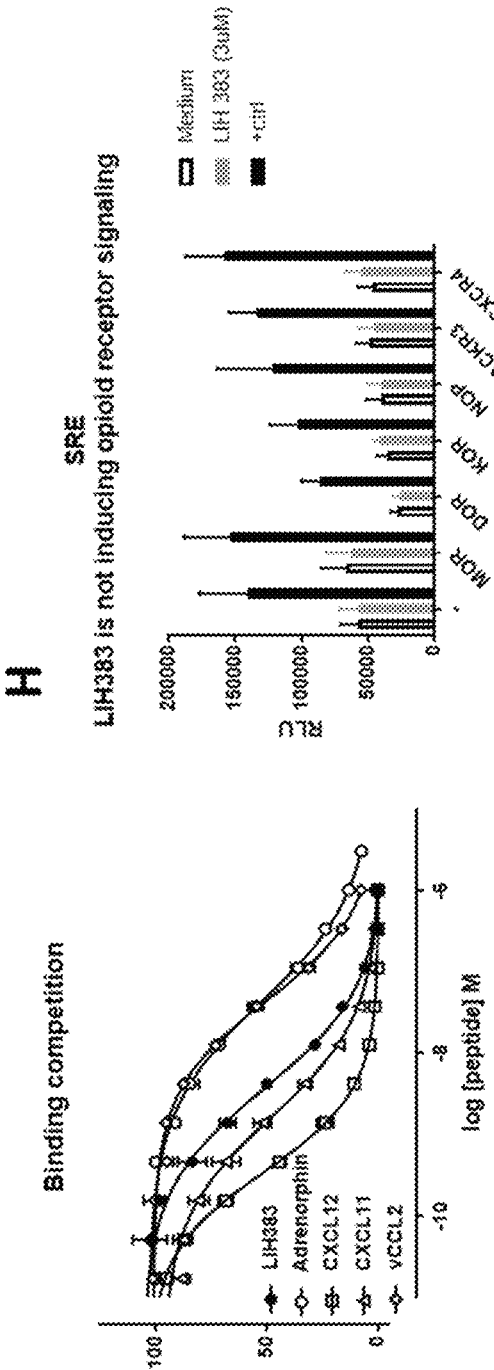
Figure 4:
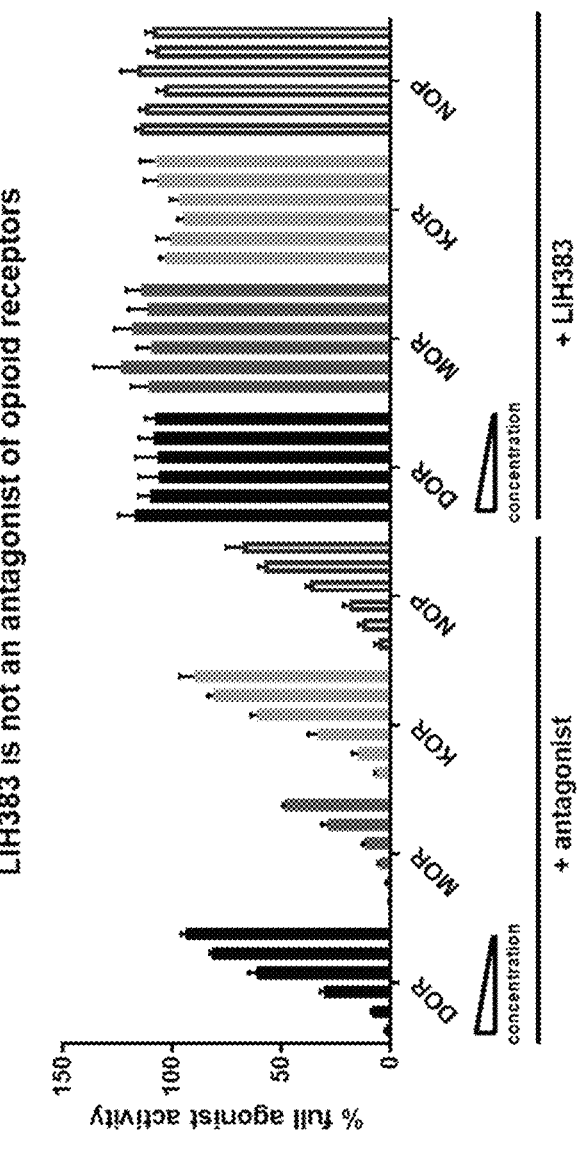

Based on its ability to respond to different families of endogenous opioid peptides and the binding mode similarities with classical opioid receptors, present inventors wondered whether ACKR3 could also respond to non-endogenous opioid ligands commonly used to activate or inhibit the classical opioid receptors. Besides prototypical opioid tool compounds like D-Ala$^2$, D-Leu$^5$-Enkephalin (DADLE) (SEQ ID NO: 16) or D-Ala$^2$, N-MePhe$^4$, Gly-ol]-enkephalin (DAMGO), (SEQ ID NO: 17) present inventors tested approved pain medications such as morphine, fentanyl or buprenorphine in β-arrestin recruitment assays. All molecules showed their expected agonist or antagonist activities on their respective opioid receptors (FIG. 4A). For morphine, only a weak β-arrestin recruitment to MOR was observed in line with previous reports. At high concentrations, many of these molecules, although designed to target specifically one receptor, showed some activity towards other opioid receptors, similarly to what is observed with endogenous ligands. However, ACKR3 was not responsive to any of the molecules tested, even at high concentrations. Weak activation of ACKR3 was observed with the KOR agonist U50488 and antagonist nor-binaltrophimine, but with a much weaker potency compared to KOR.

These results show that although ACKR3 shares several endogenous opioid peptides with classical opioid receptors, it is not modulated by opiate analgesics or synthetic opioid drugs targeting classical opioid receptors.

Example 3 Development of LIH383, an Adrenorphin Derived Octapeptide with High Specificity and Subnanomolar Agonist Activity Towards ACKR3

To develop a highly potent and selective ACKR3 modulator present inventors designed a second generation of peptides taking advantage of the adrenorphin SAR data. Present inventors used the adrenorphin Y1F variant (SEQ ID NO: 35; $NH_2$-substituted at C-terminus) as scaffold as it showed a 10-fold increase in potency towards ACKR3 and over 100-fold reduction of potency towards the classical opioid receptors MOR, DOR and KOR as compared to WT adrenorphin (FIGS. 3A and C). Other mutations increasing the potency towards ACKR3 including F4W, V8F, V8K or 9R were further combined and the resulting peptides were tested in a β-arrestin recruitment assay (FIG. 3F). Of all the combinations tested, the octapeptide FGGFMRRK (SEQ ID NO: 3; $NH_2$-substituted at C-terminus) (designated LIH383) was the most potent ACKR3 agonist, with an $EC_{50}$ of 0.61 nM. Remarkably, LIH383 was more potent in inducing β-arrestin recruitment to ACKR3 than the full-length chemokine ligands CXCL12 or CXCL11 ($EC_{50}$=1.2 nM and 2.2 nM, respectively) (FIG. 4B). Importantly, no activation or inhibition of any other opioid receptor, nor of any other chemokine receptor could be detected upon LIH383 treatment, even at concentrations as high as 3 μM (FIGS. 4C, D, H and I). LIH383 had also equivalent activity on human and mouse ACKR3 (mACKR3) (FIGS. 4B and E). LIH383 competed directly with CXCL12-AF647 for ACKR3 binding at low nanomolar concentrations (FIG. 4G). Moreover, Cy-5-labelled LIH383 bound to ACKR3-expressing U87 cells, but not to native or CXCR4-expressing U87 cells (FIG. 4F), making this peptide a potentially valuable and versatile tool for specific ACKR3 modulation or detection of ACKR3-expressing cells.

Example 4. ACKR3 does not Signal in Response to Endogenous Opioid Peptides

Figure 5:
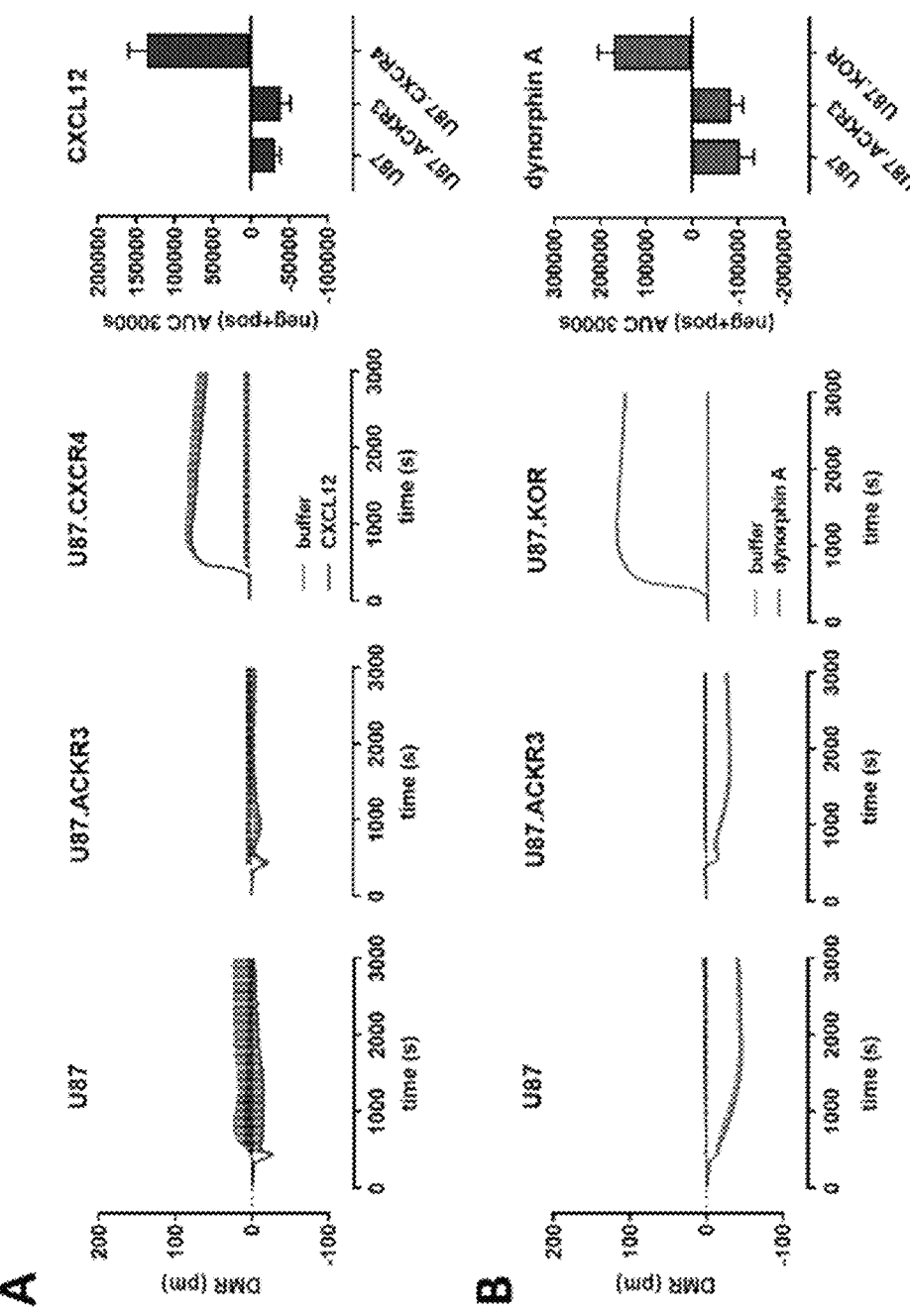
FIG. 5. Absence of ACKR3 signalling in response to opioid and chemokine ligands. (A-D) DMR profiles of U87 cells or U87 cells expressing ACKR3, CXCR4 or classical opioid receptors (KOR and NOP) stimulated by the chemokine CXCL12 (200 nM) (A) or opioid peptides (500 nM) dynorphin A (B), adrenorphin (C) and nocicepetin 1-13 (D). Left panels: representative DMR profiles determined over 3000 seconds. Right panel: area under the curve (AUC) ±S.E.M. of at least three independent experiments. (E) Comparison of mini Gi recruitment to ACKR3, CXCR4 and classical opioid receptors (MOR, DOR, KOR or NOP) in response to CXCL12 and opioid peptides monitored in U87 cells. (F) Kinetic analysis of ERK1/2 phosphorylation in U87 cells stably expressing ACKR3 or CXCR4 stimulated by CXCL12 and opioid peptides. EGF was used as positive control. (G) Comparison of activation of SRE (ERK1/2) and NFAT-RE ($Ca^{2+}$) signalling cascades in U87 cells (–) or U87 expressing ACKR3, CXCR4 or classical opioid receptors (MOR, DOR, KOR or NOP) in response to chemokines CXCL12 and CXCL11 (200 nM) or opioid peptides (500 nM) or positive controls (30 nM PMA, 10% FBS for SRE and 30 nM PMA, 1 μM ionomycin, 10% FBS for NFAT-RE). Results represent the mean±S.E.M. $(n \geqslant 3)$.
Figure 5:
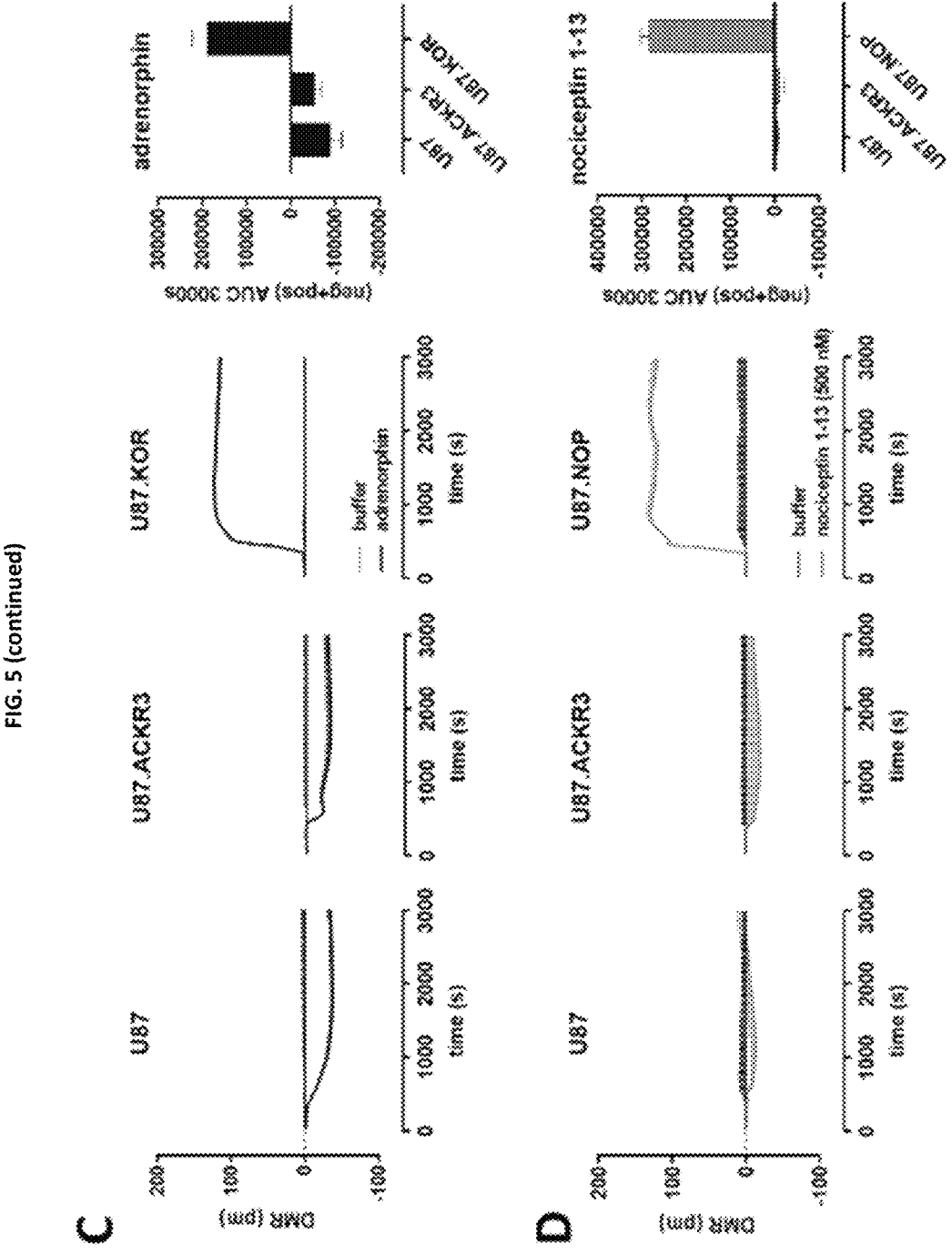
Figure 5:
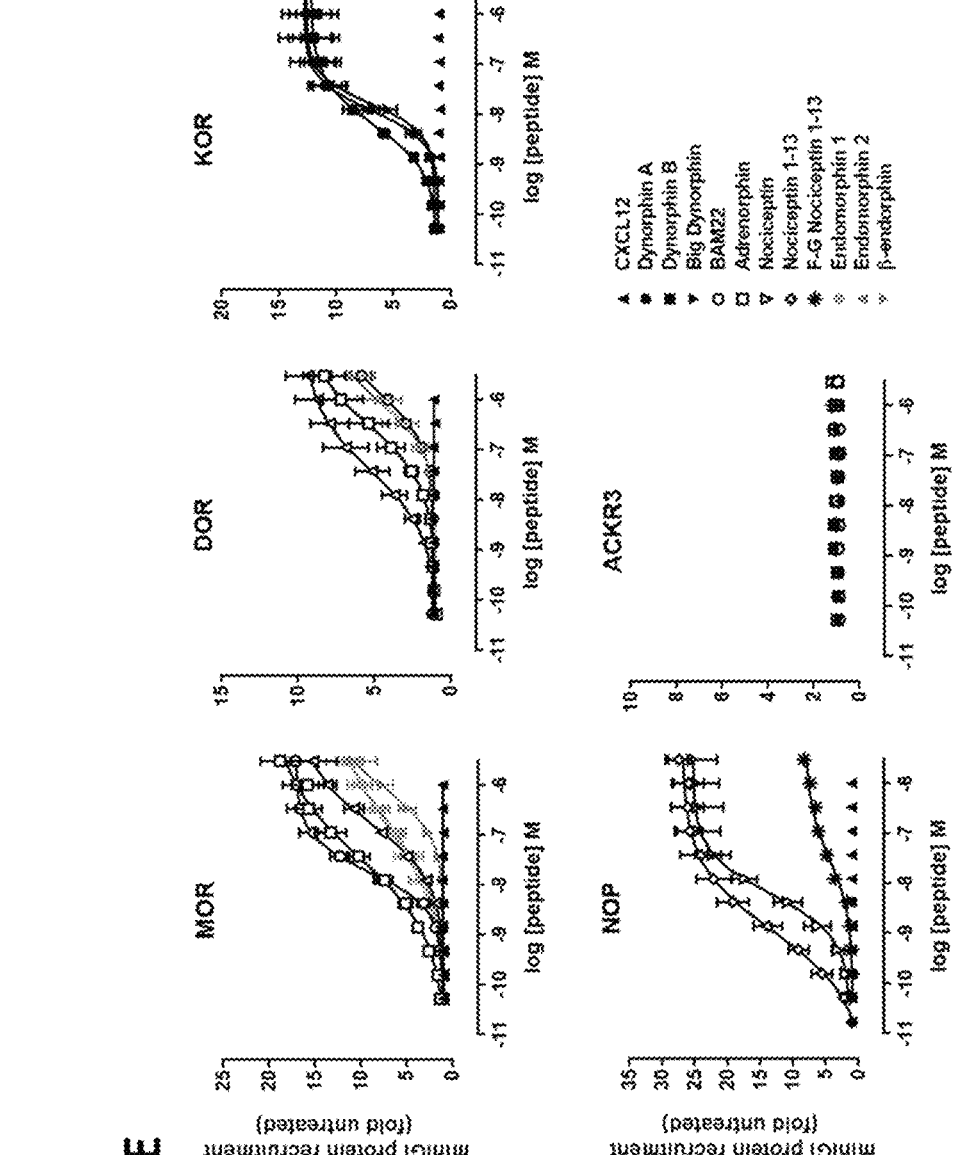
Figure 5:
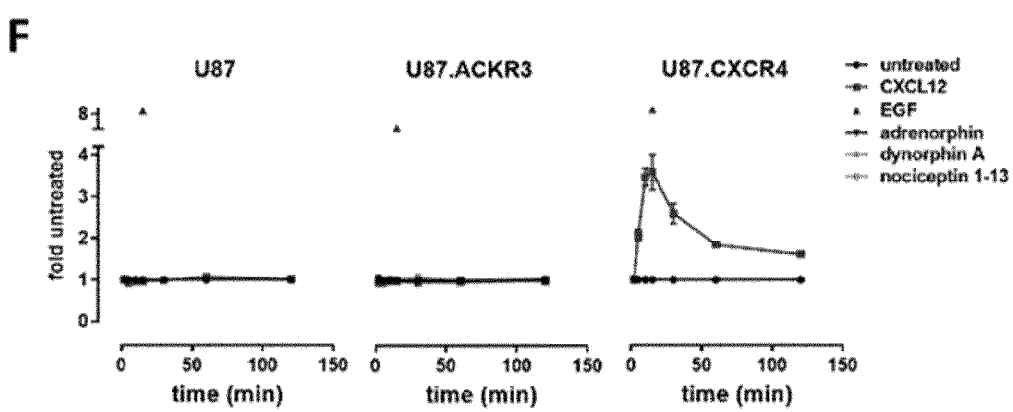
Figure 5:
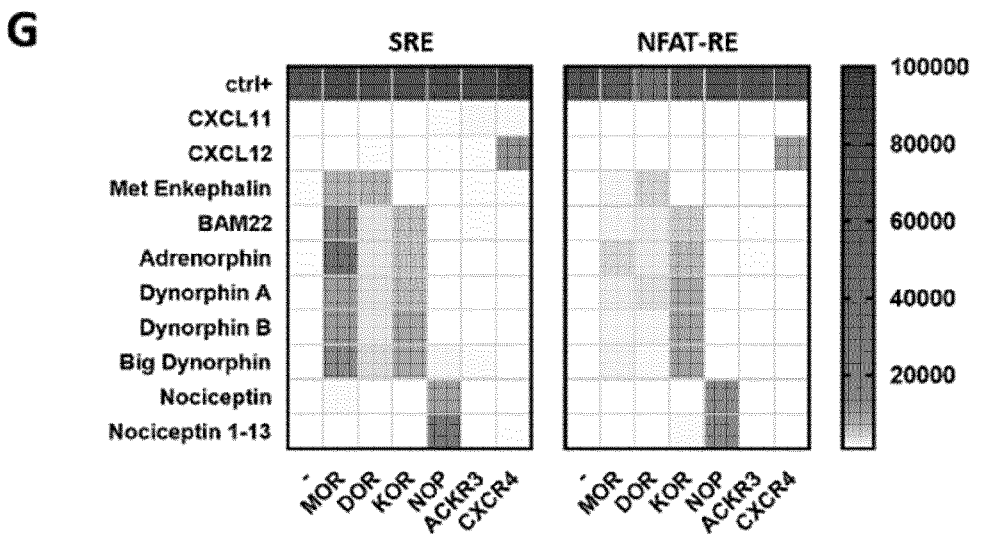

To decipher the function and impact of ACKR3 on the opioid system, present inventors tested the ability of opioid peptides to trigger downstream signalling through ACKR3 in U87 cells. Present inventors first applied a whole-cell optical biosensing approach based on dynamic mass redistribution (DMR), which enables to detect multiple downstream signalling events including all four major G protein pathways. In agreement with other studies, present inventors did not detect any ACKR3-dependent signalling upon chemokine stimulation (FIG. 5A). Likewise, no difference in DMR signal was observed between ACKR3-transfected and non-transfected cells in response to opioid peptides (FIG. 5B-D). In contrast, U87 cells expressing the G protein signalling-competent CXCR4, KOR or NOP, did show a strong DMR in response to CXCL12, dynorphin A/adrenorphin or nociception 1-13, respectively, in accordance with a robust activation of downstream signalling pathways by these receptors (FIG. 5A-D). In line with these observations, present inventors did not detect any interaction of ACKR3 with mini G (mG) proteins (mGi, mGs, mGq or mG12/13) upon chemokine or opioid peptide treatment, in contrast to CXCR4 or classical opioid receptors, which all efficiently recruited mGi (FIG. 5E, data not shown for mGs, mGq and mG12/13). Moreover, ERK phosphorylation levels monitored by Homogeneous Time Resolved Fluorescence (HTRF) remained unchanged upon ligand stimulation of cells stably expressing ACKR3, whereas a strong increase in ERK phosphorylation was observed between 2 and 120 minutes after CXCL12 stimulation of cells stably expressing CXCR4 (FIG. 5F). These results were further corroborated by the absence of activation of the MAPK/ERK-dependent Serum Response Element (SRE) upon opioid peptide or chemokine stimulation in ACKR3-positive U87 cells (FIG. 5G, left panel) or HEK293T and CHO-K1 cells (data not shown), in contrast to the robust signal increase in CXCR4- or classical opioid receptor-expressing cells upon stimulation with the respective ligands. Similar absence of signalling through ACKR3 in response to opioid or chemokine ligands was shown for calcium-dependent Nuclear Factor of Activated T-cell Response Element (NFAT-RE) activation (FIG. 5G, right panel).

These data demonstrate that opioid peptides induce β-arrestin recruitment to ACKR3 but are inactive in canonical G protein-driven readouts, suggesting that ACKR3 may act as a scavenger for opioid peptides.

Figure 6:
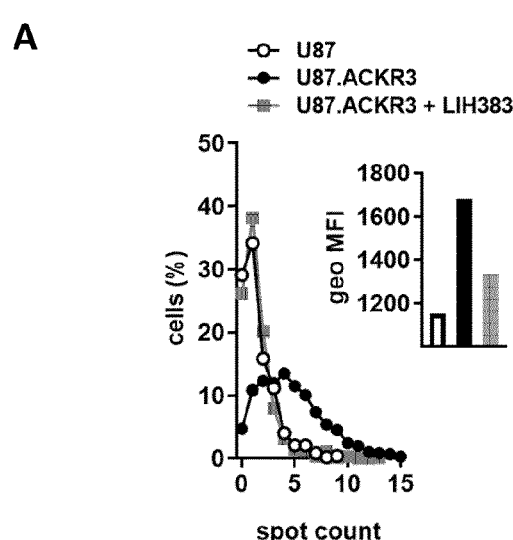
FIG. 6. Efficient uptake of various opioid peptides and atypical localization and trafficking properties of ACKR3 in comparison to classical opioid receptors (A) Fluorescently labelled dynorphin A (1-13) uptake by ACKR3-expressing cells was visualised by imaging flow cytometry. U87, U87-ACKR3 or U87-ACKR3 cells pre-treated with LIH383 (3 μM) were stimulated for 40 minutes at 37° C. with 250 nM (FAM)-labelled dynorphin A (1-13). Dead cells were excluded using a viability dye. For each condition, the percentage of cells with a given number of distinguishable vesicle-like structures (spots), as well as the geometrical mean fluorescence intensity (MFI) for the green channel (FAM labelling) were determined. Data shown are representative of three independent experiments. (B) Uptake of fluorescently labelled opioid peptides (dynorphin A (1-13)-FAM (250 nM), big dynorphin-Cy5 (400 nM), BAM22-Cy5 (400 nM) or nociceptin-FAM (1 μM)) representative of different families (dynorphin, enkephalin or nociceptin) by U87 cells (NT) or U87 cells transfected with ACKR3 or the corresponding preferred classical opioid receptor (KOR, MOR or NOP) analysed by imaging flow cytometry as described in (A). (C) ACKR3-mediated depletion of extracellular dynorphin A monitored by its ability to activate KOR. U87 or U87-ACKR3 cells pre-treated for 15 minutes with LIH383 (400 nM) or the control peptide (LIH383 ctrl) (left panel) and CXCL12 (200 nM) or the negative control chemokine CXCL10 (right panel) were incubated with dynorphin A for 25 minutes. Cell supernatant was then added on U87 cells expressing SmBiT-tagged KOR and LgBiT-beta-arrestin-1 (left panel) or LgBiT-mini Gi (right panel). (insets): $EC_{50}$ values represented as bar graphs. (D)
Figure 6:
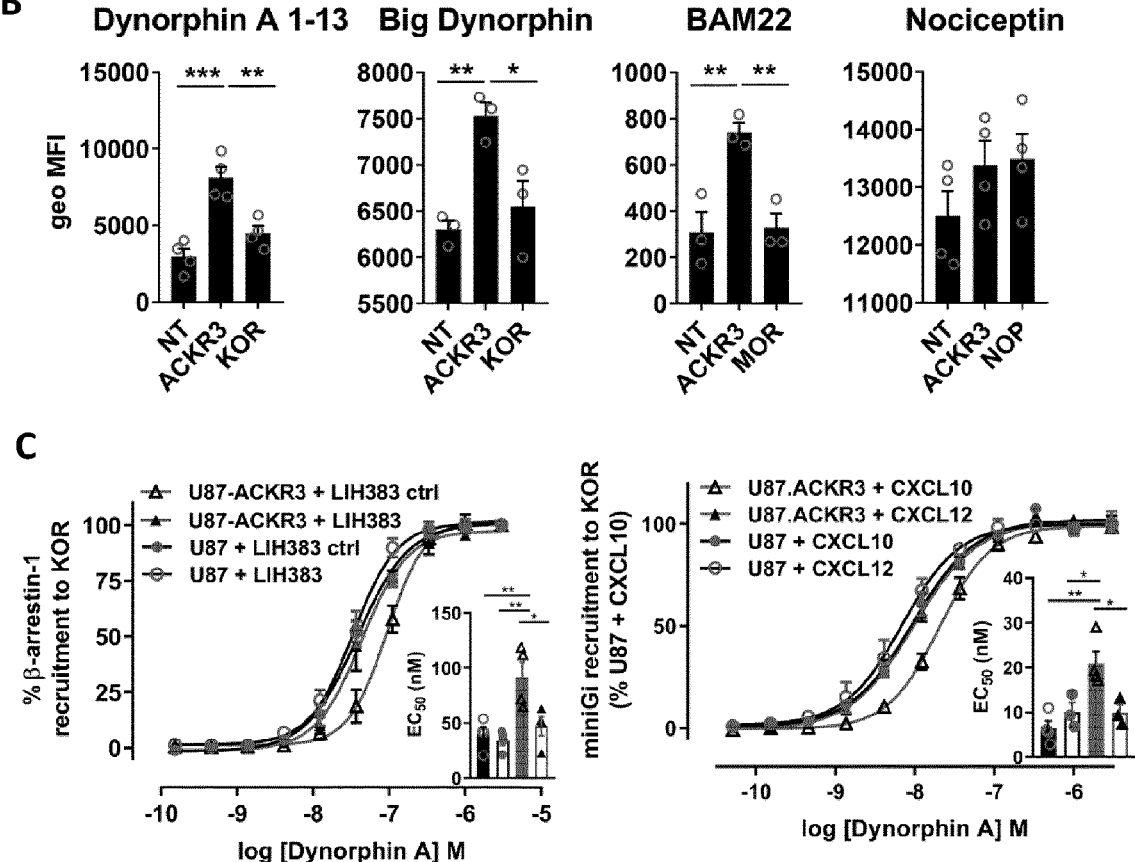
Figure 6:
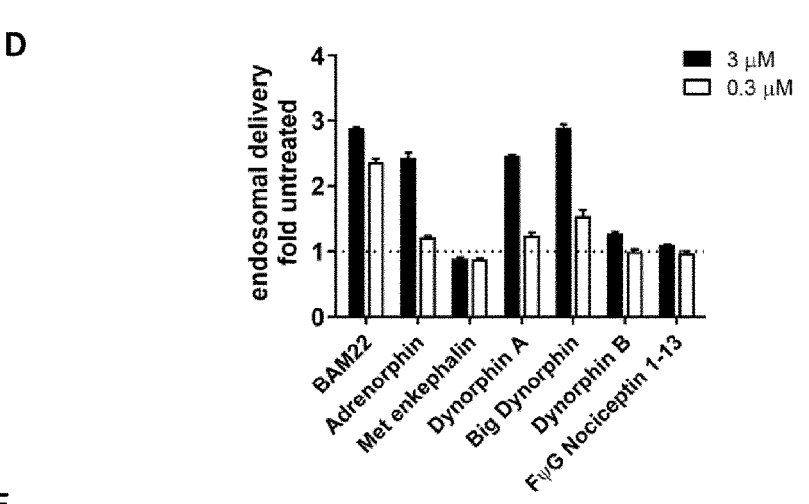
Figure 6:
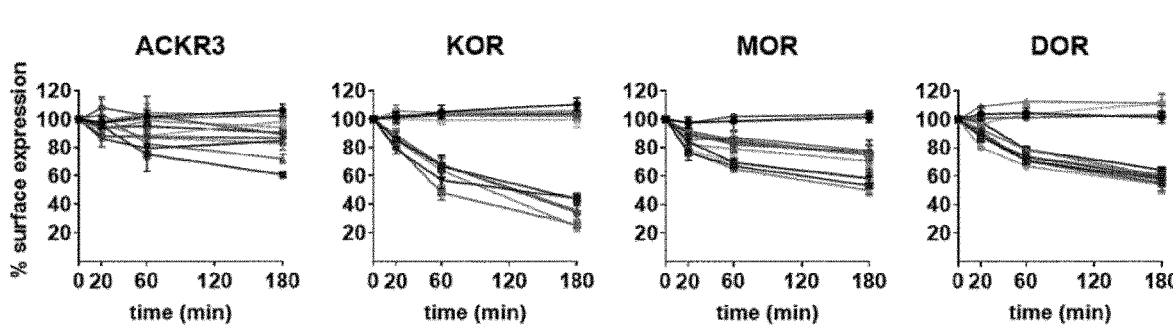
Figure 6:
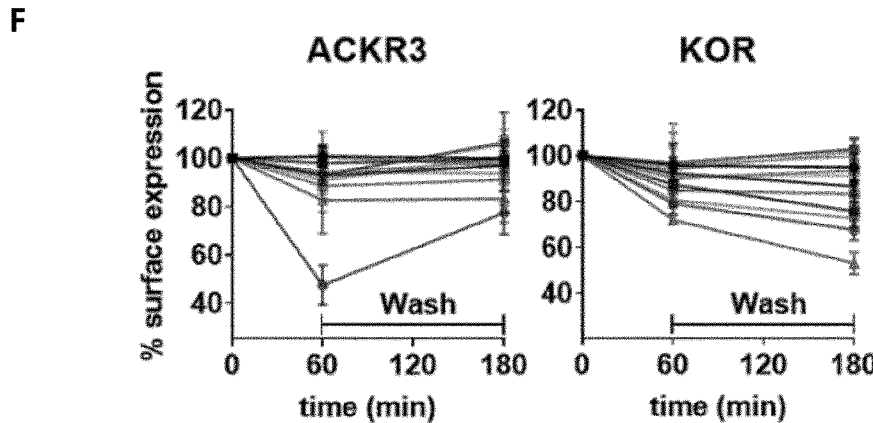
Figure 6:
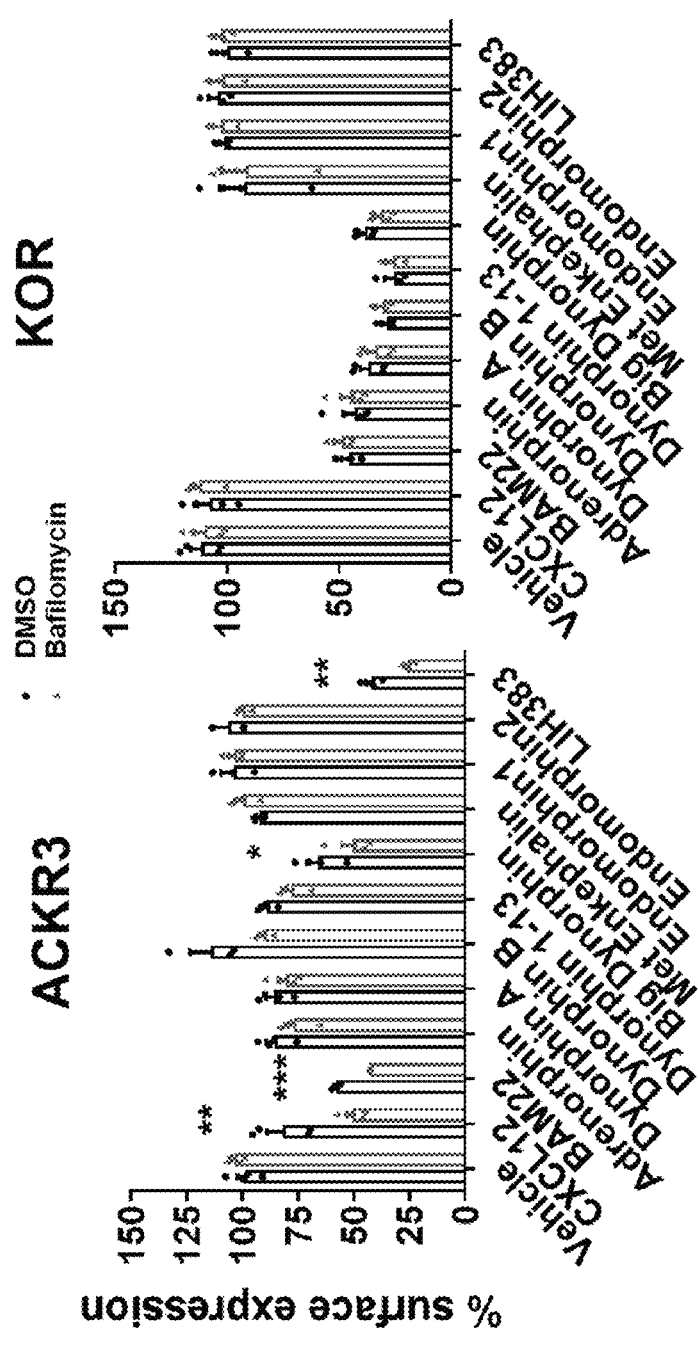

Example 5. ACKR3 Mediates Endogenous Opioid Peptide Uptake, which can be Modulated or Blocked by the Peptides of the Invention To investigate the ability of ACKR3 to scavenge opioid peptides, present inventors measured the uptake of fluorescently labelled opioid peptides of different families by cells expressing ACKR3 or the corresponding classical opioid receptors using imaging flow cytometry. For dynorphin-A (1-13), use was made of mono-5(6)-Carboxyfluorescein (FAM)-labelled dynorphin A (1-13), hereafter dynorphin A-FAM, and the uptake thereof by U87-ACKR3 cells was measured using imaging flow cytometry. Present inventors observed a clear intracellular accumulation of the fluorescently labelled peptide after 40-minute stimulation, with a notably higher number of distinguishable vesicle-like structures and mean fluorescent intensity compared to U87 cells or U87-ACKR3 cells pre-incubated with saturating concentrations of LIH383 (FIG. 6A) demonstrating that ACKR3 can mediate the uptake of opioid peptides. Moreover the uptake of dynorphin A (1-13) by ACKR3 was more efficient compared to that of KOR, the main classical opioid receptor for this peptide, despite the lower potency of dynorphin A (1-13) towards ACKR3 (FIG. 6B). Similar observations were made for labelled big dynorphin A, the precursor of dynorphin A and B, and for BAM22, a peptide from the enkephalin family. Indeed, despite its similar potency towards the two receptors, BAM22 was markedly more internalised by ACKR3-positive than by MOR-positive cells. The low-affinity ligand nociceptin was also internalised by ACKR3 to a degree equivalent to the corresponding classical opioid receptor NOP (FIG. 6B). Importantly, this ACKR3-driven intracellular accumulation of opioid peptides was also associated with a reduction of their availability in the extracellular space. For instance, present inventors found that the apparent potency of dynorphin A to activate KOR was impaired in the presence of ACKR3-expressing cells. This effect was reversed when ACKR3-expressing cells were pre-treated with a saturating concentration of LIH383 or CXCL12 but not with the irrelevant control peptide (LIH383 ctrl) or irrelevant chemokine CXCL10, illustrating the plausible scavenging function of ACKR3 (FIG. 6C).

Example 6. ACKR3 Shows Atypical Localization and Recycling Pattern Compared to Classical Opioid Receptors In line with this scavenging function, ACKR3 showed an atypical cellular localization, internalization and trafficking pattern compared to classical opioid receptors. In agreement with previous reports, present inventors observed that a much higher proportion of ACKR3 was present intracellularly compared to the cell surface. In contrast, classical opioid receptors MOR, DOR, KOR and NOP were mainly localised at the plasma membrane (data not shown). Moreover, despite an efficient uptake of various opioid peptides and their delivery to the early endosomes (FIG. 6D), the overall reduction of ACKR3 at the cell surface was much less pronounced than for classical opioid receptors, likely reflecting the rapid cycling of ACKR3 between the plasma membrane and intracellular compartments (FIG. 6E). Similar to what was reported for chemokines, present inventors found that agonist removal after stimulation led to progressive increase of ACKR3 at the plasma membrane, while for classical receptors like KOR such recovery was not observed (FIG. 6F). This was further corroborated by results obtained with bafilomycin A1, an inhibitor of vacuolar-type H+-ATPases. Previous studies showed that low endosomal pH is needed for chemokine dissociation from ACKR3 and efficient receptor recycling and resensitization. Present inventors observed that treatment with bafilomycin A1, an inhibitor of vacuolar-type H+-ATPases, resulted in decreased receptor recovery at the plasma membrane following stimulation with diverse opioid peptides, whereas it had no effect on surface levels of KOR (FIG. 6G). Altogether, these results demonstrate that ACKR3 can support a rapid and efficient uptake of opioid peptides of different families through continuous receptor cycling between the intracellular compartments and the plasma membrane, leading to a progressive depletion of extracellular opioid peptides, thereby limiting their availability for classical receptors.

Example 7. Use of the Peptides of the Invention to Regulate the Availability of Endogenous Opioid Peptides in CNS Opioid Centres To establish a physiological relevance of the observed opioid peptide scavenging capacity of ACKR3, present inventors then analysed, using the Brainspan database (www.brainspan.org), its gene expression profile in comparison with classical opioid receptors in different brain regions corresponding to important centres for opioid signalling/activity. Interestingly, not only was ACKR3 expressed in many of these regions such as amygdala, hippocampus or medial prefrontal cortex, its expression was often higher (up to 100 fold) than that of MOR (OPRM1), KOR (OPRK1), DOR (OPRD1) and NOP (OPRL1) in the same region (FIG. 7A). These data were further confirmed by qPCR on human brain samples, where additional opioid centres such as dentate gyrus or locus coeruleus showed a similar high ACKR3 expression (FIG. 7B).

Considering the expression of ACKR3 in the same regions of the CNS as the classical opioid receptors and its ability to efficiently internalise opioid peptides without inducing downstream signalling, particularly G protein mediated signalling, present inventors wondered whether ACKR3 might influence classical opioid receptor signalling by regulating the availability of their ligands. To validate this hypothesis and the inability of ACKR3 to trigger signalling in a more physiological context, present inventors used small molecule neural precursor cells (smNPCs), that endogenously express ACKR3 but no classical opioid receptors (FIG. 7C). Present inventors confirmed that just like U87-ACKR3 cells, smNPCs express higher proportion of ACKR3 intracellularly compared to the cell surface (FIG. 7D) and that they are able to accumulate labelled dynorphin A (1-13) (FIG. 7E) without activating the ERK signalling pathway (FIG. 7F). This uptake was significantly reduced when smNPCs were pretreated with LIH383, but not with the LIHctrl peptide (FIG. 7E). In line with U87 cell results, this uptake was also associated with a decrease of the extracellular dynorphin A concentration and consequently its ability to signal through its corresponding classical opioid receptor (FIG. 7G).

To ultimately confirm the scavenging function of ACKR3 for opioid peptides, the present inventors monitored ex vivo dynorphin A-mediated inhibition of spontaneous neuron depolarization (i.e. neuronal firing) in explants of rat locus coeruleus, one of the brain regions where ACKR3 is found together with KOR and MOR (FIG. 7B). Treatment with dynorphin A led to a dose-dependent inhibition of neuron depolarization (i.e. neuronal firing) with total inhibition obtained with 1 μM (FIG. 7H). However, the same concentration of dynorphin A did not lead to a change in neuronal firing rate when pretreated with naloxone, indicating that the dynorphin A-induced inhibition of the firing can be attributed to a classical opioid receptor. Treatment with LIH383 at concentration as high as 3 μM however did not lead to significant inhibition of neuronal firing, further confirming the inability of ACKR3 to trigger classical G protein signalling in this region of the CNS (FIG. 7H).

Interestingly, pretreatment of locus coeruleus neurons with LIH383 (1 or 3 μM) to selectively block the scavenging capacity of ACKR3 resulted in a significant increase of depolarization inhibition and an apparent improved potency of dynorphin A towards its classical receptors (FIG. 7I). This observation is in line with present inventors' in vitro data and suggests that also in vivo, in a more physiological environment and at endogenous receptor abundance, ACKR3 may exert its scavenging function to shape opioid gradients and thereby fine-tune signalling of opioid peptides through their classical opioid receptors.

---

The invention claimed is:

1. A selective atypical chemokine receptor 3 (ACKR3) modulating peptide comprising amino acid sequence FGGX$_1$MRRX$_2$ (SEQ ID NO: 1), wherein X$_1$ is F or W; X$_2$ is K, V or F; and the peptide has a length of at most 15 amino acids.

2. The peptide according to claim 1, wherein X$_1$ is F.

3. The peptide according to claim 1, wherein X$_2$ is K.

4. The peptide according to claim 1, comprising the amino acid sequence: FGGX$_1$MRRX$_2$X$_3$ (SEQ ID NO: 2), wherein X$_3$ can be any amino acid.

5. The peptide according to claim 1, comprising an amino acid sequence selected from FGGFMRRK (SEQ ID NO: 3), FGGFMRRKR (SEQ ID NO: 4), FGGFMRRVR (SEQ ID NO: 5), and FGGWMRRK (SEQ ID NO: 6).

6. A fusion protein comprising the peptide according to claim 1.

7. A nucleic acid expression cassette comprising a nucleic acid encoding for the peptide according to claim 1, operably linked to a promoter, transcriptional and translational regulatory signals, or a combination thereof.

8. A vector comprising the nucleic acid encoding for the peptide according to claim 1.

9. The vector according to claim 8, wherein the vector is a viral vector.

10. A pharmaceutical composition comprising the peptide according to claim 1 and optionally a pharmaceutically acceptable carrier.

11. A method for treating a disease or condition selected from distress dysfunction diseases or conditions, pain, and atherosclerosis, comprising administering to the subject a therapeutically effective amount of the peptide according to claim 1.

12. An in vitro method for identifying an agent useful as a therapeutic, comprising contacting cells expressing the atypical chemokine receptor 3 (ACKR3) polypeptide with said agent in the presence of an ACKR3 modulating peptide according to claim 1, and determining whether said agent is capable of inhibiting β-arrestin-1 or β-arrestin-2 recruitment to the ACKR3 polypeptide.

13. A kit for diagnosing, predicting, prognosing or monitoring a disease or condition characterized by an aberrant level of atypical chemokine receptor 3 (ACKR3) polypeptide in a subject, the kit comprising:

(a) the peptide according to claim 1; and (b) a reference value of the level of ACKR3 polypeptide, wherein said reference value represents a known diagnosis, prediction or prognosis of the disease or condition characterized by an aberrant level of ACKR3 polypeptide.

14. The peptide according to claim 1, wherein X$_3$ is R or A.

15. The peptide according to claim 1, wherein the C-terminus of the peptide is NH$_2$-substituted.

* * * * *